US012104152B2

(12) United States Patent
Khurana et al.

(10) Patent No.: US 12,104,152 B2
(45) Date of Patent: Oct. 1, 2024

(54) 2'F-ANA-LET7 MEDIATED UTROPHIN UPREGULATION FOR DMD THERAPY

(71) Applicants: THE TRUSTEES OF THE UNIVERSITY OF PENNSYLVANIA, Philadelphia, PA (US); AUM LifeTech, Inc, Philadelphia, PA (US)

(72) Inventors: Tejvir S. Khurana, Narnerth, PA (US); Manoj Kumar Mishra, Philadelphia, PA (US); Veenu Aishwarya, Philadelphia, PA (US)

(73) Assignees: The Trustees of the University of Pennsylvania, Philadelphia, PA (US); AUM LifeTech, Inc, Philadelphia, PA (US)

( * ) Notice: Subject to any disclaimer, the term of this patent is extended or adjusted under 35 U.S.C. 154(b) by 31 days.

(21) Appl. No.: 16/982,467

(22) PCT Filed: Mar. 18, 2019

(86) PCT No.: PCT/US2019/022826
§ 371 (c)(1),
(2) Date: Sep. 18, 2020

(87) PCT Pub. No.: WO2019/183005
PCT Pub. Date: Sep. 26, 2019

(65) Prior Publication Data
US 2021/0040481 A1    Feb. 11, 2021

Related U.S. Application Data

(60) Provisional application No. 62/645,170, filed on Mar. 19, 2018.

(51) Int. Cl.
*C07H 21/04* (2006.01)
*A61P 21/00* (2006.01)
*C12N 15/113* (2010.01)

(52) U.S. Cl.
CPC ............ *C12N 15/113* (2013.01); *A61P 21/00* (2018.01)

(58) Field of Classification Search
None
See application file for complete search history.

(56) References Cited

U.S. PATENT DOCUMENTS

| | | | | |
|---|---|---|---|---|
| 8,916,532 B2 * | 12/2014 | Moorwood | ........... | C12N 15/113 435/375 |
| 2005/0142535 A1 * | 6/2005 | Damha | ................ | C12N 15/113 435/5 |
| 2009/0105467 A1 | 4/2009 | Damha | | |
| 2012/0122953 A1 * | 5/2012 | Moorwood | ........... | C12N 15/113 435/375 |
| 2013/0197057 A1 | 8/2013 | Petrecca et al. | | |

FOREIGN PATENT DOCUMENTS

| WO | WO 2001/023613 | 4/2001 |
|----|---------------|--------|
| WO | WO 2003/064441 | 8/2003 |
| WO | WO 2018/017719 | 1/2018 |

OTHER PUBLICATIONS

Rodrigues, Merryl, et al. ("Current translational research and murine models for Duchenne muscular dystrophy." Journal of neuromuscular diseases 3.1 (2016): 29-48).*
International Preliminary Report on Patentability and Written Opinion from PCT Patent Application No. PCT/US2019/022826 dated Oct. 1, 2020.
Summerton et al. "Morpholino antisense oligomers: design, preparation, and properties." Antisense and Nucleic Acid Drug Development 7.3 (1997): 187-195.
Trempe et al. "NMR solution structure of an oligonucleotide hairpin with a 2'F-ANA/RNA stem: implications for RNase H specificity toward DNA/RNA hybrid duplexes." Journal of the American Chemical Society 123.21 (2001): 4896-4903.

\* cited by examiner

*Primary Examiner* — Kimberly Chong
(74) *Attorney, Agent, or Firm* — Mark S. Cohen; PEARL COHEN ZEDEK LATZER BARATZ LLP

(57) ABSTRACT

The invention relates to compositions and methods for enhancing or upregulating utrophin protein production and methods for treating myopathies, such as Duchenne Muscular Dystrophy (DMD). Specifically, the invention relates to compositions, such as oligonucleotides, and methods for enhancing or upregulating utrophin in a subject by blocking binding of let-7c miRNA to the utrophin mRNA 3 untranslated region (UTR).

15 Claims, 22 Drawing Sheets

Specification includes a Sequence Listing.

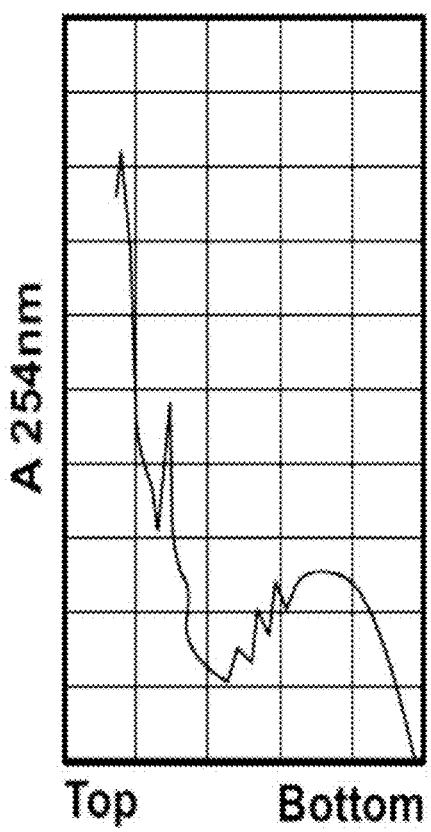
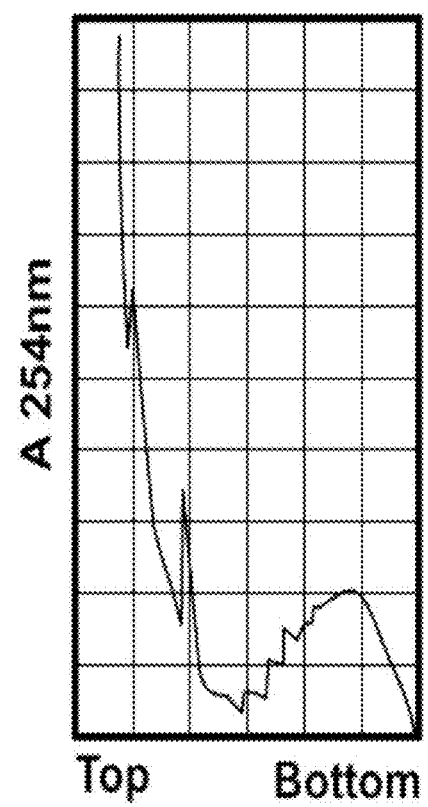
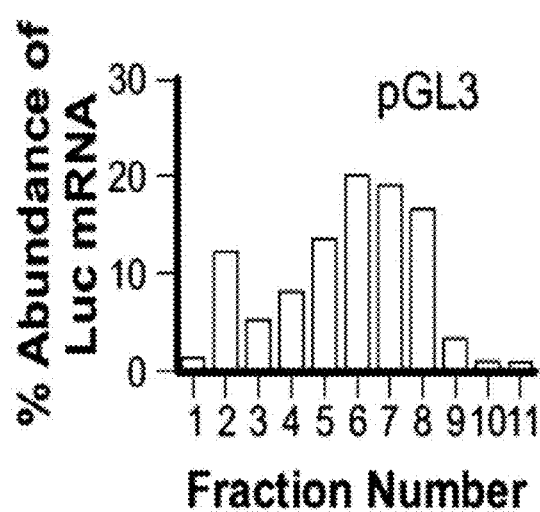
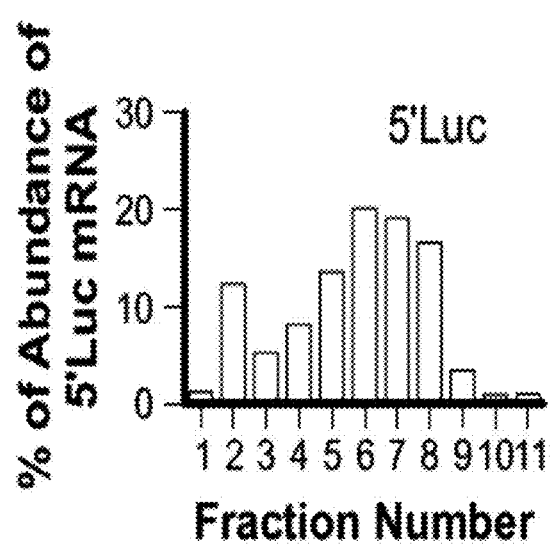
Figure 4A          Figure 4B

Percentage of centrally nucleated fibers (CNFs) in TA muscle

2'F-ANA-LET7 MEDIATED UTROPHIN UPREGULATION FOR DMD THERAPY

CROSS-REFERENCE TO RELATED APPLICATIONS

This application is a U.S. national stage application under 37 U.S.C. 371 of PCT International Application PCT/US2019/022826, filed Mar. 18, 2019, which claims benefit of U.S. Provisional Patent Application Ser. No. 62/645,170, filed Mar. 19, 2018, the priority date of which is hereby claimed, the contents of each of which is hereby incorporated by reference in its entirety.

FIELD OF THE INVENTION

The invention relates to compositions and methods for enhancing utrophin protein production and methods for treating myopathies, such as Duchenne Muscular Dystrophy (DMD). Specifically, the invention relates to compositions, such as oligonucleotides, and methods for enhancing or upregulating utrophin in a subject by blocking binding of let-7c miRNA to the utrophin mRNA 3' untranslated region (UTR).

BACKGROUND OF THE INVENTION

Duchenne Muscular Dystrophy (DMD) is one of a group of muscular dystrophies characterized by the enlargement of muscles. DMD is one of the most prevalent types of muscular dystrophy and has rapid progression of muscle degeneration, which occurs early in life. DMD is X-linked and affect mainly males—an estimated 1 in 3,500 boys worldwide.

The gene for DMD, found on the X chromosome, encodes a large protein—dystrophin. Dystrophin is required inside muscle cells for structural support: it is thought to strengthen muscle cells by anchoring elements of the internal cytoskeleton to the surface membrane and external structures. Without it, the muscle cannot produce force effectively and is susceptible to damage during contraction, eventually leading to muscle death and replacement by fatty and fibrous tissue. The accompanying immune response can add to the damage.

A mouse model for DMD exists, and is proving useful for furthering understanding both normal dystrophin function and the pathology of the disease. Specifically, experiments enhancing production of utrophin, a dystrophin relative, in order to compensate for dystrophin loss are promising, and may lead to effective therapies for this devastating disease. Accordingly, a need exists for enhancing utrophin production to treat muscular dystrophies and other myopathies.

MicroRNAs (miRNAs) are small RNA molecules encoded in plant and animal genomes. These highly conserved, ~21-mer RNAs regulate gene expression by binding to the 3' or 5'-untranslated regions (3'-UTR or 5'-UTR) of specific mRNAs.

Although miRNA was first described well over a decade ago, only recently has the breadth and diversity of this class of small, regulatory RNAs been appreciated. Much effort has gone into understanding how, when, and where miRNAs are produced and function in cells, tissues, and organisms. Each miRNA is thought to regulate multiple genes, and since hundreds of miRNA genes are predicted to be present in higher eukaryotes the potential regulatory circuitry afforded by miRNA is enormous.

MicroRNAs may act as key regulators of processes as diverse as early development, cell proliferation and cell death, apoptosis and fat metabolism, and cell differentiation. Studies of miRNA expression implicate them in brain development, chronic lymphocytic leukemia, colonic adenocarcinoma, Burkett's Lymphoma, and viral infection, suggesting possible links between miRNAs and viral disease, neurodevelopment, and cancer. miRNAs are differentially expressed in myopathies and have been implicated in heart disease. Accordingly, a need exists to determine the role of miRNAs in utrophin production to treat myopathies or utrophin mediated diseases.

Oligonucleotides containing natural sugars (D-ribose and D-2-deoxyribose) and phosphodiester (PO) linkages are rapidly degraded by serum and intracellular nucleases, which limit their utility as effective therapeutic agents. Chemical strategies employed to improve nuclease stability include modification of the sugar moiety, the base moiety, and/or modification or replacement of the internucleotide phosphodiester linkage. To date, the most widely studied analogues are the phosphorothioate (PS) oligodeoxynucleotides, in which one of the non-bridging oxygen atoms in the phosphodiester backbone is replaced with a sulfur.

Arabinonucleosides are stereoisomers of ribonucleosides, differing in the configuration at the 2'-position of the sugar ring. They have substantially impacted chemotherapy, as they have been extensively used as antiviral and anticancer drugs. β-D-Arabinofuranosylcytosine (ara-C) is the most successful nucleoside antileukemic agent; it is widely used in combination therapy or at high doses as a single agent to treat patients with acute lymphoblastic and myeloblastic leukemias.

Incorporation of 2'-deoxy-2'-fluoro-β-D-arabinofuranosylpyrimidine nucleosides (2'F-ara-N, where N=C, G, A and U) at multiple positions within a normal DNA chain and hybridization of such (2'-F)ANA-DNA "chimeras" to complementary RNA show that substitutions with 2'F-araU, 2'F-araG, 2'F-araA, and 2'F-araC significantly increased stability, specificity and high affinity to the target. Such chemical modifications also provided the capability of self-delivery (without the use of a transfection or delivery agent) of these oligonucleotides when compared to unmodified oligodeoxynucleotide strands. Delivery agents are known to have toxic effects in cellular and animal studies, thus such self-delivering FANA oligonucleotides significantly reduce toxicity. These FANA-DNA chimeras were made using a phosphorothioate backbone.

SUMMARY OF THE INVENTION

This disclosure relates to methods and compositions for enhancing or upregulating utrophin protein production in a cell by inhibiting a utrophin microRNA molecule or by blocking binding of the microRNA to the utrophin mRNA.

Utrophin upregulation is a therapeutic strategy for DMD. Normally, Utrophin-A expression is repressed through the 5' and 3'-UTRs by >98% at the translational level (FIG. 1A). The Utrophin 5' and 3'-UTR contains microRNA target sites. Utrophin 3'-UTR exhibits its inhibitory effect both on IRES and on cap-dependent translation. Inhibition of microRNAs that target Utrophin UTRs by blocking the microRNA binding site in the mRNA or by binding to the microRNA itself are therapeutic strategies for DMD (FIG. 1B).

In one aspect, provided herein are oligonucleotides comprising one or more arabinonucleotides (e.g., 2'-deoxy-2'-fluoro-β-D-arabinonucleosides), wherein the oligonucleotide specifically hybridizes to a Let-7c microRNA binding sequence in a utrophin mRNA 3' untranslated region (UTR) and inhibits the binding of the Let-7c microRNA to the utrophin mRNA 3'-UTR. In another aspect, provided herein are pharmaceutical compositions that include an oligonucleotide described herein and at least one pharmaceutically acceptable excipient. In some embodiments, the heteroduplex formed by the oligonucleotide and the binding sequence is resistant to cleavage by RNase H. In some embodiments, the oligonucleotides comprise alternating segments of arabinonucleotides (ANA) and 2'-deoxynucleotides.

In another aspect, provided herein are methods of treating a muscle disease or muscular dystrophy (e.g., Duchenne Muscular Dystrophy (DMD)) in a subject, by administering to the subject an effective amount of an oligonucleotide comprising one or more arabinonucleotides (e.g., 2'-deoxy-2'-fluoro-β-D-arabinonucleosides), wherein the oligonucleotide specifically hybridizes to a Let-7c microRNA binding sequence in a utrophin mRNA 3'-UTR and inhibits binding of the Let-7c microRNA to the utrophin mRNA 3'-UTR. In another aspect, provided herein are methods for reducing the symptoms associated with a muscular dystrophy (e.g., DMD), in a subject, by administering to the subject an effective amount of an oligonucleotide comprising one or more arabinonucleotides (e.g., 2'-deoxy-2'-fluoro-β-D-arabinonucleosides), wherein the oligonucleotide specifically hybridizes to a Let-7c microRNA binding sequence in a utrophin mRNA 3'-UTR and inhibits binding of the Let-7c microRNA to the utrophin mRNA 3'-UTR.

In another aspect, provided herein are methods for enhancing utrophin production in a subject by administering to the subject an effective amount of an oligonucleotide comprising one or more arabinonucleotides (e.g., 2'-deoxy-2'-fluoro-β-D-arabinonucleosides), wherein the oligonucleotide specifically hybridizes to a Let-7c microRNA binding sequence in a utrophin mRNA 3'-UTR and inhibits binding of the Let-7c microRNA to the utrophin mRNA 3'-UTR. In another aspect, provided herein are methods for inhibiting binding of a Let-7c microRNA with a utrophin mRNA 3' untranslated region (UTR) in a subject by administering to the subject an effective amount of an oligonucleotide comprising one or more arabinonucleotides (e.g., 2'-deoxy-2'-fluoro-β-D-arabinonucleosides), wherein the oligonucleotide specifically hybridizes to a Let-7c microRNA binding sequence in a utrophin mRNA 3'-UTR and inhibits binding of the Let-7c microRNA to the utrophin mRNA 3'-UTR.

In another aspect, provided herein are methods for enhancing utrophin production in a cell by administering to the cell an effective amount of an oligonucleotide comprising one or more arabinonucleotides (e.g., 2'-deoxy-2'-fluoro-β-D-arabinonucleosides), wherein the oligonucleotide specifically hybridizes to a Let-7c microRNA binding sequence in a utrophin mRNA 3'-UTR and inhibits binding of the Let-7c microRNA to the utrophin mRNA 3'-UTR. In another aspect, provided herein are methods for inhibiting binding of a Let-7c microRNA with a utrophin mRNA 3' untranslated region (UTR) in a cell by administering to the cell an effective amount of an oligonucleotide comprising one or more arabinonucleotides (e.g., 2'-deoxy-2'-fluoro-β-D-arabinonucleosides), wherein the oligonucleotide specifically hybridizes to a Let-7c microRNA binding sequence in a utrophin mRNA 3'-UTR and inhibits binding of the Let-7c microRNA to the utrophin mRNA 3'-UTR.

Other features and advantages will become apparent from the following detailed description, examples, and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE FIGURES

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

FIG. 4 shows that C2C12 cell extract was resolved on a sucrose density gradient, collected into eleven fractions, and the target mRNA level in each fraction was determined by q-PCR analysis and quantified as shown in the bar graphs for the constructs of FIG. 2.

DETAILED DESCRIPTION OF THE INVENTION

Figures 1A, 1B:
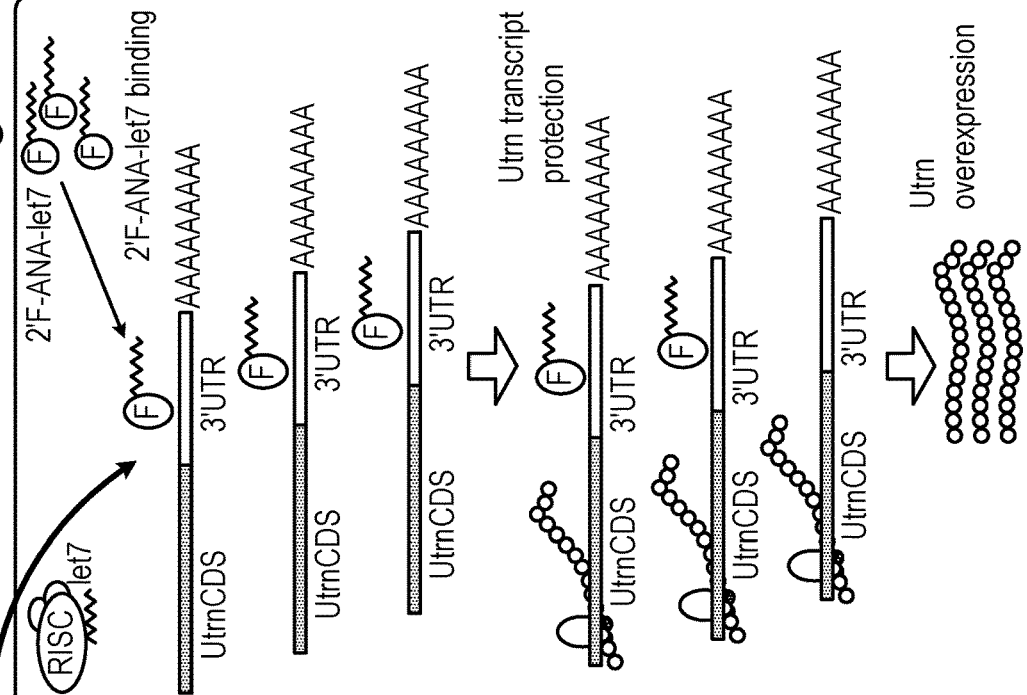
FIG. 1 Shows 2'F-ANA-let7 oligonucleotide mediated miRNA site blocking strategy for utrophin upregulation. Normally utrophin protein is expressed at low levels as it is subject to let-7c mediated repression (A). 2'F-ANA-let7 oligonucleotide mediated miRNA site blocking in the 3'UTR, resulting in utrophin upregulation (B).
Figure 2A:
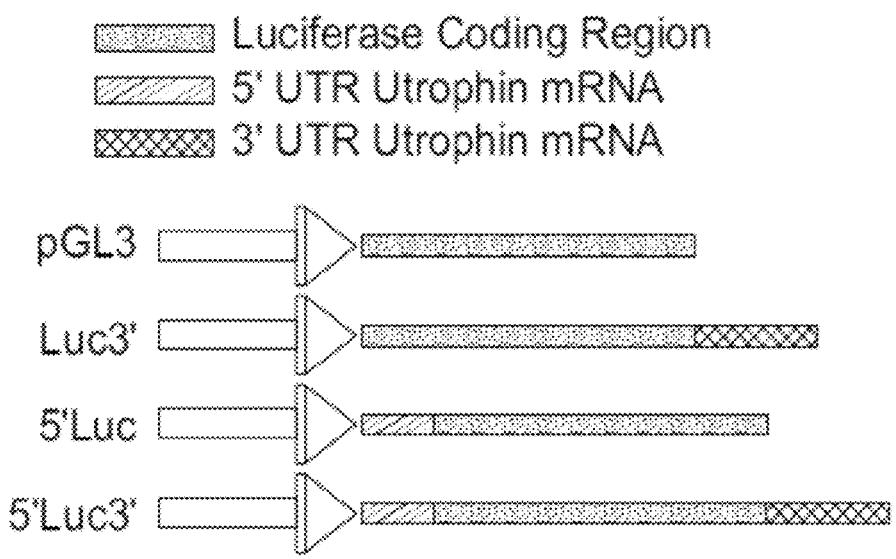
FIG. 2 shows that C2C12 cells were transfected with luciferase reporter constructs (A and B) and mRNA levels and luciferase activity were analyzed (C). Also, C2C12 cell extract was resolved on a sucrose density gradient, collected into eleven fractions, and the target mRNA level in each fraction was determined by q-PCR analysis (D).
Figure 2B:
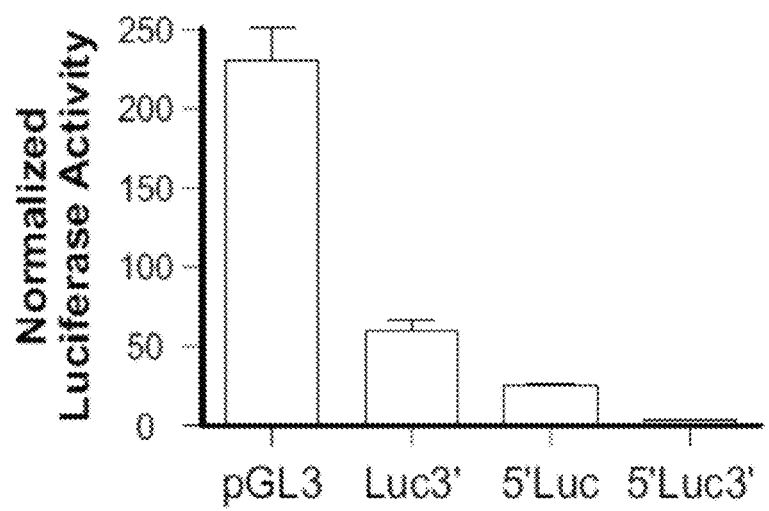
Figure 2C:
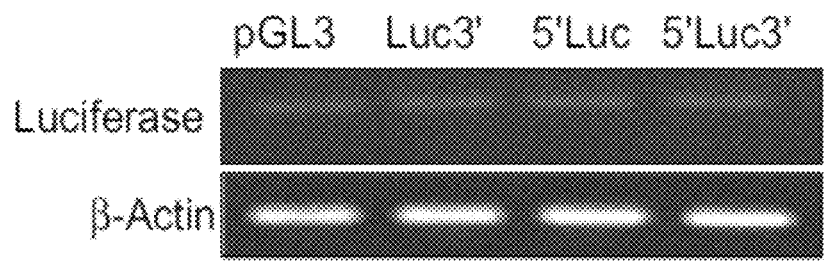
Figure 2D:
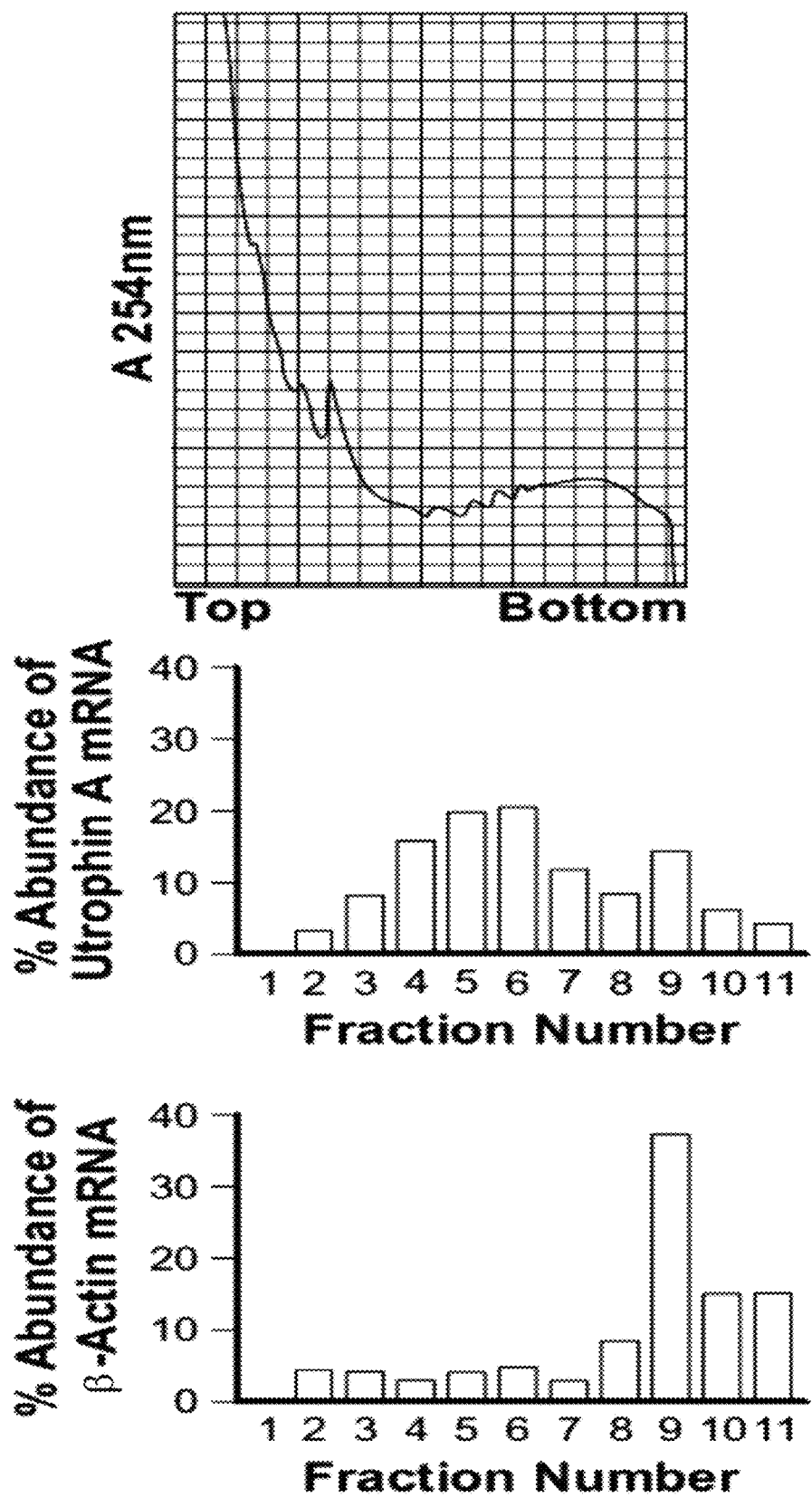

In one aspect, provided herein are methods of enhancing utrophin protein production in a cell, comprising the step of inhibiting a utrophin microRNA molecule. In another aspect, provided herein are methods of enhancing utrophin protein production in a cell, comprising the step of blocking binding of a utrophin microRNA molecule to utrophin mRNA. In one embodiment, the cell is a muscle cell.

In another aspect, provided herein are methods of treating a muscle disease or muscular dystrophy (e.g., Duchenne Muscular Dystrophy (DMD)), in a subject (e.g., a human subject), by administering to the subject an effective amount of an oligonucleotide comprising one or more arabinonucleotides (e.g., 2'-deoxy-2'-fluoro-β-D-arabinonucleosides), wherein the oligonucleotide specifically hybridizes to a Let-7c microRNA binding sequence in a utrophin mRNA 3'-UTR and inhibits binding of the Let-7c microRNA to the utrophin mRNA 3'-UTR. In some embodiments, the oligonucleotide has a sequence that includes a nucleic acid sequence set forth in SEQ ID NOs: 24-55 or 64-75. In some embodiments, the oligonucleotide is administered intramuscularly. In some embodiments, the oligonucleotide is administered systemically. In some embodiments, administration of the oligonucleotide is gymnotic.

In another aspect, provided herein are oligonucleotides comprising one or more arabinonucleotides (e.g., 2'-deoxy-2'-fluoro-β-D-arabinonucleosides), wherein the oligonucleotide specifically hybridizes to a Let-7c microRNA binding sequence in a utrophin mRNA 3' untranslated region (UTR) and inhibits the binding of the Let-7c microRNA to the utrophin mRNA 3'-UTR. In another aspect, provided herein are pharmaceutical compositions that include an oligonucleotide described herein and at least one pharmaceutically acceptable excipient. In some embodiments, the heteroduplex formed by the oligonucleotide and the binding sequence is resistant to cleavage by RNase H. In some embodiments, the oligonucleotide has a sequence that includes a nucleic acid sequence set forth in SEQ ID NOs: 24-55 or 64-75. In a preferred embodiment, the oligonucleotide has a sequence that includes a nucleic acid sequence set forth in SEQ ID NOs: 64-75. The nucleic acid sequences of SEQ ID NOs. 64-75 are listed in the Table 1 below.

TABLE 1

| SEQUENCE (5'-3') | SEQ ID NO: |
|---|---|
| CUGAGGUAGAAAGGUGAUCAUGGCUC | 64 |
| CUGAGGUAGAAAGGUGAUCAU | 65 |
| GUAGAAAGGUGAUCATGGCUC | 66 |
| CUGAGGUAGAAAGGUGAUCAUGGCUC | 67 |
| CUGAGGUAGAAAGGUGAUCAUG | 68 |
| GGUAGAAAGGUGAUCAUGGCUC | 69 |
| CUGAGGUAGAAAGGUGAUCAUGGCUC | 70 |
| CUGAGGUAGAAAGGUGAUCAU | 71 |
| GUAGAAAGGUGAUCATGGCUC | 72 |
| CTGAGGUAGAAAGGUGAUCAUGGCUC | 73 |
| CTGAGGUAGAAAGGUGAUCAU | 74 |
| GTAGAAAGGUGAUCATGGCTC | 75 |

In another aspect, provided herein are methods for enhancing utrophin production in a cell by administering to the cell (e.g., a muscle cell) an effective amount of an oligonucleotide comprising one or more arabinonucleotides (e.g., 2'-deoxy-2'-fluoro-β-D-arabinonucleosides), wherein the oligonucleotide specifically hybridizes to a Let-7c microRNA binding sequence in a utrophin mRNA 3'-UTR and inhibits binding of the Let-7c microRNA to the utrophin mRNA 3'-UTR. In another aspect, provided herein are methods for inhibiting binding of a Let-7c microRNA with a utrophin mRNA 3' untranslated region (UTR) in a cell by administering to the cell an effective amount of an oligonucleotide comprising one or more arabinonucleotides (e.g., 2'-deoxy-2'-fluoro-β-D-arabinonucleosides), wherein the oligonucleotide specifically hybridizes to a Let-7c microRNA binding sequence in a utrophin mRNA 3'-UTR and inhibits binding of the Let-7c microRNA to the utrophin mRNA 3'-UTR. In some embodiments, translation of utrophin in a muscle cell is increased over basal levels by about 10%, 20%, 25%, 30%, 40%, 50%, 60%, 70%, 75%, 80%, 90% or more. In some embodiments, translation of utrophin in a muscle cell is increased over basal levels by about 2-fold, 3-fold, 4-fold, 5-fold, 10-fold, 20-fold, 25-fold, 30-fold, 40-fold, 50-fold, 75-fold, 100-fold or more.

In some embodiments, provided herein are methods of enhancing utrophin protein production in a cell (e.g., a muscle cell), comprising the step of contacting a microRNA molecule that binds an utrophin mRNA with an inhibitor, thereby enhancing utrophin protein production in a cell. In some embodiments, provided herein are methods of enhancing utrophin protein production in a cell (e.g., a muscle cell), comprising the step of contacting a microRNA molecule that binds an utrophin mRNA 3'-UTR with an inhibitor, thereby enhancing utrophin protein production in a cell. In some embodiments, provided herein are methods of enhancing utrophin protein production in a cell (e.g., a muscle cell), comprising the step of contacting a microRNA molecule that binds an utrophin mRNA 5'-UTR with an inhibitor, thereby enhancing utrophin protein production in a cell.

In some embodiments, provided herein are methods of enhancing utrophin protein production in a cell (e.g., a muscle cell), comprising the step of contacting a microRNA molecule that binds an utrophin mRNA 3'-UTR with an antisense molecule which inhibits binding of the microRNA molecule to a 3'-UTR utrophin mRNA, thereby enhancing utrophin protein production in a cell. In some embodiments, the cell is a muscle cell. In some embodiments, provided herein are methods of enhancing utrophin protein production in a cell (e.g., a muscle cell), comprising the step of contacting a microRNA molecule that binds an utrophin mRNA 5'-UTR with an antisense molecule which inhibits binding of the microRNA molecule to a 5'-UTR utrophin mRNA, thereby enhancing utrophin protein production in a cell.

In some embodiments, provided herein are methods of enhancing utrophin protein production in a cell (e.g., a muscle cell), comprising the step of contacting a muscle cell specific microRNA molecule that binds an utrophin mRNA 3'-UTR with an inhibitor, thereby enhancing utrophin protein production in a cell. In some embodiments, provided herein are methods of enhancing utrophin protein production in a cell (e.g., a muscle cell), comprising the step of contacting a muscle cell specific microRNA molecule that binds an utrophin mRNA 5'-UTR with an inhibitor, thereby enhancing utrophin protein production in a cell.

In some embodiments, provided herein are methods of enhancing utrophin protein production in a cell (e.g., a muscle cell), comprising the step of contacting a muscle cell specific microRNA molecule that binds an utrophin mRNA 3'-UTR with an antisense molecule which inhibits binding of the microRNA molecule to a 3'-UTR utrophin mRNA, thereby enhancing utrophin protein production in a cell. In some embodiments, provided herein are methods of enhancing utrophin protein production in a cell (e.g., a muscle cell), comprising the step of contacting a muscle cell specific microRNA molecule that binds an utrophin mRNA 5'-UTR with an antisense molecule which inhibits binding of the microRNA molecule to a 5'-UTR utrophin mRNA, thereby enhancing utrophin protein production in a cell.

In some embodiments, provided herein are methods of enhancing utrophin protein production in a cell (e.g., a muscle cell), comprising the step of contacting an utrophin mRNA with a molecule that binds a microRNA binding site within utrophin mRNA, thereby blocking interaction between utrophin mRNA and the microRNA and enhancing utrophin protein production in a cell. In some embodiments, provided herein are methods of enhancing utrophin protein production in a cell (e.g., a muscle cell), comprising the step of contacting an utrophin mRNA with a molecule that binds a microRNA binding site within utrophin mRNA 3'-UTR, thereby blocking interaction between utrophin mRNA 3'-UTR and the microRNA and enhancing utrophin protein production in a cell. In some embodiments, the cell is a muscle cell.

In some embodiments, provided herein are methods of enhancing utrophin protein production in a cell (e.g., a muscle cell), comprising the step of contacting an utrophin mRNA with a molecule that binds a microRNA binding site within utrophin mRNA 5'-UTR, thereby blocking interaction between utrophin mRNA 5'-UTR and the microRNA and enhancing utrophin protein production in a cell. In some embodiments, provided herein are methods of enhancing utrophin protein production in a cell (e.g., a muscle cell), comprising the step of contacting an utrophin mRNA with a molecule that binds a muscle cell specific microRNA binding site within utrophin mRNA, thereby blocking interaction between utrophin mRNA and the muscle cell specific microRNA and enhancing utrophin protein production in a cell.

In some embodiments, provided herein are methods of enhancing utrophin protein production in a cell (e.g., a muscle cell), comprising the step of contacting an utrophin mRNA with a molecule that binds a muscle cell specific microRNA binding site within utrophin mRNA 3'-UTR, thereby blocking interaction between utrophin mRNA 3'-UTR and the muscle cell specific microRNA and enhancing utrophin protein production in a cell. In some embodiments, provided herein are methods of enhancing utrophin protein production in a cell (e.g., a muscle cell), comprising the step of contacting an utrophin mRNA with a molecule that binds a muscle cell specific microRNA binding site within utrophin mRNA 5'-UTR, thereby blocking interaction between utrophin mRNA 5'-UTR and the muscle cell specific microRNA and enhancing utrophin protein production in a cell.

In some embodiments, provided herein are methods of stabilizing utrophin mRNA in a cell (e.g., a muscle cell), comprising the step of contacting an utrophin mRNA with a molecule that binds a microRNA binding site within utrophin mRNA, thereby blocking interaction between utrophin mRNA and the microRNA and stabilizing utrophin mRNA. In some embodiments, provided herein are methods of stabilizing utrophin mRNA, comprising the step of contacting an utrophin mRNA with a molecule that binds a microRNA binding site within utrophin mRNA 3'-UTR, thereby blocking interaction between utrophin mRNA 3'-UTR and the microRNA and stabilizing utrophin mRNA. In some embodiments, provided herein are methods of stabilizing utrophin mRNA, comprising the step of contacting an utrophin mRNA with a molecule that binds a microRNA binding site within utrophin mRNA 5'-UTR, thereby blocking interaction between utrophin mRNA 5'-UTR and the microRNA and stabilizing utrophin mRNA. In some embodiments, provided herein are methods of stabilizing utrophin mRNA in a cell (e.g., a muscle cell), comprising the step of contacting an utrophin mRNA with a molecule that binds a muscle cell specific microRNA binding site within utrophin mRNA, thereby blocking interaction between utrophin mRNA and the muscle cell specific microRNA and stabilizing utrophin mRNA. In some embodiments, provided herein are methods of stabilizing utrophin mRNA in a cell (e.g., a muscle cell), comprising the step of contacting an utrophin mRNA with a molecule that binds a muscle cell specific microRNA binding site within utrophin mRNA 3'-UTR, thereby blocking interaction between utrophin mRNA 3'-UTR and the muscle cell specific microRNA and stabilizing utrophin mRNA. In some embodiments, provided herein are methods of stabilizing utrophin mRNA in a cell (e.g., a muscle cell), comprising the step of contacting an utrophin mRNA with a molecule that binds a muscle cell specific microRNA binding site within utrophin mRNA 5'-UTR, thereby blocking interaction between utrophin mRNA 5'-UTR and the muscle cell specific microRNA and stabilizing utrophin mRNA.

In one aspect, provided herein are oligonucleotides comprising one or more arabinonucleotides (e.g., 2'-deoxy-2'-fluoro-β-D-arabinonucleosides), wherein the oligonucleotide specifically hybridizes to a Let-7c microRNA binding sequence in a utrophin mRNA 3' untranslated region (UTR) and inhibits the binding of the Let-7c microRNA to the utrophin mRNA 3'-UTR. In another aspect, provided herein are pharmaceutical compositions that include an oligonucleotide described herein and at least one pharmaceutically acceptable excipient. In some embodiments, the heteroduplex formed by the oligonucleotide and the binding sequence is resistant to cleavage by RNase H. In some embodiments, the oligonucleotide comprises one or more phosphorothioate internucleotide linkages. In some embodiments, all internucleotide linkages in the oligonucleotide are phosphorothioates.

In some embodiments, provided herein are oligonucleosides comprising alternating segments of sugar-modified nucleosides and 2'-deoxynucleosides. In some embodiments, the oligonucleosides or nucleosides comprise a phosphate, thereby being oligonucleotide or nucleotides, respectively. In some embodiments, such alternating segments comprise alternating segments of arabinonucleotides (ANA), such as 2'F-ANA (or FANA), and DNA. "Arabinonucleotide" as used herein refers to a nucleotide comprising an arabinofuranose sugar.

The wild-type mouse (*Mus musculus*) utrophin mRNA sequence can be found in GenBank (accession number AK035043.1). The mouse utrophin mRNA 3'-UTR has the following nucleotide sequence (the Let-7c microRNA binding sequence is in bold and underlined):

```
                                      (SEQ ID NO: 13)
TGAGCATCTATCCAGCCAGCCAACATTTCCCGACCTTCAGTATTGCCCTC

TTCTGCAAATGCCAATCCCAAGACCCATTCAACCCCAAAGCTCCGTGGCT

CCACGACACAAGCTGTTGAGTGCTTACTGGGTGTTCTACTGAGGGAACCA
```

-continued
```
AACACTGACTATCCAAAGAGAAAAGGATATTTTGGTTTTCTAATAACGTA

TATTATTGTTTTCTTCTCCCCTTTCTATGCAACTGTAAATTAATGAACAG

AGAAGTATTTGGAGGTGGTAAAGCATTTGTCACTGATTTGTATAATATAT

ACAGCCATGGGAAAGTGGGTGGGGGCTTTCTAATATGAAACTGTCTTTTT

AATAACCAAGAGAAAAAATTGCATAAGAATTAGACCACTTTACATTATTA

CATTCCTTCTGCTGTTCACATTAACCTTGTACAATAACTTCACTTATTAT

TTGACTGTTTTACCATTATGTTTTGGTTATTTATAAATTTATCAGCCATA

CAAACAAATAGATTCTATGTATTTGTTTCTATAATCTGGCCAAATTCCTA

AGTTCATATATTTGAATCAAATATTTTACATATGTGGAGTAGGCAGGCAT

TCTGAAGATACTATTTAACTTTAGTTGACGTCACACACACCATCCTTTAG

TAACCACTGGATGACTACACTAAAAATCCTGTGGACTTTAACGGCAAGCT

GCTGGGGTATTTTTCCTCCTGTTTTTATTCCTTTTTTGTAAGTAGATCTT

GACGTCTTTATTTATTTCATCTTGCAATCTCTATAATAAAGAAGACTGTA

TTGTAATAGTCTCAAAAAATTATTTTACCAAGGGTTACCATTTAAGCATA

TTTTCATTTTGATTCAGAAACCAAAGTTGGTACAACCTCTCCTAGTACAT

GCAACCTTGGTTTTCATGAGAAAACACACGGCAGGCCTTTGCCCATTGTG

AGGAGAGCACACATCATGCTCTTCAGTTTCCTTTGAATAGACTTTTATTG

TTGTTTTTGTATTTTTCGAGTCCTGTGTAAGTTTTGAAAGCTCTGGTTGT

TTCCTTTGTGAAAGCAGGCAGATACTTAGTTGGCTGTCTCATTTGAAGCT

TTGGAGCAGATAGTCAGATGTCTCATGACCCCTCACTTGGCCAGCAGCAC

ATCCGAGAAGGATGTCACTCACAAGCCTACACCACGGCTTCTCTAGAATG

AAATCAGTGCTCGGATGATTGTATCCCTGCCTCTACTTCTGAGTGTGTTC

AACTAGGTATTGGCTTCTTTTTCTTTTTCTTTTCTTTTTTTTTAATTTA

ACACTTAATTGCCGATTTTAGAGAAACCAAAAATAAAGGTGAAGGTAATA

TGTTTTGATTCAAACATATATGCTTTTAAACATCAGACATGCTAACTTTG

GTTCTCTTTACTGGAATCTGGCCCAGAGGAGGTGAAATTTAGAAATGTTA

TTCTTTAGATGGGTGGGTGGGTTGGGGGGCCAAGGGTGTCTATTTTCCAG

CATTAGATATTTTGAGACGAAGAAAATTGTTTTATATAAGGGGAGAGCC

ATGATCACCTTTCTACCTCAGAACCACCTTCCTCCATTGTGTTGGACATA

GCTTTATATGCCGCAGTGTGCAAAACCTAGGGCTGTAGTCAGGCCTTTCC

ATACCCAGGAAGCACCTGTGTAAAGAAGATCAACAGAAACTCCCGGAACT

CAGAACCCCAAGTTGTAGATTTGGTGTCGTCCTTGTTCTTGCTTTGAGGA

GTCATGTATTCTTTTATTTCCTGCCTGTATTTGTATGCAAAATGATCTCT

ATCTGCTATTACAGAAAAAGCTACACAAAACACTACATTGTAACCTTCTG

AGTAATAAATAAGAGGAAATATATTACAGTAACCATGATGAGAAATAAGT

GTATTGTTCTTTTGAAATATGTGGTTAATCGCAGACTGTCATCTAATCTG

TTACATACCGTATTTTTCATCCTGAATAAAAGTAATTTTAACACAAAATG

ACTTTGATGTTTGGCTGTGTTCAGCTGATGAAATCAGATCTCTGAATGTA

TGTGATGAAAGCTAACTATAAGATGATCTATATTCTGATAAATCTAAATA

TTTTCTGAAACTCTCTCTTATACATTAATCTAGTCTCCATTCACTCATTA
```

```
TCTCTCTCTCCTTTCTTGCATATAAATATGATTATATATTTTTCAATTTC

CTGTACAAATCAGAGTCTTATTACTAGGGAAAATGGATGTTATAAGTACA

TTCCTAAAGCCCATTGGGCCTTCATTTTTATAACTTGGAGCTACTGAGAT

TTATCAGGTTACTCTCTCAAATCCACTTTCATCACTAGACTCATAGTTTT

CTATGTATCTATATTATTATAACTAAATAAAAATATACATG.
```

The wild-type human (*Homo sapiens*) utrophin mRNA sequence can be found in GenBank (accession number NM_007124.2). The human utrophin mRNA 3'-UTR has the following nucleotide sequence (the Let-7c microRNA binding sequence is in bold and underlined):

```
                                    (SEQ ID NO: 56)
TGAAGTATTCATCCGGCCAACCAATGTTTCCTGACGTACAGTGTTGCCCT

TTTCAGCAAATGCCAATTCCAAGTTCCATTAAATCAGAAGCTCCATGGCT

CCTTGGCCCACGATGTTGAGTGCTGACTGTGTGTTCTACTGAAAGAGTAA

AACACTGACTATCCAAAGAGAAATGGATATTTTGTTTTTATAATAACCAT

ATATTATTGTTTTCTTCTTCCCTTTCTATGCAAGTGTAAATTAATGAACA

GAGAGGTATTTGGAAATGGTAATACATTTGTCACGGATTTGTATAATGTA

TACAGCATTGGGAAAGTGGGTGGGGGCTTTCTAATATGATACCGTCTTTT

TAATAACTATGACAAAGCTTACATAAGAATTAGAAGACCACTTTACATTT

TTACATTCCTTCTGCTGTTCATATTAACCTTGCACAATTACTTCATTTTT

TCTTTGACTCTTTTACCACAATGTTTTGGTTATTTATAATTTATCAGCCA

TATGTTTATCAGCCATATAACCAACTAGATCCCAAATAGATCCATGTATT

TGTTTCCGTGATTTGGCCACATTAATAAATTCATAAATTTCAATCAAATA

TCTTATATATACACACATATGGTTTAAGCTACAGCCCTGTGTATGCCGTT

TAACTTTATTTGACGTTGCCCACTTACTTCTTTGCTGACCACTTGGATAA

CCGTAATAAAAATCCTATAAGCCTAAATGGCATTTCTTTTGGGATATTTT

TCCTGCATTTTATTCCCTTTTTATATAAGTAGGAATTAATTATTTATTTT

ATGTCTTAATCTATTTGATAAAGAAGACTACATTATAATAATCTCAAAGA

TCATATTACCAAAGGTTGCCCACTTGAGCATATTTTCATTTTGACACAGA

AACAAAATTTAGTACAACCTTTCCTAGTTCCCATGTCTTGATTTTCATCA

TTACATGCACAGCAGACCTTTACCTATTGTGATACCAGAACACATCATTG

TCTTTGGTTCCCTTCAAAGAGAATTTTATTGTTGTTTTGTATTTTCAAGT

CCTTAATAGTTCTTGAAACTCCTAGTTGTTTTCTTGTTGAAAGCAGACAC

ACATTTAGTGCACGGCTTATTTTACCTTTCGGGTGAAAGATCAGATGTTT

TTATACCCTTCACTTGATCAATATATTTGGAAAGAATGTTTATCAAAAGT

CTATGTCACTGCTTCTACAGAAGAATGAAATTAATGCTTAGGTGATGGTA

CCTCCACCTACATCTTTTTGAGTGCATTCAATTATGTATTTTGGTTTAGC

TTCTGATTTAACATTTAATTGATTCAGTTTAAACATGTTACTTAATTAGC

AAATGTAGAGGAACCAAAAAAAGGTGAAAATAATATGTTTTGATTCAAAC

CTAAAGACATAAAAACATAAAGACATTTTAACTTTGGGTTCTCTTTAGCT

GGGATCTGGCCAGAAGGAGGCTTAAAGTTAGAAATTGCTATTATTTTAGA

ATAGGTTGGGTGGGTTGGGGGGCAAGGGTGTCTATTTGCAGCAGAGATAT

TTTGAAAAGAAGAAAATTGTTTTATATAAAAAGGAAAGCCATGACCACCT

TTCTACCTCAGATCCATCTTCATCCATTGCATTGGAAACTGCTTTATGCT

GCTGCAGTCTGCAAAGTCTAGAGCTTTTATCAGGCCATGTCATACCCAAG

AAAGCACCTATTTAAAGAAAAACAATTCCCTGAGCTCTCAACTCCAAGT

TGTAGATTTGGTGTCTTCCTTGTTCTTACTTTAAAAAGTCATGTGTTAAT

TTTTTTTCTGCCTGTATTTGTATGCAAAATGTCCTCTATCTGCTATTAAA

GAAAAGCTACGTAAAACACTACATTGTAACCTTCTAAGTAATAATAAATA

AAAAGAAATATATTGCAGTAACAATGGGAAGTAAGTATGTAGTTCTTTTG

AAATATGTGGTAAAGAACTAATCACAGACTATCATCTAATCTGGTTACAT

ATTGTATTTTTCATCCTGAATAAAAGTAATTTTAACACAAAAAAA.
```

In some embodiments, the utrophin mRNA 3'-UTR nucleic acid sequence is a homologue, variant, or functional fragment of SEQ ID NO: 13. In other embodiments, the utrophin mRNA 3'-UTR nucleic acid sequence is a homologue, variant, or functional fragment of SEQ ID NO: 56.

In mouse utrophin mRNA, the 3'-UTR has the following two miR-296-5p binding sequences: 5'-ATGGGAAAGTGGGTGGGGGCTTT-3' (SEQ ID NO: 14) and 5'-GGGTGGGTGGGTTGGGGGGCC-3' (SEQ ID NO: 23. In the mouse utrophin mRNA 3'-UTR, the miR-206 binding sequence: 5'-CCACTTTACATTATTACATTCC-3' (SEQ ID NO: 15). In the mouse utrophin mRNA 3'-UTR, the miR-150 binding sequence is: 5'-ATGGGTGGGTGGGTTGGGGG-3' (SEQ ID NO: 16). In the 3'-UTR of mouse utrophin mRNA, the miR-133b binding sequence is: 5'-GTGGGTTGGGGGGCCAA-3' (SEQ ID NO: 17). In the mouse utrophin mRNA 3'-UTR, the miR-196b binding sequence is: 5'-CCATACCCAGGAAGCACCT-3' (SEQ ID NO: 19). In of mouse utrophin mRNA 3'-UTR, the let-7c binding sequence is: 5'-AGCCATGATCACCTTTCTACCTCA-3' (SEQ ID NO: 18).

In human utrophin mRNA, the 3'-UTR has the following two miR-296-5p binding sequences: 5'-TTGGAAAGTGGGTGGGGGCTTT-3' (SEQ ID NO: 57) and 5'-ATAGGTTGGGTGGGTTGGGGGGCAAG-3' (SEQ ID NO: 58). In the human utrophin mRNA 3'-UTR, the miR-206 binding sequence is: 5'-GACCACTTTACATTTTTACATTCCT-3' (SEQ ID NO: 59). In the human utrophin mRNA 3'-UTR, the miR-150 binding sequence is: 5'-ATAGGTTGGGTGGGTTGGGGGG-3' (SEQ ID NO: 60). In the human utrophin mRNA 3'-UTR, the miR-133b binding sequence is: 5'-AGGTTGGGTGGGTTGGGGGGCAAG-3' (SEQ ID NO: 61). In the human utrophin mRNA 3'-UTR, the miR-196b binding sequence is: 5'-ATCCATTGCATTGGAAACTGCTTT-3' (SEQ ID NO: 63). In the human utrophin mRNA 3'-UTR, the let-7c binding sequence is: 5'-AGCCATGACCACCTTTCTACCTCA-3' (SEQ ID NO: 62).

In some embodiments, the muscle cell is a skeletal muscle cell, a smooth muscle cell, a satellite muscle cell, or a cardiac muscle cell.

In some embodiments, the microRNA molecule is a muscle cell specific microRNA molecule. In some embodiments, the microRNA molecule binds to utrophin mRNA. In some embodiments, the microRNA molecule is complementary to a utrophin mRNA sequence. In some embodiments, the microRNA molecule is complementary to a utrophin 5'-UTR mRNA sequence. In other embodiments, the microRNA molecule is complementary to a utrophin 3'-UTR mRNA sequence. In some embodiments, the microRNA molecule decreases utrophin protein levels. In some embodiments, the microRNA molecule decreases utrophin protein levels without decreasing utrophin mRNA levels. In some embodiments, the microRNA molecule targets utrophin-A IRES. In some embodiments, the microRNA molecule targets utrophin-A IRES in a muscle cell. In some embodiments, the microRNA molecule represses utrophin-A IRES activity.

In some embodiments, the microRNA molecule is let-7c. In some embodiments, the microRNA molecule is selected from miR-206, miR-196b, miR-133b, miR-150, or miR-296-5p.

The let-7c microRNA sequence (mouse and human) is: 5'-UGAGGUAGUAGGUUGUAUGGUU-3' (SEQ ID NO: 1). In one embodiment, a let-7c microRNA antisense sequence or anti-Let-7c is: 5'-AACCAUACAACCUAC-UACCUCA-3' (SEQ ID NO: 2).

The miR-133b microRNA sequence (mouse and human) is: 5'-UUUGGUCCCCUUCAACCAGCUA-3' (SEQ ID NO: 3). In one embodiment, a miR-133b microRNA antisense sequence or anti-miR-133b is: 5'-UAGCUG-GUUGAAGGGGACCAA-3' (SEQ ID NO: 4). The miR-150 microRNA sequence (mouse and human) is: 5'-UCUCCCAACCCUUGUACCAGUG-3' (SEQ ID NO: 5). In one embodiment, a miR-150 microRNA antisense sequence or anti-miR-150 is: 5'-CACUGGUACAAGG-GUUGGGAGA-3' (SEQ ID NO: 6). The miR-196b microRNA sequence (mouse and human) is: 5'-UAG-GUAGUUUCCUGUUGUUGGG-3' (SEQ ID NO: 7). In one embodiment, a miR-196b microRNA antisense sequence or anti-miR-196b is: 5'-CCAACAACAG-GAAACUACCUA-3' (SEQ ID NO: 8). The miR-206 microRNA sequence (mouse and human) is: 5'-UGGAAU-GUAAGGAAGUGUGUGG-3' (SEQ ID NO: 9). In one embodiment, a miR-206 microRNA antisense sequence or anti-miR-206 is: 5'-CCACACACUUCCUUACAUUCCA-3' (SEQ ID NO: 10). The miR-296-5p microRNA sequence (mouse and human) is: 5'-AGGGCCCCCCCUCAAUC-CUGU-3' (SEQ ID NO: 11). In one embodiment a miR-296-5p microRNA antisense sequence or anti-miR-296-5p is: 5'-ACAGGAUUGAGGGGGGGCCCU-3' (SEQ ID NO: 12).

In some embodiments, the microRNA molecule let-7c comprises the sequence of miRbase (www.mirbase.org) accession number MI0000064, MI0000559, MI0000560, MI0000830, MI0000831, MI0001174, MI0001866, MI0001867, MI0002445, MI0004886, MI0005124, MI0005454, MI0007138, MI0007152, MI0007183, MI0007184, MI0007574, or MI0008076.

In some embodiments, the microRNA molecule miR-206 comprises the sequence of miRBase accession number MI0000249, MI0000490, MI0000948, MI0001207, MI0002045, MI0002046, MI0002619, MI0002620, MI0004863, MI0005317, MI0007667, or MI0008002. In some embodiments, the microRNA molecule miR-196b comprises the sequence of miRBase accession number MI0001150, MI0001151, MI0001152, MI0002036, MI0003365, MI0003366, MI0004943, MI0005313, MI0007660, or MI0008016. In some embodiments, the microRNA molecule miR-133b comprises the sequence of miRBase accession number MI0000821, MI0000822, MI0001206, MI0001994, MI0003490, MI0004837, or MI0007622. In some embodiments, the microRNA molecule miR-150 comprises the sequence of miRBase accession number MI0000172, MI0000479, MI0000920, MI0002016, MI0004846, MI0005058, MI0007122, MI0007123, MI0007124, MI0007125, MI0007126, MI0007127, MI0007128, MI0007641, or MI0007998. In some embodiments, the microRNA molecule miR-296-5p comprises the sequence of miRBase accession number MI0000394, MI0000747, or MI0007681.

Utrophin upregulation is a therapeutic strategy for DMD. Normally, Utrophin-A expression is repressed through the 5' and 3'-UTRs by >98% at the translational level (FIG. 1A). The Utrophin 5' and 3'-UTRs contains microRNA target sites. Utrophin 3'-UTR exhibits its inhibitory effect both on IRES and on cap-dependent translation. Inhibition of microRNAs that target Utrophin UTRs by blocking the microRNA binding site in the mRNA or by binding to the microRNA itself are therapeutic strategies for DMD (FIG. 1B).

In some embodiments, inhibiting a microRNA molecule comprises contacting a microRNA molecule with a complementary antisense oligonucleotide sequence. In some embodiments, inhibiting a utrophin microRNA molecule comprises contacting a utrophin microRNA molecule with an utrophin microRNA antisense molecule. In some embodiments, inhibiting a utrophin microRNA molecule comprises contacting a utrophin microRNA molecule with an antisense molecule that specifically binds to or hybridizes with the utrophin microRNA.

In some embodiments, inhibiting let-7c, miR-196b, miR-133b, miR-150, miR-296-5p, miR-206, or a combination thereof leads to utrophin upregulation. In some embodiments, an inhibitor of let-7c, miR-196b, miR-133b, miR-150, miR-296-5p, miR-296, or a combination thereof is used as a Duchenne muscular dystrophy therapeutic agent.

In some embodiments, inhibiting a microRNA molecule comprises contacting a microRNA binding sequence in an mRNA with a complementary antisense oligonucleotide sequence, thereby blocking the interaction between the microRNA and its binding sequence within the mRNA. In some embodiments, inhibiting a utrophin microRNA molecule comprises contacting a microRNA binding sequence in a utrophin mRNA with a utrophin mRNA antisense molecule, thereby blocking the interaction between the microRNA and its binding sequence within the utrophin mRNA. In some embodiments, inhibiting a utrophin microRNA molecule comprises contacting a microRNA binding sequence in a utrophin mRNA with an antisense molecule that specifically binds to or hybridizes with the microRNA binding sequence, thereby blocking the interaction between the microRNA and its binding sequence within the utrophin mRNA.

In some embodiments, inhibiting a microRNA molecule comprises contacting a microRNA binding sequence within the 5'-UTR of an mRNA with a complementary antisense oligonucleotide sequence, thereby blocking the interaction between the microRNA and its binding sequence within the 5'-UTR of the mRNA. In some embodiments, inhibiting a utrophin microRNA molecule comprises contacting a microRNA binding sequence in the 5'-UTR of utrophin mRNA with an antisense molecule, thereby blocking the interaction between the microRNA and its binding sequence within the 5'-UTR of utrophin mRNA. In some embodiments, inhibiting a utrophin microRNA molecule comprises contacting the microRNA binding sequence in the 5'-UTR of utrophin mRNA with an antisense molecule that specifically binds to or hybridizes with the microRNA binding sequence, thereby blocking the interaction between the microRNA and its binding sequence within the 5'-UTR of utrophin mRNA.

In some embodiments, inhibiting a microRNA molecule comprises contacting a microRNA binding sequence within the 3'-UTR of an mRNA with a complementary antisense oligonucleotide sequence, thereby blocking the interaction between the microRNA and its binding sequence within the 3'-UTR of the mRNA. In some embodiments, inhibiting a utrophin microRNA molecule comprises contacting a microRNA binding sequence in the 3'-UTR of utrophin mRNA with an antisense molecule, thereby blocking the interaction between the microRNA and its binding sequence within the 3'-UTR of utrophin mRNA. In some embodiments, inhibiting a utrophin microRNA molecule comprises contacting the microRNA binding sequence in the 3'-UTR of utrophin mRNA with an antisense molecule that specifically binds to or hybridizes with the microRNA binding sequence, thereby blocking the interaction between the microRNA and its binding sequence within the 3'-UTR of utrophin mRNA.

In some embodiments, inhibiting interaction of a microRNA with its binding sequence in utrophin mRNA leads to utrophin upregulation. In some embodiments, inhibiting interaction of a microRNA with its binding sequence in utrophin mRNA leads to utrophin mRNA stabilization. In some embodiments, an inhibitor of the interaction of a microRNA with its binding sequence in utrophin mRNA is used as a Duchenne muscular dystrophy therapeutic agent.

In some embodiments, antisense oligonucleotides described herein contain a sequence that is complementary (in certain embodiments partially complementary, and in other embodiments exactly complementary) to a "target RNA." "Hybridization" as used herein refers to hydrogen bonding between complementary nucleotides. An oligonucleotide "specifically hybridizes" to a target polynucleotide if it hybridizes to the target under physiological conditions, with a $T_m$ substantially greater than 45° C., preferably at least 50° C., and typically 60° C.-80° C. or higher. Such hybridization preferably corresponds to stringent hybridization conditions. At a given ionic strength and pH, the $T_m$ is the temperature at which 50% of a target sequence hybridizes to a complementary polynucleotide. The degree of complementarity between an antisense oligonucleotide and its target sequence may be variable. Such hybridization may occur with "near" or "substantial" complementary of the antisense oligomer to the target sequence, as well as with exact complementarity. In some embodiments, the antisense oligonucleotide is exactly complementary to its target sequence. It is understood that it is not required that an antisense oligonucleotide be exactly complementary to its target sequence to achieve sufficient specificity, i.e. to minimize non-specific binding of the oligonucleotide to non-target sequences under the particular binding conditions being used (e.g., in vivo physiological conditions or in vitro assay conditions). "Target RNA" refers to an RNA molecule of interest, such as utrophin mRNA, which is the target for hybridizing with/binding to an oligonucleotide described herein.

In some embodiments, an antisense oligonucleotide comprises at least 3, at least 4, at least 5, at least 7, at least 9, at least 11, at least 13, or more than 13 consecutive nucleotides which are complementary to a utrophin microRNA molecule, such as a muscle cell utrophin microRNA, or a fragment thereof. In some embodiments, an antisense oligonucleotide comprises at least 3, at least 4, at least 5, at least 7, at least 9, at least 11, at least 13, or more than 13 consecutive nucleotides that are complementary to a microRNA molecule represented by a miRBase accession number as described hereinabove or a fragment thereof.

In some embodiments, an antisense oligonucleotide comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, or more than 26 consecutive nucleotides derived from the 5'-UTR or the 3'-UTR of a utrophin RNA molecule. For example, an antisense oligonucleotide derived from the 5'-UTR or the 3'-UTR of utrophin mRNA encompasses sequences that are complementary to sequences in the 5'-UTR or the 3'-UTR.

In some embodiments, an antisense oligonucleotide comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, or more than 26 consecutive nucleotides that are complementary to a utrophin microRNA, such as a muscle cell utrophin microRNA, binding site within utrophin mRNA. In some embodiments, the utrophin microRNA molecule is a microRNA represented by a miRBase accession number as described hereinabove or a fragment thereof.

In some embodiments, an antisense oligonucleotide comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, or more than 26 consecutive nucleotides complementary to the 5'-UTR or the 3'-UTR of utrophin mRNA.

A homologous complementary sequence is at least 60% homologous, at least 70% homologous, at least 80% homologous, at least 90% homologous, at least 95% homologous, at least 98% homologous, at least 99% homologous, or even 100% homologous.

In some embodiments, an antisense oligonucleotide comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, or more than 26 consecutive nucleotides complementary to let-7c (e.g., a sequence set forth in SEQ ID NO: 2).

In some embodiments, an antisense oligonucleotide comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, or more than 26 consecutive nucleotides complementary to miR-196b (e.g., a sequence set forth in SEQ ID NO: 8), to miR-133b (e.g., a sequence set forth in SEQ ID NO: 4) to miR-150 (e.g., a sequence set forth in SEQ ID NO: 6), to miR-296-5p (e.g., a sequence set forth in SEQ ID NO: 12), or to miR-206 (e.g., a sequence set forth in SEQ ID NO: 10).

In some embodiments, an antisense oligonucleotide comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, or more than 26 consecutive nucleotides complementary to a let-7c binding sequence within utrophin mRNA.

In some embodiments, an antisense oligonucleotide comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, or more than 26 consecutive nucleotides complementary to a miR-196b binding sequence, to a miR-133b binding sequence, to a miR-150 binding sequence, to a miR-296-5p binding sequence, or to a miR-206 binding sequence within a utrophin mRNA.

In some embodiments, an antisense molecule is a synthetic peptide nucleic acid (PNA) or locked nucleic acid (LNA).

In another aspect, antisense oligonucleotides are provided that inhibit binding of Let-7 microRNA to its corresponding binding site in the utrophin mRNA 3'-UTR. In some embodiments, the heteroduplex formed by the oligonucleotide and the binding sequence is resistant to cleavage by RNase H. In some embodiments, the antisense oligonucleotide has a nucleic acid sequence set forth in SEQ ID NO: 24, a fragment thereof, or a variant thereof. In some embodiments, the antisense oligonucleotide has a nucleic acid sequence set forth in SEQ ID NO: 25, a fragment thereof, or a variant thereof. In some embodiments, a variant antisense oligonucleotide of SEQ ID NO: 24 or SEQ ID NO: 25 includes oligonucleotides where one or more additional bases have been added to and/or deleted from the 3' and/or 5' end. Examples of such oligonucleotides include, for example, the nucleic acid sequences set forth in SEQ ID NOs: 26-55.

Examples of a variant antisense oligonucleotide of SEQ ID NO: 24 include, for example, the nucleic acid sequences set forth in SEQ ID NOs: 26-40. Examples of a variant antisense oligonucleotide of SEQ ID NO: 25 include, for example, nucleic acid sequences set forth in SEQ ID NOs: 41-55. The nucleic acid sequences of SEQ ID NOs: 24-55 are listed in the Table 2 below.

TABLE 2

| SEQ ID NO: | SEQUENCE | Organism |
| --- | --- | --- |
| SEQ ID NO: 24 | 5'-CUG AGG UAG AAA GGU GAU CAU GGC UC-3' | Mouse |
| SEQ ID NO: 25 | 5'-CUG AGG UAG AAA GGU GGU CAU GGC UU-3' | Human |
| SEQ ID NO: 26 | 5'-CUG AGG UAG AAA GGU GAU CAU GGC UCU-3' | Mouse |
| SEQ ID NO: 27 | 5'-CUG AGG UAG AAA GGU GAU CAU GGC UCU C-3' | Mouse |
| SEQ ID NO: 28 | 5'-CUG AGG UAG AAA GGU GAU CAU GGC UCU CC-3' | Mouse |
| SEQ ID NO: 29 | 5'-U CUG AGG UAG AAA GGU GAU CAU GGC UC-3' | Mouse |
| SEQ ID NO: 30 | 5'-UU CUG AGG UAG AAA GGU GAU CAU GGC UC-3' | Mouse |
| SEQ ID NO: 31 | 5'-GUU CUG AGG UAG AAA GGU GAU CAU GGC UC-3' | Mouse |
| SEQ ID NO: 32 | 5'-U CUG AGG UAG AAA GGU GAU CAU GGC UCU-3' | Mouse |
| SEQ ID NO: 33 | 5'-UU CUG AGG UAG AAA GGU GAU CAU GGC UCU-3' | Mouse |
| SEQ ID NO: 34 | 5'-GUU CUG AGG UAG AAA GGU GAU CAU GGC UCU-3' | Mouse |
| SEQ ID NO: 35 | 5'-U CUG AGG UAG AAA GGU GAU CAU GGC UCU C-3' | Mouse |
| SEQ ID NO: 36 | 5'-UU CUG AGG UAG AAA GGU GAU CAU GGC UCU C-3' | Mouse |
| SEQ ID NO: 37 | 5'-GUU CUG AGG UAG AAA GGU GAU CAU GGC UCU C-3' | Mouse |
| SEQ ID NO: 38 | 5'-U CUG AGG UAG AAA GGU GAU CAU GGC UCU CC-3' | Mouse |
| SEQ ID NO: 39 | 5'-UU CUG AGG UAG AAA GGU GAU CAU GGC UCU CC-3' | Mouse |
| SEQ ID NO: 40 | 5'-GUU CUG AGG UAG AAA GGU GAU CAU GGC UCU CC-3' | Mouse |
| SEQ ID NO: 41 | 5'-CUG AGG UAG AAA GGU GGU CAU GGC UUU-3' | Human |
| SEQ ID NO: 42 | 5'-CUG AGG UAG AAA GGU GGU CAU GGC UUU C-3' | Human |
| SEQ ID NO: 43 | 5'-CUG AGG UAG AAA GGU GGU CAU GGC UUU CC-3' | Human |
| SEQ ID NO: 44 | 5'-U CUG AGG UAG AAA GGU GGU CAU GGC UU-3' | Human |
| SEQ ID NO: 45 | 5'-AU CUG AGG UAG AAA GGU GGU CAU GGC UU-3' | Human |
| SEQ ID NO: 46 | 5'-GAU CUG AGG UAG AAA GGU GGU CAU GGC UU-3' | Human |
| SEQ ID NO: 47 | 5'-U CUG AGG UAG AAA GGU GGU CAU GGC UUU-3' | Human |
| SEQ ID NO: 48 | 5'-AU CUG AGG UAG AAA GGU GGU CAU GGC UUU-3' | Human |
| SEQ ID NO: 49 | 5'-GAU CUG AGG UAG AAA GGU GGU CAU GGC UUU-3' | Human |
| SEQ ID NO: 50 | 5'-U CUG AGG UAG AAA GGU GGU CAU GGC UUU C-3' | Human |
| SEQ ID NO: 51 | 5'-AU CUG AGG UAG AAA GGU GGU CAU GGC UUU C-3' | Human |

TABLE 2-continued

| SEQ ID NO: | SEQUENCE | Organism |
|---|---|---|
| SEQ ID NO: 52 | 5'-GAU CUG AGG UAG AAA GGU GGU CAU GGC UUU C-3' | Human |
| SEQ ID NO: 53 | 5'-U CUG AGG UAG AAA GGU GGU CAU GGC UUU CC-3' | Human |
| SEQ ID NO: 54 | 5'-AU CUG AGG UAG AAA GGU GGU CAU GGC UUU CC-3' | Human |
| SEQ ID NO: 55 | 5'-GAU CUG AGG UAG AAA GGU GGU CAU GGC UUU CC-3' | Human |

In some embodiments, the antisense oligonucleotide comprises a sequence of at least 18, at least 19, at least 20, at least 21, at least 22, at least 23, at least 24, or at least 25 consecutive nucleotides of a nucleic acid sequence set forth in SEQ ID NOs: 24-55.

In another aspect, provided herein are compositions that comprise an antisense oligonucleotide described herein, wherein the oligonucleotide is present in an amount effective to inhibit the binding of Let-7 microRNA to its corresponding binding site in the 3'-UTR in utrophin mRNA. In some embodiments, these compositions further comprise at least one suitable excipient, for example, a pharmaceutically acceptable excipient, or an additive, known in the art.

"Nucleoside" refers to a base (e.g., a purine [e.g. A and G] or pyrimidine [e.g., C, 5-methyl-C, T and U]) combined with a sugar (e.g., [deoxy]ribose, arabinose and derivatives). "Nucleotide" refers to a nucleoside having a phosphate group attached to its sugar moiety. In embodiments these structures may include various modifications, e.g. either in the base, sugar and/or phosphate moieties. "Modified nucleotide/nucleoside" as used herein refers to a nucleotide/nucleoside that differs from the native form. "Oligonucleotide" as used herein refers to a sequence comprising a plurality of nucleotides joined together. An oligonucleotide may comprise modified structures in its backbone structure and/or in one or more of its component nucleotides. In some embodiments, the oligonucleotides are about 8 to 200 bases in length, in further embodiments from about 8 to about 50 bases, from about 8 to about 40 bases, from about 8 to about 32 bases and yet further embodiments, from about 12 to about 32 or from about 12 to about 25 bases in length. In some embodiments, the oligonucleotides are about 12 to about 50 bases in length, from about 12 to about 40 bases, and yet further embodiments, from about 12 to about 25 bases in length. In some embodiments, the oligonucleotides are about 14 to about 50 bases, from about 14 to about 40 bases, from about 14 to about 32, or from about 14 to about 25 bases in length. In some embodiments, the oligonucleotides are about 15 to about 50 bases, from about 15 to about 40 bases, from about 15 to about 32, or from about 15 to about 25 bases in length. In some embodiments, the oligonucleotides are about 16 to about 50 bases, from about 16 to about 40 bases, from about 16 to about 32, or from about 16 to about 25 bases in length. In some embodiments, the oligonucleotides are about 18 to about 50 bases, from about 18 to about 40 bases, from about 18 to about 32, or from about 18 to about 25 bases in length. In some embodiments, the oligonucleotides are about 20 to about 50 bases, from about 20 to about 40 bases, from about 20 to about 32, or from about 20 to about 25 bases in length. In some embodiments, the oligonucleotides are 18 bases in length. In some embodiments, the oligonucleotides are 19 bases in length. In some embodiments, the oligonucleotides are 20 bases in length. In some embodiments, the oligonucleotides are 21 bases in length. In some embodiments, the oligonucleotides are 22 bases in length. In some embodiments, the oligonucleotides are 23 bases in length. In some embodiments, the oligonucleotides are 24 bases in length. In some embodiments, the oligonucleotides are 25 bases in length. In some embodiments, the oligonucleotides are 26 bases in length. In some embodiments, the oligonucleotides are 27 bases in length. In some embodiments, the oligonucleotides are 28 bases in length.

"Alkyl" refers to straight and branched chain saturated hydrocarbon groups (e.g., methyl, ethyl, propyl, butyl, isopropyl, etc.). "Alkenyl" and "alkynyl" refer to hydrocarbon groups having at least one C—C double and one C—C triple bond, respectively. "Alkoxy" refers to an —O-alkyl structure. "Alkylamino" refers to —NH(alkyl) or —N(alkyl)$_2$ structures. "Aryl" refers to substituted and unsubstituted aromatic cyclic structures (e.g., phenyl, naphthyl, anthracyl, phenanthryl, pyrenyl, and xylyl groups). "Hetero" refers to an atom other than C; including but not limited to N, O, or S. In some embodiments, the above-mentioned groups may be substituted.

"Sugar-modified nucleoside" or "sugar-modified nucleotide" as used herein refers to a nucleoside or nucleotide, respectively, which has a different or modified sugar structure as compared to the sugar moiety of a native deoxyribonucleoside or deoxyribonucleotide, respectively, or ribonucleoside or ribonucleotide, respectively. Such modifications include but are not limited to changes in conformation of the sugar ring, substitution or addition of different ring structures, and the modification (substitution, deletion or addition) of any sugar ring substituents. A sugar-modified nucleoside or nucleotide may be capable of adopting a DNA-like conformation. A "DNA-like conformation" as used herein refers to the sugar structure of the nucleoside or nucleotide, and refers to a conformation which resembles the conformation of a native 2'-deoxyribonucleoside or 2'-deoxyribonucleotide, i.e. one whose sugar residue is capable of adopting a C2'-endo (south pucker) and/or O4'-endo (east pucker) conformation. As arabinonucleotides may adopt such a C2'-endo (south pucker) and/or O4'-endo (east pucker) conformation, arabinonucleic acids and DNA exhibit similar conformational preferences (Venkateswarlu et al., *J. Am. Chem. Soc.* 1999, 121:5609; Trempe et al., *J. Am. Chem. Soc.* 2001, 123:4896; Denisov et al., *Nucleic Acids Res.* 2001, 29:4284). Other DNA-like nucleotides include, but are not limited to, alpha-L-LNA (Petersen et al., *J. Am. Chem. Soc.* 2001; 123:7431) and cyclohexene nucleic acids (Wang et al., *J. Am. Chem. Soc.*, 2000, 122:8595).

In some embodiments, the phosphate backbone modification comprises sugar-modified oligonucleotides. In some embodiments, sugar-modified oligonucleotides comprise β-D-arabinonucleotides (i.e., ANA oligomers) and 2'-deoxy-2'-fluoro-β-D-arabinonucleosides (i.e., 2'F-ANA oligomers). In a preferred embodiment, sugar-modified oligonucleotides comprise 2'F-ANA oligomers.

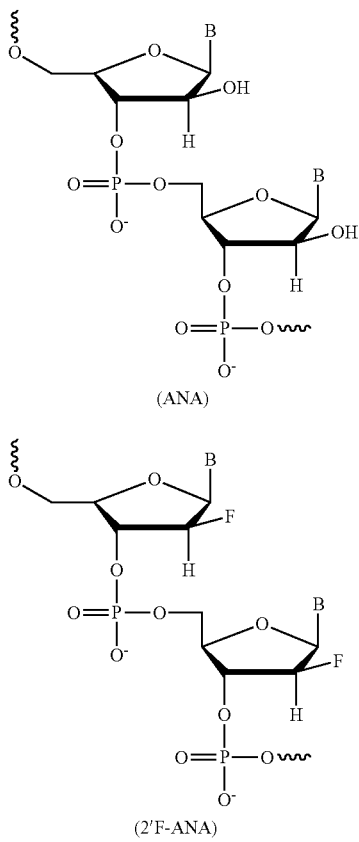

(ANA)

(2'F-ANA)

Without wishing to be bound by theory, it is believed that oligonucleotides that are sugar-modified with ANA and 2'-F ANA display increased resistance to action of degradative nucleases present in serum. When an antisense oligonucleotide forms a duplex with its target miRNA binding sequence in the 3'-UTR utrophin mRNA, for example with a Let-7 microRNA binding sequence, it blocks the binding of Let-7 microRNA with its corresponding binding sequence. This results in stabilization of utrophin mRNA, leading to enhanced utrophin production, and thereby treating Duchenne Muscular Dystrophy (DMD).

In some embodiments, the antisense oligonucleotide is a phosphorothioate molecule. In some embodiments, the antisense oligonucleotide is a 2'-O-methyl phosphorothioate oligoribonucleotide molecule. Phosphorothioate molecules are known in the art. These molecules include a phosphorothioate (PS) bond, which substitutes a sulfur atom for a non-bridging oxygen in the phosphate backbone of an oligo. This modification renders the internucleotide linkage resistant to nuclease degradation.

In some embodiments, the 2'-substituent, e.g., of the arabinose sugar in ANA residues, includes but is not limited to fluorine, hydroxyl, amino, cyano, azido, —CH=CH$_2$, —C≡CH, alkyl (e.g., lower alkyl [e.g., C$_1$-C$_9$ alkyl] e.g., methyl, ethyl, propyl, etc.), alkoxy (e.g., lower alkoxy, [e.g., C$_1$-C$_9$ alkoxy] e.g., methoxy, ethoxy, propoxy, etc.) and functionalized alkyl (e.g., functionalized lower alkyl, e.g. 2'-CF$_3$), alkoxy, and alkoxyalkyl (e.g. methoxyethyl, ethoxyethyl, etc.) groups. In an embodiment, the functionalized alkyl group is selected from the group consisting of methylamino, ethylamino and propylamino groups. In some embodiments, the functionalized alkoxy group is —O(CH$_2$)$_q$—R, wherein q=2, 3 or 4 and —R is selected from the group consisting of —NH$_2$, —OCH$_3$, and —OCH$_2$CH$_3$ groups.

In some embodiments, the 2' substituent of the arabinose sugar is fluorine, i.e., the arabinonucleotide is a 2'-fluoroarabinonucleotide (2'F-ANA; also abbreviated "FANA").

In some embodiments, the oligonucleoside comprises an internucleoside linkage comprising a phosphate, thereby being an oligonucleotide. In some embodiments, the sugar-modified nucleosides and/or 2'-deoxynucleosides comprise a phosphate, thereby being sugar-modified nucleotides and/or 2'-deoxynucleotides. In some embodiments, the oligonucleoside comprises an internucleoside linkage comprising a phosphorothioate. In some embodiments, the internucleoside linkage is selected from phosphorothioate, phosphorodithioate, methylphosphorothioate, Rp-phosphorothioate, Sp-phosphorothioate. In some embodiments, the oligonucleotide comprises one or more internucleotide linkages selected from the group consisting of: (a) phosphodiester; (b) phosphotriester; (c) phosphorothioate; (d) phosphorodithioate; (e) Rp-phosphorothioate; (f) Sp-phosphorothioate; (g) boranophosphate; (h) methylene (methylimino) (3'CH$_2$—N(CH$_3$)—O5'); (i) 3'-thioformacetal (3'-S—CH$_2$—O5'); (j) amide (3'CH$_2$—C(O)NH-5'); (k) methylphosphonate; (l) phosphoramidate (3'-OP(O$_2$)—N5'); and (m) any combination of (a) to (l).

In one aspect, provided herein are oligonucleotides comprising alternating segments or units of sugar-modified nucleotides (e.g., arabinonucleotide analogues [e.g., FANA]) and 2'-deoxyribonucleotides (DNA). In some embodiments, the oligonucleotide comprises at least 2 of each of sugar-modified nucleotide and 2'-deoxynucleotide segments, thereby having at least 4 alternating segments overall. Each alternating segment or unit may independently contain 1 or a plurality of nucleotides. In some embodiments, each alternating segment or unit may independently contain 1 or 2 nucleotides. In some embodiments, the segments each comprise 1 nucleotide. In some embodiments, the segments each comprise 2 nucleotides. In some embodiments, the plurality of nucleotides may consist of 2, 3, 4, 5 or 6 nucleotides. The oligonucleotide may contain an odd or even number of alternating segments or units. The oligonucleotide may commence and/or terminate with a segment containing sugar-modified nucleotide residues or DNA residues. Accordingly, in some embodiments, the oligonucleotides may be represented as follows:

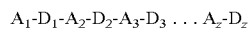

Where each of $A_1$, $A_2$, etc. represents a unit of one or more (e.g., 1 or 2) sugar-modified nucleotide residues (e.g., ANA or FANA) and each of $D_1$, $D_2$, etc. represents a unit of one or more (e.g., 1 or 2) DNA residues. The number of residues within each unit may be the same or variable from one unit to another. The oligonucleotide may have an odd or an even number of units. The oligonucleotide may start (i.e. at its 5' end) with either a sugar-modified nucleotide-containing unit (e.g., an ANA-containing unit or a FANA-containing unit) or a DNA-containing unit. The oligonucleotide may terminate (i.e. at its 3' end) with either a sugar-modified nucleotide-containing unit or a DNA-containing unit. The total number of units may be as few as 4 (i.e. at least 2 of each type).

In some embodiments, the oligonucleotides comprise alternating segments or units of arabinonucleotides and 2'-deoxynucleotides, wherein said segments or units each independently comprise at least one arabinonucleotide or 2'-deoxynucleotide, respectively. In some embodiments, the segments each independently comprise 1 to 2 arabinonucleotides or 2'-deoxynucleotides. In some embodiments, the segments each independently comprise 2 to 5 or 3 to 4 arabinonucleotides or 2'-deoxynucleotides. In some embodiments, the oligonucleotides comprise alternating segments or units of arabinonucleotides and 2'-deoxynucleotides, wherein said segments or units each comprise one arabinonucleotide or 2'-deoxynucleotide, respectively. In some embodiments, the segments each independently comprise about 3 arabinonucleotides or 2'-deoxynucleotides. In some embodiments, the oligonucleotides comprise alternating segments or units of arabinonucleotides and 2'-deoxynucleotides, wherein said segments or units each comprise one arabinonucleotide or 2'-deoxynucleotide, respectively. In some embodiments, the oligonucleotides comprise alternating segments or units of arabinonucleotides and 2'-deoxynucleotides, wherein said segments or units each comprise two arabinonucleotides or 2'-deoxynucleotides, respectively.

In some embodiments, the above-mentioned oligonucleotide has a structure selected from the group consisting of:

a) $(A_x-D_y)_n$     I b) $(D_y-A_x)_n$     II c) $(A_x-D_y)_m-A_x-D_y-A_x$     III d) $(D_y-A_x)_m-D_y-A_x-D_y$     IV wherein each of m, x and y are each independently an integer greater than or equal to 1, n is an integer greater than or equal to 2, A is a sugar-modified nucleotide and D is a 2'-deoxyribonucleotide.

For example, the above-mentioned oligonucleotide has structure I wherein x=1, y=1 and n=10, thereby having a structure:

A-D-A-D-A-D-A-D-A-D-A-D-A-D-A-D-A-D-A-D.

In another example, the above-mentioned oligonucleotide has structure II wherein x=1, y=1 and n=10, thereby having a structure:

D-A-D-A-D-A-D-A-D-A-D-A-D-A-D-A-D-A-D-A.

In another example, the above-mentioned oligonucleotide has structure III wherein x=1, y=1 and n=9, thereby having a structure:

A-D-A-D-A-D-A-D-A-D-A-D-A-D-A-D-A-D-A.

In another example, the above-mentioned oligonucleotide has structure IV wherein x=1, y=1 and n=9, thereby having a structure:

D-A-D-A-D-A-D-A-D-A-D-A-D-A-D-A-D-A-D.

In another example, the above-mentioned oligonucleotide has structure I wherein x=2, y=2 and n=5, thereby having a structure:

A-A-D-D-A-A-D-D-A-A-D-D-A-A-D-D-A-A-D-D.

In another example, the above-mentioned oligonucleotide has structure II wherein x=2, y=2 and n=5, thereby having a structure:

D-D-A-A-D-D-A-A-D-D-A-A-D-D-A-A-D-D-A-A.

In another example, the above-mentioned oligonucleotide has structure III wherein x=2, y=2 and m=4, thereby having a structure:

A-A-D-D-A-A-D-D-A-A-D-D-A-A-D-D-A-A.

In another example, the above-mentioned oligonucleotide has structure IV wherein x=2, y=2 and m=4, thereby having a structure:

D-D-A-A-D-D-A-A-D-D-A-A-D-D-A-A-D-D.

In some embodiments, the oligonucleoside further comprises a third segment comprising a modified nucleoside, wherein said third segment is adjacent to (a) the 5' end of said alternating segments, (b) the 3' end of said alternating segments, or (c) both (a) and (b). In some embodiments, the oligonucleotide further comprises a third segment comprising a modified nucleotide, wherein said third segment is adjacent to (a) the 5' end of said alternating segments, (b) the 3' end of said alternating segments, or (c) both (a) and (b). In some embodiments, the modified nucleotide is a modified ribonucleotide. In some embodiments, the modified ribonucleotide has a modification at its 2' position. For example, the 2' modification is selected from the group consisting of methoxy (2'-O-Me-RNA), methoxyethyl (2'-MOE-RNA), fluoro and propylamino groups.

In some embodiments, the antisense oligonucleotide is a morpholino or phosphorodiamidate morpholino oligonucleotide (PMO) or Vivo-morpholino molecule. Morpholinos and PMOs are known in the art and are synthetic molecules that are the product of a redesign of natural nucleic acid structure. See, e.g., Summerton et al., "Morpholino Antisense Oligomers: Design, Preparation and Properties". *Antisense & Nucleic Acid Drug Development* 7 (3): 187-95. PMOs can bind to complementary sequences by standard nucleic acid base-pairing. The structural difference between morpholinos and DNA is that, while morpholinos have standard nucleic acid bases, those bases are bound to morpholine rings instead of deoxyribose rings. In addition, PMOs are linked through phosphorodiamidate groups instead of phosphates. Replacement of the anionic phosphates with the uncharged phosphorodiamidate groups eliminates ionization in the usual physiological pH range, and thus morpholinos in organisms or cells are uncharged molecules. Vivo-Morpholinos are comprised of a Morpholino oligonucleotide with a unique covalently linked delivery moiety that is comprised of an octa-guanidine dendrimer.

The antisense oligonucleotide may be made by a suitable method known in the art. For example, the antisense oligonucleotide is produced by a chemical process, for example by the chemical phosphoamidite method comprising sulfuration with tetraethylthiuram disulfide in acetonitrile (*Tetrahedron Lett.*, 1991, 32, 3005-3008, see also US2009/0105467; each of which is herein incorporated by reference in its entirety). In some embodiments, the antisense nucleic acid is an oligoribonucleotide molecule, for example, β-D-arabinonucleotide molecule, a 2'-deoxy-2'-fluoro-β-D-arabinonucleoside molecule, or a 2'-O-methyl oligoribonucleotides molecule.

In some embodiments, the synthetic antisense oligonucleotide further comprises a backbone of stabilized internucleotide linkages. A "stabilized internucleotide linkage" means an internucleotide linkage that is relatively resistant to in vivo degradation (e.g., via an exo- or endo-nuclease), compared to a phosphodiester internucleotide linkage. Preferred stabilized internucleotide linkages include, without limitation, phosphorothioate, phosphorodithioate, methylphosphonate, methylphosphorothioate, phosphonoacetate, Rp-phosphorothioate, Sp-phosphorothioate, boranophosphate, or 3'-thioformacetal, or combinations thereof.

In embodiments, DNA residues may contain any of the bases selected amongst adenine (A), cytosine (C), guanine (G) or thymine (T) or versions comprising modifications of the nucleotide base or backbone structures. In embodiments, ANA residues may contain any of the bases selected amongst adenine (A), inosine (I), 2,6-diaminopurine (2,6-DAP), cytosine (C), 5-methylcytosine (5 meC), guanine (G) or thymine (T) or uracil (U).

Oligonucleotides may also include species which include at least one modified nucleotide base. Thus, purines and pyrimidines other than those normally found in nature may be used. As noted above, a nucleotide of the sugar-modified nucleotide segment (e.g. ANA segment) may comprise modifications on its pentofuranosyl portion. Examples of such modifications are 2'-O-alkyl- and 2'-halogen-substituted nucleotides. Some specific examples of modifications at the 2' position of sugar moieties which are useful in the present invention are OH, SH, SCH$_3$, F, OCN, O(CH$_2$)$_n$NH$_2$ or O(CH$_2$)$_n$CH$_3$ where n is from 1 to about 10; C$_1$ to C$_{10}$ lower alkyl, substituted lower alkyl, alkaryl or aralkyl; Cl; Br; CN; CF$_3$; OCF$_3$; O—, S—, or N-alkyl; O—, S—, or N-alkenyl; SOCH$_3$; SO$_2$CH$_3$; ONO$_2$; NO$_2$; N$_3$; NH$_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. One or more pentofuranosyl groups of the nucleotide of the sugar-modified nucleotide segment may be replaced by another sugar, by a sugar mimic such as cyclobutyl or by another moiety which takes the place of the sugar.

In some embodiments, provided herein are methods for treating a muscle disease in a subject, the methods comprising the step of administering to said subject a composition for inhibiting a utrophin microRNA molecule. In some embodiments, provided herein are methods for treating or reducing the signs and symptoms associated with muscular dystrophy in a subject, the methods comprising the step of administering to said subject a composition for inhibiting a utrophin microRNA molecule. In some embodiments, translation of utrophin in a muscle cell in the subject is increased over basal levels by about 10%, 20%, 25%, 30%, 40%, 50%, 60%, 70%, 75%, 80%, 90% or more. In some embodiments, translation of utrophin in a muscle cell in the subject is increased over basal levels by about 2-fold, 3-fold, 4-fold, 5-fold, 10-fold, 20-fold, 25-fold, 30-fold, 40-fold, 50-fold, 75-fold, 100-fold or more.

Muscular dystrophy may refer to any type of muscular dystrophy. For example, the muscular dystrophy is Duchenne Muscular Dystrophy (DMD). In another example, the muscular dystrophy is Becker Muscular Dystrophy (BMD).

In some embodiments, such compositions include an oligonucleotide described herein in a therapeutically or prophylactically effective amount sufficient to treat or prevent the muscle disease or muscular dystrophy, and a pharmaceutically acceptable carrier.

A "therapeutically effective amount" refers to an amount effective, at dosages and for periods of time necessary, to achieve the desired therapeutic result, such as a decrease in or a prevention of the expression or translation of a particular target nucleic acid, such as utrophin mRNA. A therapeutically effective amount of an oligonucleotide described herein may vary according to factors such as the disease state, age, sex, and weight of the individual, and the ability of the oligonucleotide to elicit a desired response in the individual. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as preventing or treating a disease. A prophylactically effective amount can be determined as described above for the therapeutically effective amount. For a particular subject, specific dosage regimens may be adjusted over time according to the individual need and the professional judgement of the person administering or supervising the administration of the compositions.

As used herein "pharmaceutically acceptable carrier" or "excipient" includes solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions described herein is contemplated. Supplementary active compounds can also be incorporated into the compositions.

Therapeutic compositions typically are sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, mono stearate salts and gelatin. Moreover, an oligonucleotide described herein can be administered in a time release formulation, for example in a composition which includes a slow release polymer. The oligonucleotide can be prepared with carriers that will protect it against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating an active compound, such as an oligonucleotide described herein, in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. In some embodiments, an oligonucleotide described herein may be formulated with one or more additional compounds that enhance its solubility.

The terms "treatment" or "treating," as used herein, refers to any treatment of a disease in a mammal and includes: (1) preventing the disease from occurring in a mammal which may be predisposed to the disease but does not yet experience or display symptoms of the disease; e.g. prevention of the outbreak of the clinical symptoms; (2) inhibiting the disease, e.g., arresting its development; or (3) relieving the disease, e.g., causing regression of the symptoms of the disease.

The term "subject," as used herein, includes any human or non-human animal. The term "non-human animal" includes all vertebrates, e.g., mammals and non-mammals, such as non-human primates, sheep, dog, cow, chickens, amphibians, reptiles, etc. The method of treatment described herein can be used to treat a suitable mammal, preferably a human.

In another aspect, provided herein are methods of treating or reducing the signs and symptoms associated with Duchene muscular dystrophy (DMD) in a subject, by administering to the subject a composition for inhibiting a utrophin microRNA molecule. In some embodiments, provided herein are methods of treating or reducing the signs and symptoms associated with Becker muscular dystrophy (BMD) in a subject, by administering to the subject a composition for inhibiting a utrophin microRNA molecule.

In another aspect, provided herein are compositions comprising an effective amount of an agent that inhibits utrophin microRNA molecule. In an exemplary embodiment, the agent comprises a let-7c miRNA antisense oligonucleotide (e.g., a sequence set forth in SEQ ID NO: 2), a miR-133b miRNA antisense oligonucleotide (e.g., a sequence set forth in SEQ ID NO: 4), a miR-150 miRNA antisense oligonucleotide (e.g., a sequence set forth in SEQ ID NO: 6), a miR-196b miRNA antisense oligonucleotide (e.g., a sequence set forth in SEQ ID NO: 8), a miR-206 miRNA antisense oligonucleotide (e.g., a sequence set forth in SEQ ID NO: 10), or a miR-296-5p miRNA antisense oligonucleotide (e.g., a sequence set forth in SEQ ID NO: 12).

In some embodiments, the methods comprise administering compositions where the active compound is the sole active ingredient in the composition. However, also contemplated are methods for treating diseases and disorders that comprise administering compositions comprising multiple active compounds.

In some embodiments, provided herein are compositions comprising an effective amount of an agent that blocks interaction or binding between a utrophin microRNA molecule and its binding sequence within utrophin mRNA. In an exemplary embodiment, the agent comprises a let-7c miRNA binding sequence antisense oligonucleotide (e.g., a sequence set forth in SEQ ID NOs: 24-55 or SEQ ID NOs: 64-75).

In one embodiment, an active ingredient of compositions described herein is a single let-7c miRNA binding sequence antisense oligonucleotide (e.g., an oligonucleotide with a sequence selected from SEQ ID NOs: 24-55 or SEQ ID NOs: 64-75). In some embodiments, the active ingredients of compositions described herein comprise more than one let-7c miRNA binding sequence antisense oligonucleotide (e.g., a set of oligonucleotides with sequences selected from SEQ ID NOs: 24-55 or SEQ ID NOs: 64-75). In some embodiments, the active ingredients of compositions described herein comprise two, three, four, or five let-7c miRNA binding sequence antisense oligonucleotides (e.g., two, three, four, or five oligonucleotides with sequences selected from SEQ ID NOs: 24-55 or SEQ ID NOs: 64-75). In some embodiments, the active ingredients of compositions described herein comprise more than five let-7c miRNA binding sequence antisense oligonucleotides (e.g., a set of oligonucleotides with sequences selected from SEQ ID NOs: 24-55 and SEQ ID NOs: 64-75).

In one embodiment, the active ingredients of compositions described herein comprise one or more let-7c miRNA binding sequence antisense oligonucleotides (e.g., oligonucleotides with sequences selected from SEQ ID NOs: 24-55 or SEQ ID NOs: 64-75) and at least one additional miRNA antisense oligonucleotide, e.g., a miR-133b antisense oligonucleotide (e.g., a sequence set forth in SEQ ID NO: 4), a miR-150 antisense oligonucleotide (e.g., a sequence set forth in SEQ ID NO: 6), a miR-196b antisense oligonucleotide (e.g., a sequence set forth in SEQ ID NO: 8), a miR-206 antisense oligonucleotide (e.g., a sequence set forth in SEQ ID NO: 10), or a miR-296-5p antisense oligonucleotide (e.g., a sequence set forth in SEQ ID NO: 12).

In some embodiments, the active ingredients of compositions described herein comprise one or more let-7c miRNA binding sequence antisense oligonucleotides (e.g., oligonucleotides with sequences selected from SEQ ID NOs: 24-55 or SEQ ID NOs: 64-75) and one additional miRNA antisense molecule. In some embodiments, the active ingredients of compositions described herein comprise one or more let-7c miRNA binding sequence antisense molecules (e.g., oligonucleotides with sequences selected from SEQ ID NOs: 24-55 or SEQ ID NOs: 64-75) and two, three, four, or five additional miRNA antisense molecules. In some embodiments, the active ingredients of compositions described herein comprise one or more let-7c miRNA binding sequence antisense molecules (e.g., oligonucleotides with sequences selected from SEQ ID NOs: 24-55 or SEQ ID NOs: 64-75) and more than five additional miRNA antisense molecules.

In one embodiment, at least one miRNA binding sequence antisense oligonucleotide in the compositions described herein comprises one or more arabinonucleotides. In some embodiments, at least one miRNA binding sequence antisense oligonucleotides in the compositions described herein comprises 2'F-ANA. In a preferred embodiment, the let-7c miRNA binding sequence antisense oligonucleotide in the compositions described herein comprise ANA or 2'F-ANA. In some embodiments, all the miRNA binding sequence antisense oligonucleotides in the compositions described herein comprise ANA or 2'F-ANA.

In one embodiment, one or more let-7c miRNA binding sequence antisense oligonucleotides in the compositions described herein comprise ANA or 2'F-ANA, while at least one of the remaining let-7c miRNA binding sequence antisense oligonucleotides are 2'-O-methyl phosphorothioate oligoribonucleotides, morpholino oligoribonucleotides, phosphorodiamidate morpholino oligoribonucleotides or a combination thereof. In some embodiments, one or more let-7c miRNA binding sequence antisense oligonucleotides in the compositions described herein comprise ANA or 2'F-ANA, while at least one of the additional miRNA antisense oligonucleotides (e.g., a miR-133b miRNA antisense oligonucleotide (e.g., a sequence set forth in SEQ ID NO: 4), a miR-150 miRNA antisense oligonucleotide (e.g., a sequence set forth in SEQ ID NO: 6), a miR-196b miRNA antisense oligonucleotide (e.g., a sequence set forth in SEQ ID NO: 8), a miR-206 miRNA antisense oligonucleotide (e.g., a sequence set forth in SEQ ID NO: 10), or a miR-296-5p miRNA antisense oligonucleotide (e.g., a sequence set forth in SEQ ID NO: 12)) comprise ANA, 2'F-ANA, 2'-O-methyl phosphorothioate, morpholino, phosphorodiamidate morpholino, or a combination thereof.

Also encompassed are methods for treating diseases and disorders that comprise administering an active compound described herein in combination with one or more other therapeutic agents appropriate for the disease or disorder that is being treated, as is known in the art. These agents include, but are not limited to, drugs for treating DMD or BMD.

In some embodiments, a composition for inhibiting a utrophin microRNA molecule also induces utrophin protein production. A utrophin microRNA molecule is a microRNA molecule which binds the 5' or 3'-UTR of utrophin mRNA and inhibits utrophin protein production.

In some embodiments, administering a composition for inhibiting a utrophin microRNA molecule comprises contacting the microRNA molecule with a utrophin microRNA antisense oligonucleotide. In some embodiments, a composition for inhibiting a utrophin microRNA molecule comprises a utrophin microRNA antisense oligonucleotide. In some embodiments, a composition for inhibiting a muscle cell specific microRNA molecule comprises a muscle cell specific utrophin microRNA antisense oligonucleotide.

In some embodiments, administering a composition for inhibiting a utrophin microRNA molecule comprises contacting utrophin mRNA with an oligonucleotide complementary to the microRNA binding sequence within utrophin mRNA. In some embodiments, a composition for inhibiting a utrophin microRNA molecule comprises an oligonucleotide complementary to the microRNA binding sequence within utrophin mRNA. In some embodiments, a composition for inhibiting a muscle cell specific microRNA molecule comprises an oligonucleotide complementary to a muscle cell specific microRNA binding sequence within utrophin mRNA.

In some embodiments, a composition for inhibiting a utrophin microRNA molecule is administered to a muscle cell in a subject. In some embodiments, a composition for inhibiting utrophin microRNA molecule is administered to a subject and is targeted to a muscle cell.

In some embodiments, methods described herein reduce signs and symptoms associated with Duchenne muscular dystrophy (DMD) or Becker muscular dystrophy (BMD). In some embodiments, methods described herein improve walking of a DMD or BMD patient. In some embodiments, methods described herein reduce or inhibit calves swelling with fibrous tissue. In some embodiments, methods described herein induce muscle growth. In some embodiments, methods described herein induce muscle regeneration. In some embodiments, methods described herein reduce or inhibit contractures. In some embodiments, methods described herein reduce or inhibit scoliosis. In some embodiments, methods described herein reduce or inhibit diaphragm weakening. In some embodiments, methods described herein reduce or inhibit a cardiac disease caused by or associated with lack of dystrophin.

The oligonucleotides described herein and pharmaceutical compositions comprising them can be administered to a subject by any suitable method known in the art. In some embodiments, administration is systemic. In some embodiments, administration is intramuscular. In some embodiments, administration of the nucleic acids described herein is gymnotic.

In some embodiments of methods and compositions described herein, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In some embodiments, the active ingredient is formulated in a capsule. In accordance with this embodiment, the compositions comprise, in addition to the active compound (e.g. the mimetic compound, peptide or nucleotide molecule) and the inert carrier or diluent, a hard gelatin capsule.

In some embodiments, the pharmaceutical compositions are administered by intravenous, intra-arterial, or intramuscular injection of a liquid preparation. Suitable liquid formulations include solutions, suspensions, dispersions, emulsions, oils and the like. In some embodiments, the pharmaceutical compositions are administered intravenously and are thus formulated in a form suitable for intravenous administration. In some embodiments, the pharmaceutical compositions are administered intra-arterially and are thus formulated in a form suitable for intra-arterial administration. In some embodiments, the pharmaceutical compositions are administered intramuscularly and are thus formulated in a form suitable for intra-muscular administration.

In some embodiments, the pharmaceutical compositions are administered topically to body surfaces and are thus formulated in a form suitable for topical administration. Topical formulations include gels, ointments, creams, lotions, drops and the like.

In some embodiments, the pharmaceutical composition is administered as a suppository, for example a rectal suppository or a urethral suppository. In some embodiments, the pharmaceutical composition is administered by subcutaneous implantation of a pellet. In some embodiments, the pellet provides for controlled release of active agent over a period of time.

In some embodiments, the active compound is delivered in a vesicle, e.g., a liposome.

In other embodiments, carriers or diluents used in the compositions described herein include, but are not limited to, a gum, a starch (e.g., corn starch, pregeletanized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof.

In other embodiments, pharmaceutically acceptable carriers for liquid formulations are aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

In some embodiments, parenteral vehicles (for subcutaneous, intravenous, intra-arterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

In other embodiments, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents(e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

In some embodiments, the pharmaceutical compositions provided herein are controlled-release compositions, i.e. compositions in which the active compound is released over a period of time after administration. Controlled- or sustained-release compositions include formulation in lipophilic depots (e.g. fatty acids, waxes, oils). In some embodiments, the composition is an immediate-release composition, i.e. a composition in which of the active compound is released immediately after administration.

In some embodiments, the pharmaceutical composition is delivered in a controlled release system. For example, the agent may be administered using intravenous infusion, an implantable osmotic pump, a transdermal patch, liposomes, or other modes of administration. In one embodiment, a pump may be used. In some embodiments, polymeric materials are used; e.g. in microspheres in or an implant. In yet some embodiments, a controlled release system is placed in proximity to the target cell, thus requiring only a fraction of the systemic dose.

The compositions also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also included are particulate compositions coated with polymers (e.g. poloxamers or poloxamines) and the compound coupled to antibodies directed against tissue-specific receptors, ligands or antigens or coupled to ligands of tissue-specific receptors.

Also contemplated are compounds modified by covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. Modified compounds are known to exhibit substantially longer half-lives in blood following intravenous injection than do the corresponding unmodified compounds. Such modifications may also increase the compound's solubility in aqueous solution, eliminate aggregation, enhance the physical and chemical stability of the compound, and reduce the immunogenicity and reactivity of the compound. As a result, a desired in vivo biological activity may be achieved by administration of such polymer-compound abducts less frequently or in lower doses than with the unmodified compound.

In another aspect, provided herein are commercial packages comprising an oligonucleotide described herein. In some embodiments, the commercial package further comprises instructions for use of the oligonucleotide.

In another aspect, provided herein are uses of an oligonucleotide described herein for treating or reducing the signs and symptoms associated with a muscle disease, myopathy or muscular dystrophy (e.g., DMD or BMD) in a subject, or for enhancing or upregulating utrophin. In another aspect, provided herein are uses of an oligonucleotide described herein for the preparation of a medicament for treating or reducing the signs and symptoms associated with a muscle disease, myopathy or muscular dystrophy (e.g., DMD or BMD) in a subject, or for enhancing or upregulating utrophin in a subject.

The following examples are presented in order to more fully illustrate the preferred embodiments of the invention. They should in no way be construed, however, as limiting the broad scope of the invention.

EXAMPLES

Example 1: Utrophin-A is Translated Inefficiently

Figure 3A:
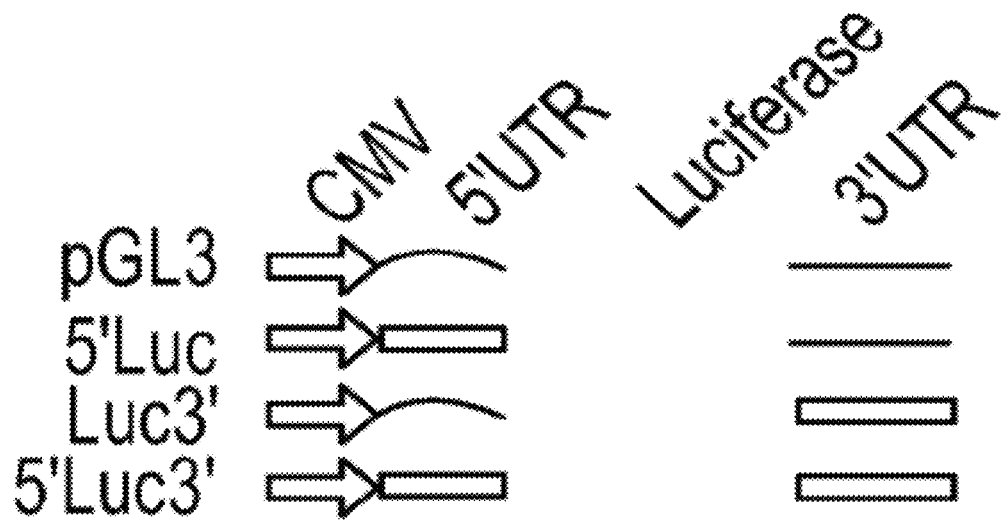
FIG. 3 shows that Utrophin 3'-UTR represses IRES. (A) is a schematic representation of utrophin-A mRNA. 3 bicistronic constructs comprising control, utrophin IRES or utrophin IRES plus utrophin 3'-UTR. (B) A bar graph showing the ratio of expression from the two cistrons, under the control of the 3 different constructs.
Figure 3B:
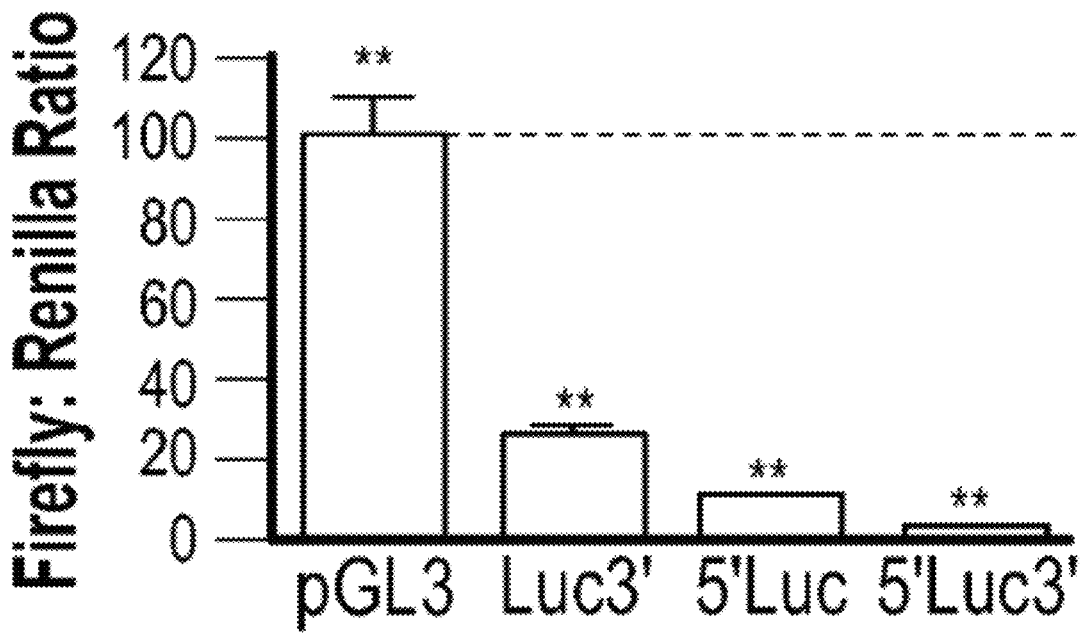

Ribosomal profiling of utrophin-A mRNA in C2C12 muscle cell line by a sucrose gradient provided that utrophin-A is translated inefficiently (FIG. 2). The 5' and 3'-UTRs were dissected in order to confirm that utrophin-A non-coding regions are responsible for the translation repression observed. Cloning the 5' or the 3'-UTR cloned into a reporter gene construct (luciferase) showed that these non-coding regions are indeed responsible for the inefficient utrophin-A translation (FIGS. 3 and 4).

Example 2: Microrna Candidates

Figure 5:
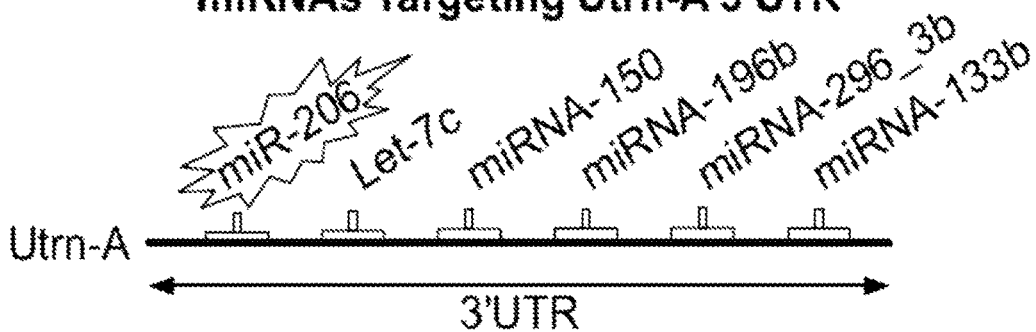
FIG. 5 is a schematic representation of utrophin 3'-UTR microRNA binding sites.

MicroRNA candidates were predicted to target utrophin RNA using the miRanda v1.0.b algorithm. The expression of the predicted microRNAs was confirmed in C2C12 cells or TA by Taqman microRNA assay (FIG. 5).

Example 3: Utrophin-A Repression by Microrna

Figure 6:
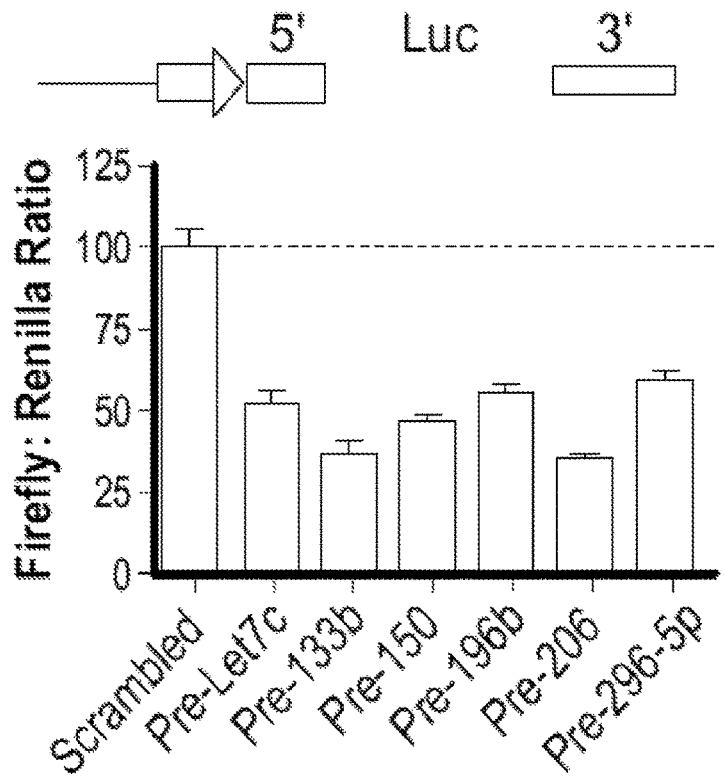
FIG. 6 is a graph showing a decrease in light produced (due to luciferase) on addition of different microRNAs.
Figure 7A:
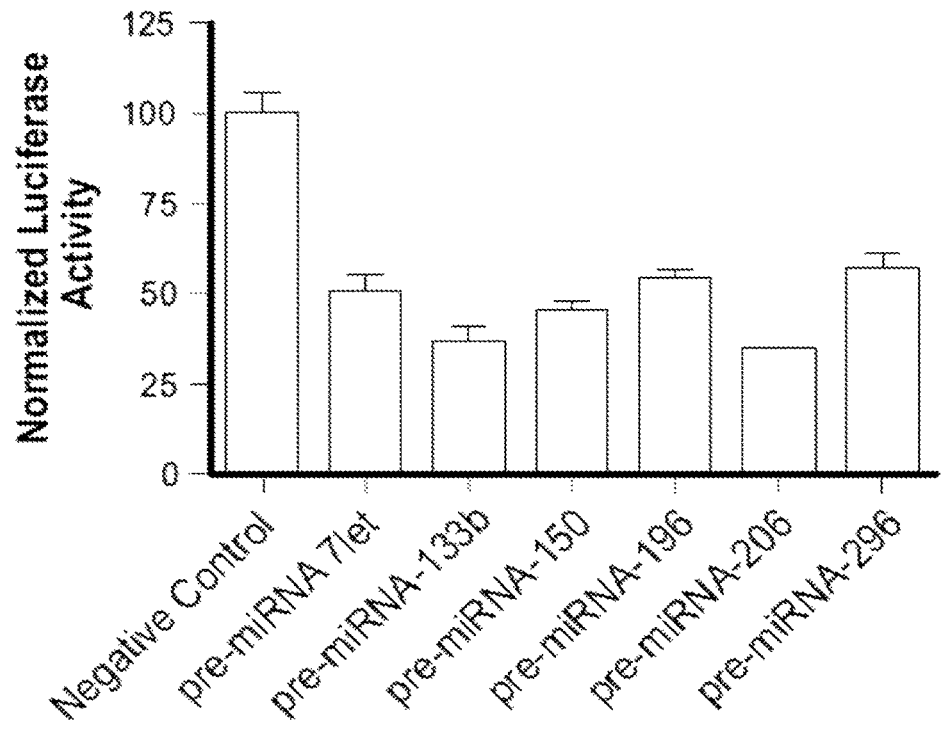
FIG. 7 is a graph showing a decrease in light produced by utrophin UTR-luciferase construct (A) and firefly/*renilla* expression by utrophin UTR-firefly construct (C) on addition of different microRNAs. (B) A graph showing an increase in light produced (due to luciferase) on inhibition of certain microRNAs.
Figure 7B:
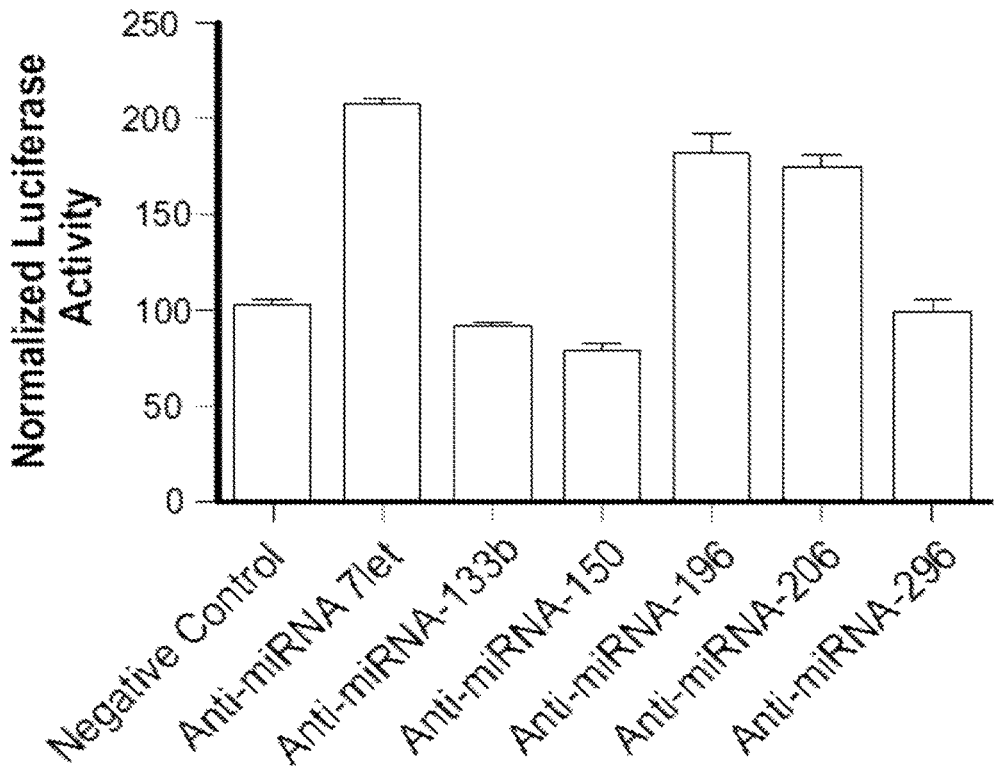
Figure 8:
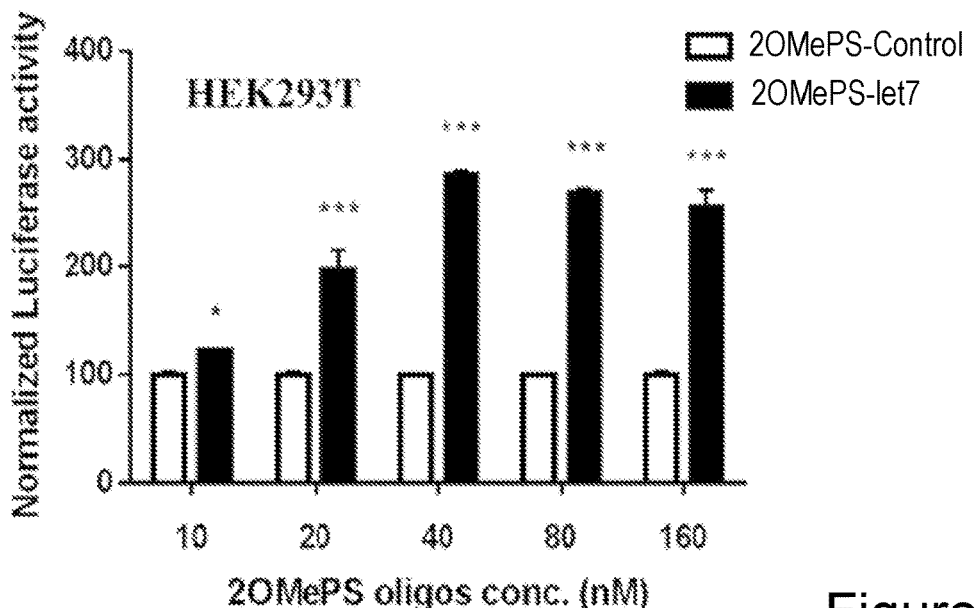
FIG. 8. Utrophin Let-7 site-blocking oligonucleotides (SBOs) upregulate utrophin reporter constructs in human HEK293T cells.
Figure 9:
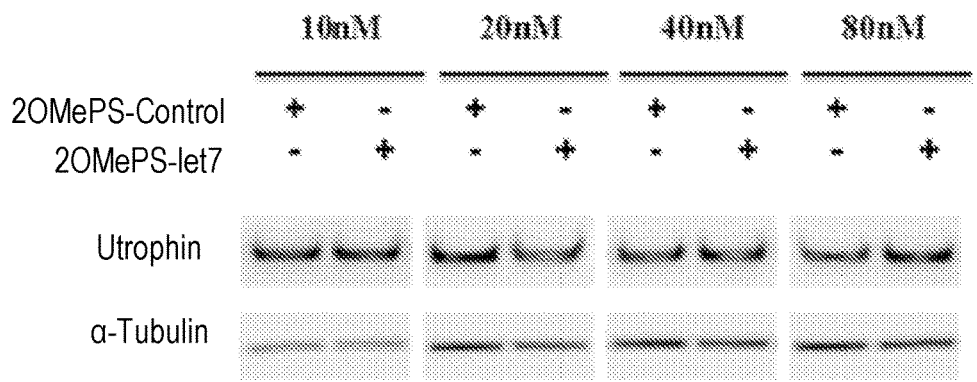
FIG. 9. Utrophin Let-7 SBOs upregulate endogenous utrophin protein in human HEK293T cells.
Figure 9:
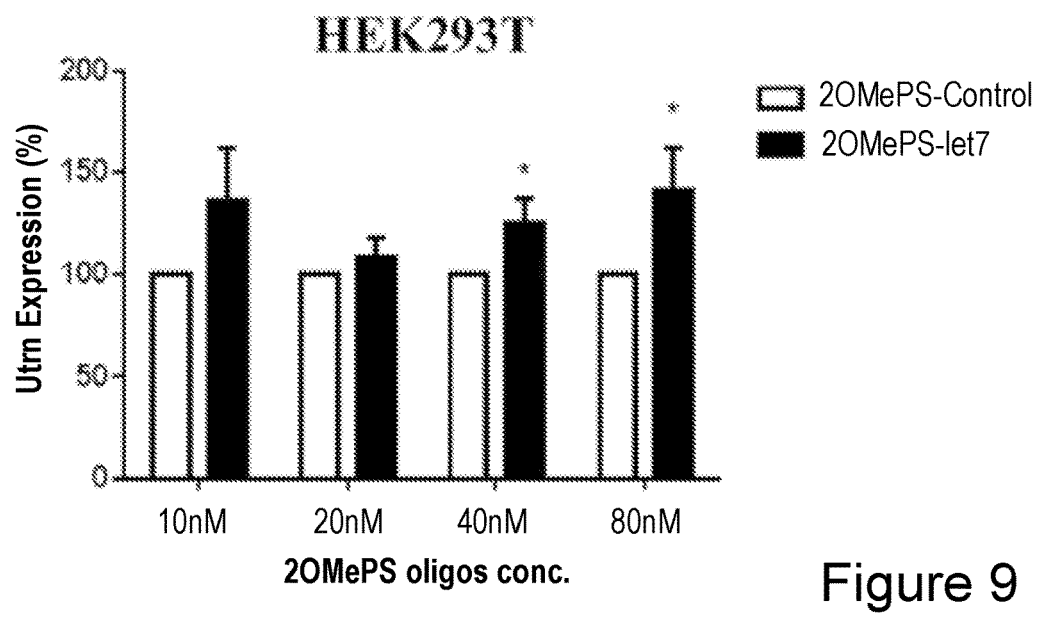
Figure 10:
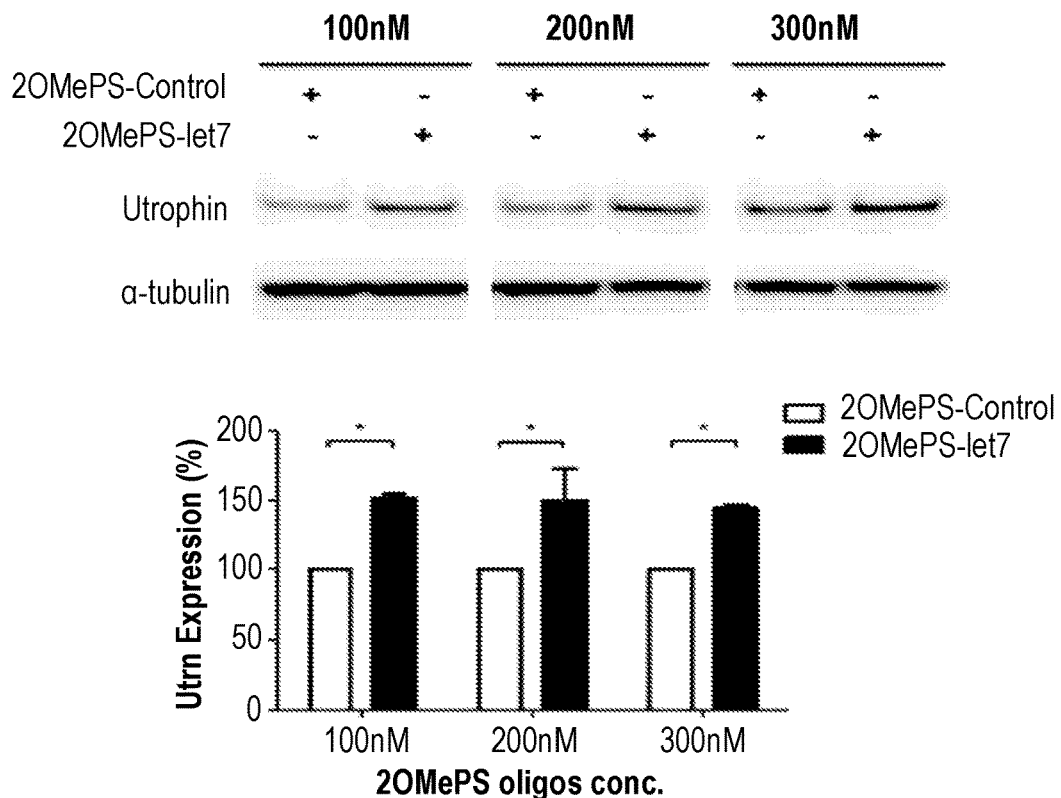
FIG. 10. Utrophin Let-7 SBOs upregulate endogenous utrophin protein in human HEK293T cells.
Figure 11:
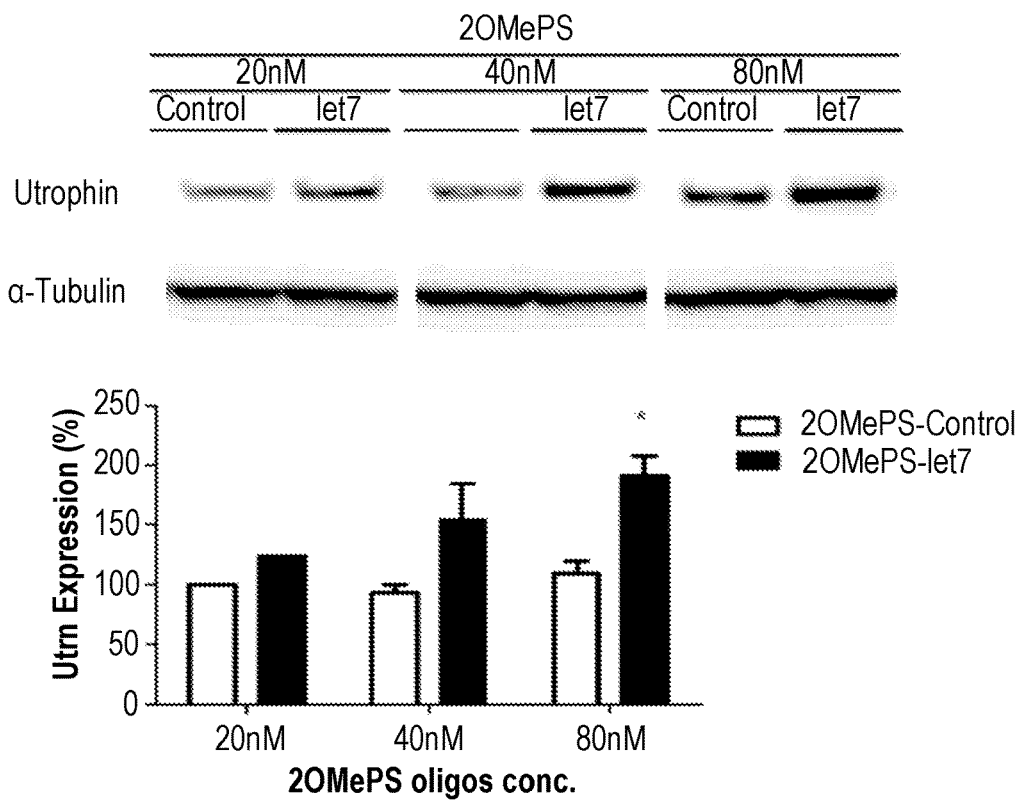
FIG. 11. Utrophin Let-7 SBOs upregulate endogenous utrophin protein in mouse C2C12 cells.

C2C12 cells were transfected with a plasmid comprising a construct containing the 5'-UTR of the utrophin-A mRNA, a luciferase reporting gene, and the 3'-UTR of the utrophin mRNA as in Example 1. The transfected cells were treated with pre-Let-7c, pre-miR-133b, pre-miR-150, pre-miR- 196b, pre-miR-206, pre-miR-296-5p, or a scrambled control sequence. All 6 microRNA constructs repressed luciferase translation, while the scrambled control sequence did not affect luciferase translation (FIGS. 6 and 7). Thus, Let-7c, miR-133b, miR-150, miR-196b, miR-206, and miR-296-5p are able to repress the translation of a gene comprising the 5' and 3'-UTRs of utrophin mRNA. This experiment demonstrated that Let-7c, miR-133b, miR-150, miR-196b, miR-206, and miR-296-5p are responsible for the repression of utrophin-A mRNA translation. Thus, both 5' and 3'-UTRs play an important role in utrophin-A translational repression and the 3'-UTR preferentially represses IRES-mediated translation. Moreover, this experiment demonstrates that the 5'-UTR of the utrophin-A mRNA and the 3'-UTR of the utrophin mRNA are required for the microRNA induced repression.

Example 4: DMD Antisense Therapeutic Approach for Utrophin Up-Regulation

In this example, a utrophin-upregulation based therapeutic approach for Duchenne's Muscular Dystrophy (DMD) was developed using oligonucleotides designed to block the let-7c miRNA binding site (2'-O-methyl phosphorothioate (2'OMePS) let-7c site blocking oligonucleotides (SBOs)) in the 3'-UTR of the Utrophin gene.

First, efficacy of let-7 SBOs was validated in C2C12 (mouse), as well as human (HEK293T), cell lines in vitro. The utrophin let-7 site-blocking oligonucleotides (SBOs) were able to upregulate utrophin reporter constructs, as well as endogenous utrophin protein (FIGS. 8-11).

Figure 12:
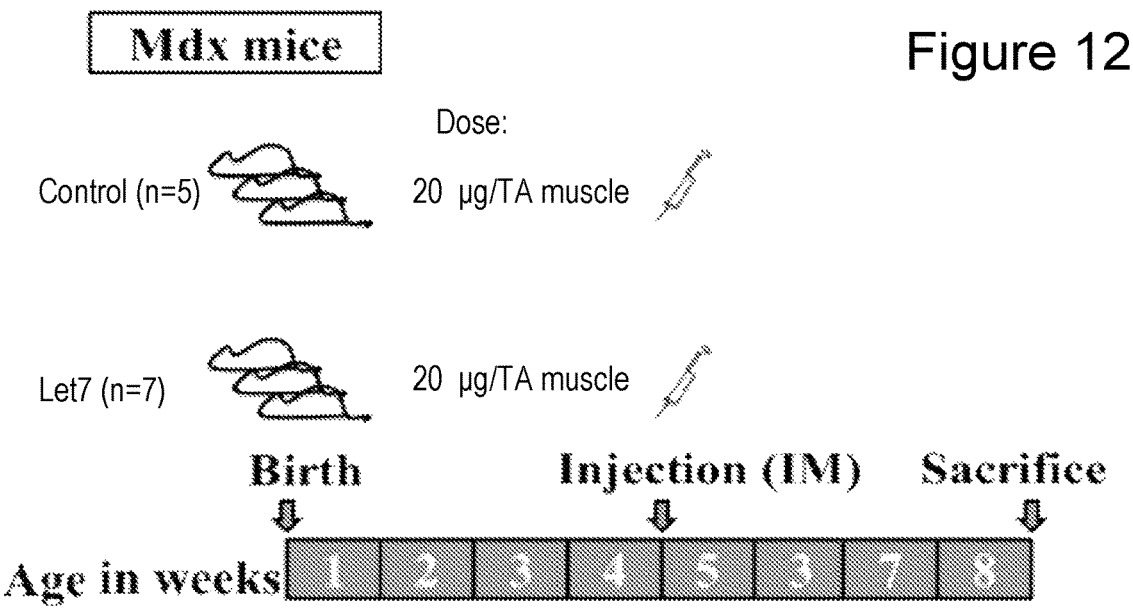
FIG. 12. Experimental scheme for pharmacodynamic studies of utrophin let-7 SBOs injected intramuscularly in the mdx mouse model for DMD in vivo.
Figure 13:
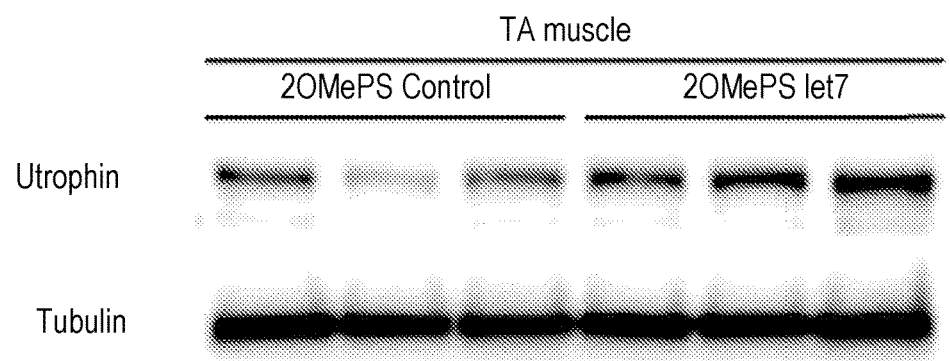
FIG. 13. Utrophin protein expression was upregulated significantly, as measured by Western blot, in Tibialis anterior (TA) muscles of mdx mouse model for DMD in vivo.
Figure 13:
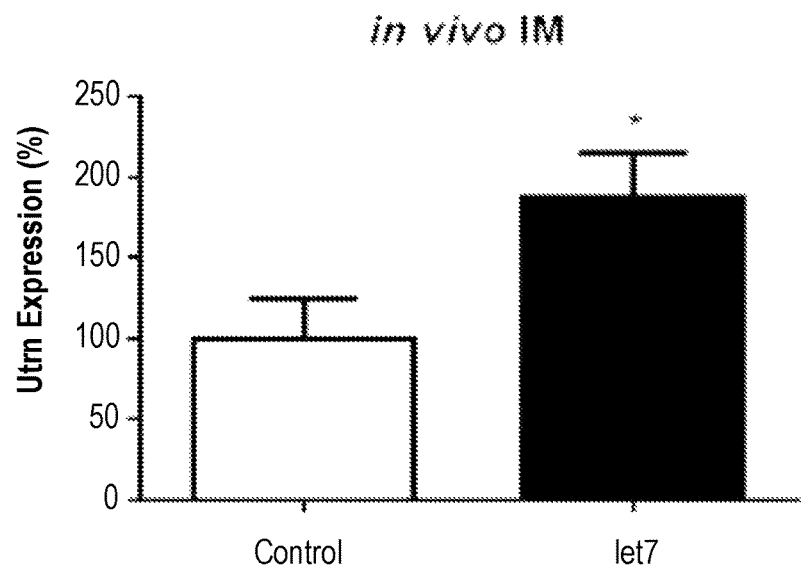

Second, pharmacodynamic studies were successfully conducted in the mdx mouse model for DMD in vivo (FIG. 12). Utrophin protein expression was upregulated significantly, as measured by Western blot, in Tibialis anterior (TA) muscles of 1 month old mdx mice that had been injected for 1 month with 20 micrograms of let7 SBO (FIG. 13).

Figure 14:
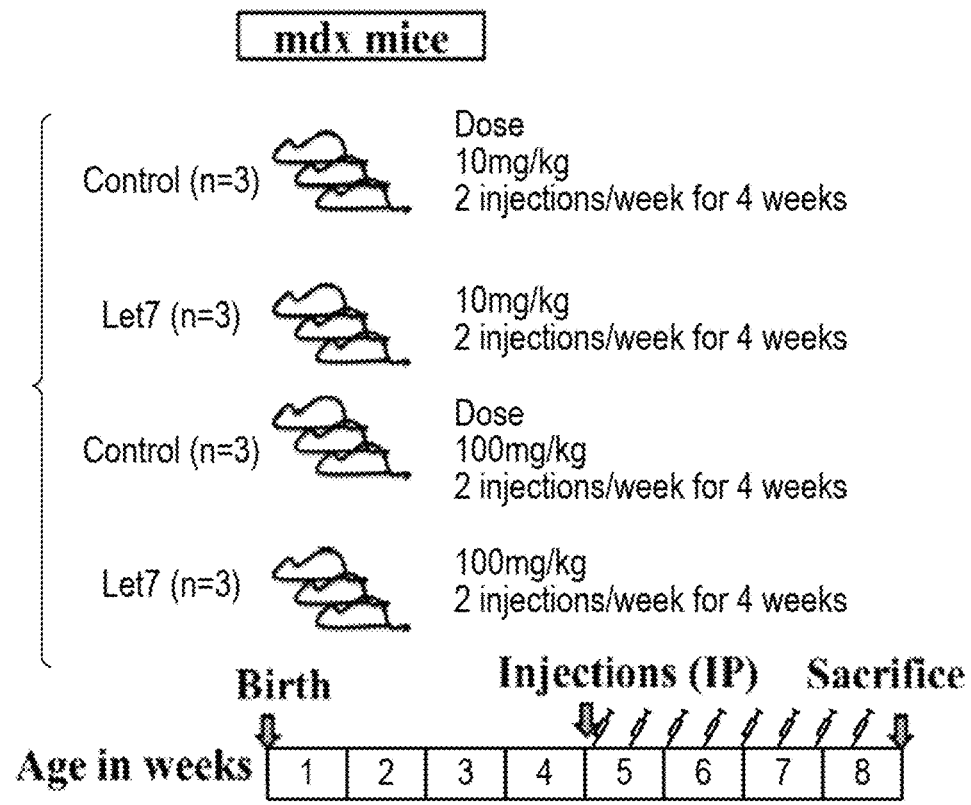
FIG. 14. Experimental scheme for studies of utrophin let-7 SBOs administered systemically in the mdx mouse model for DMD in vivo.
Figure 15:
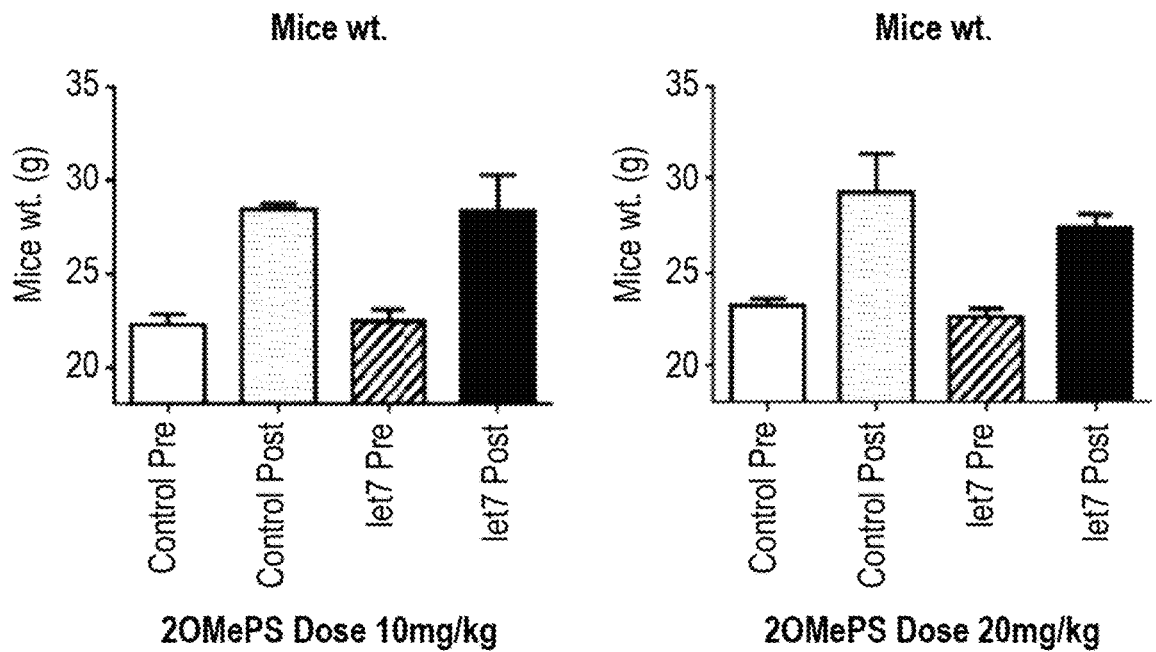
FIG. 15. Utrophin Let-7 SBO administration did not change body weight.

Third, using systemic delivery of let-7 SBOs for 2 months in mdx mice to block endogenous let-7c binding to the utrophin gene (FIG. 14) resulted in significant morphological, biochemical and physiological improvement of the dystrophic phenotype in vivo, without adverse effects such as a significant change in body weight relative to the control mice (FIG. 15)

Figure 16:
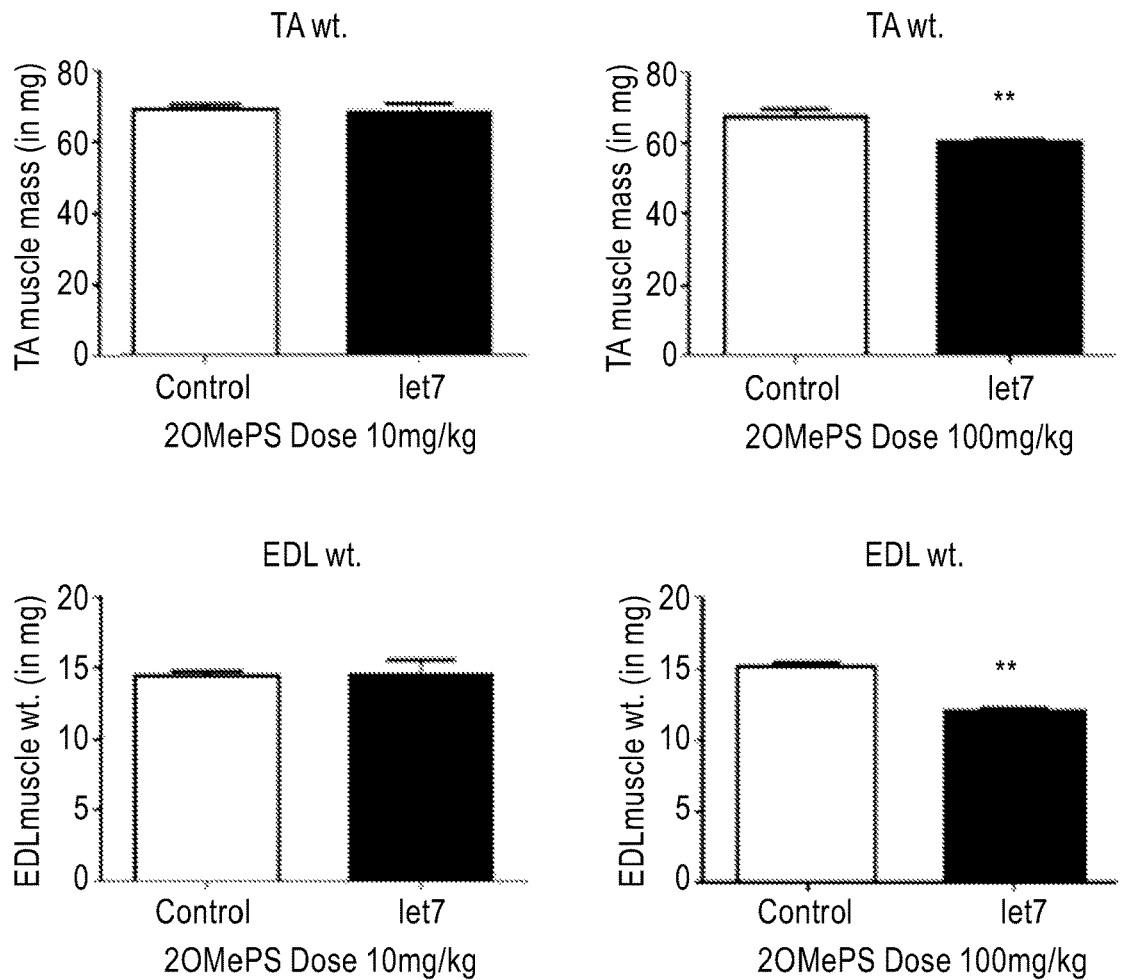
FIG. 16. Utrophin Let-7 SBO administration reduced extensor digitorum longus (EDL) muscle weight.
Figure 17:
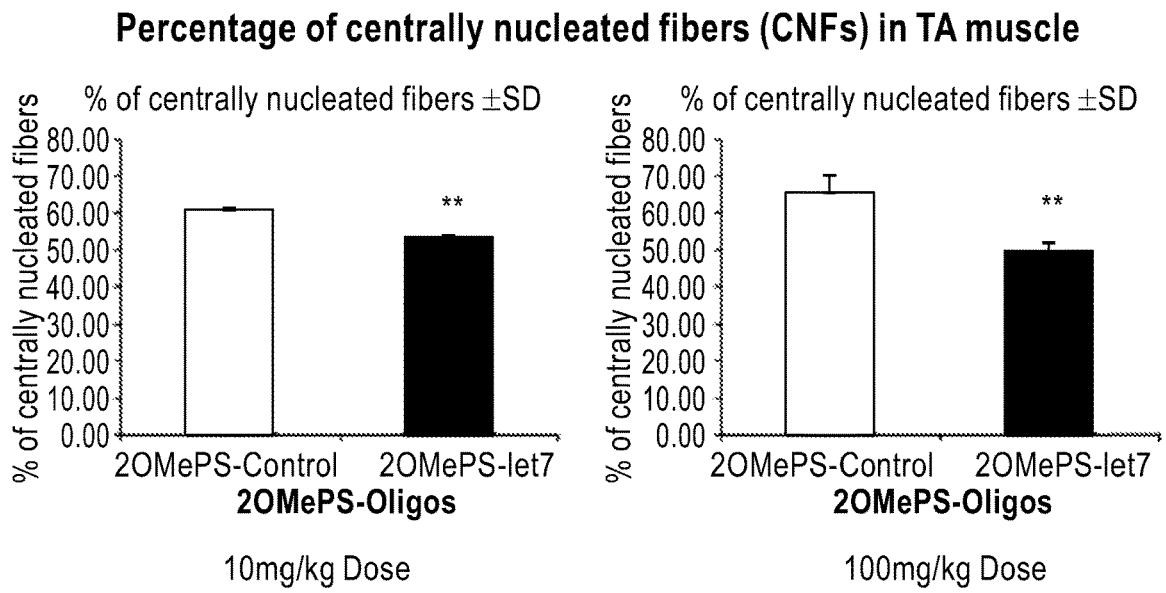
FIG. 17. Utrophin Let-7 SBO treatment decreased centrally nucleated fibers (CNFs) in TA muscle.
Figure 18:
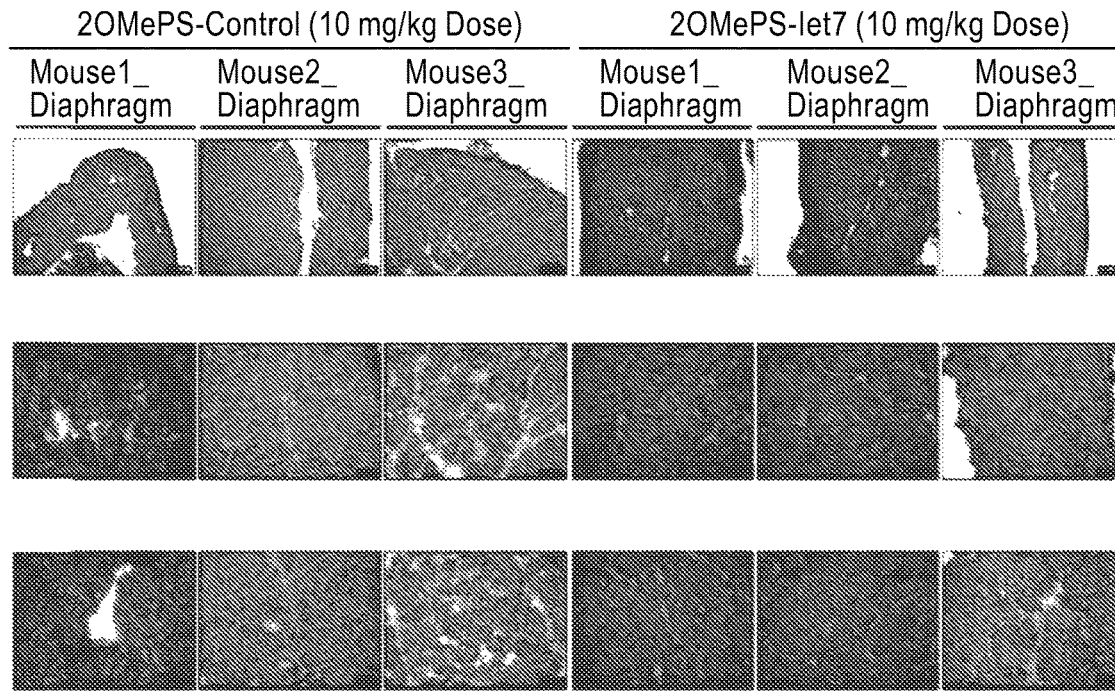
FIG. 18. Histopathological changes were decreased by let-7 treatment. H&E staining—10 mg/kg dose. Cryostat sections of Diaphragm muscle of Mdx mouse stained with hematoxylin and eosin after 1 month of treatment with 10 mg/kg 2OMePS-Control and 2OMePS-let7 oligonucleotides. (Note: images were stitched together side by side to give a single large 2D image frame at 10× magnification).
Figure 19:
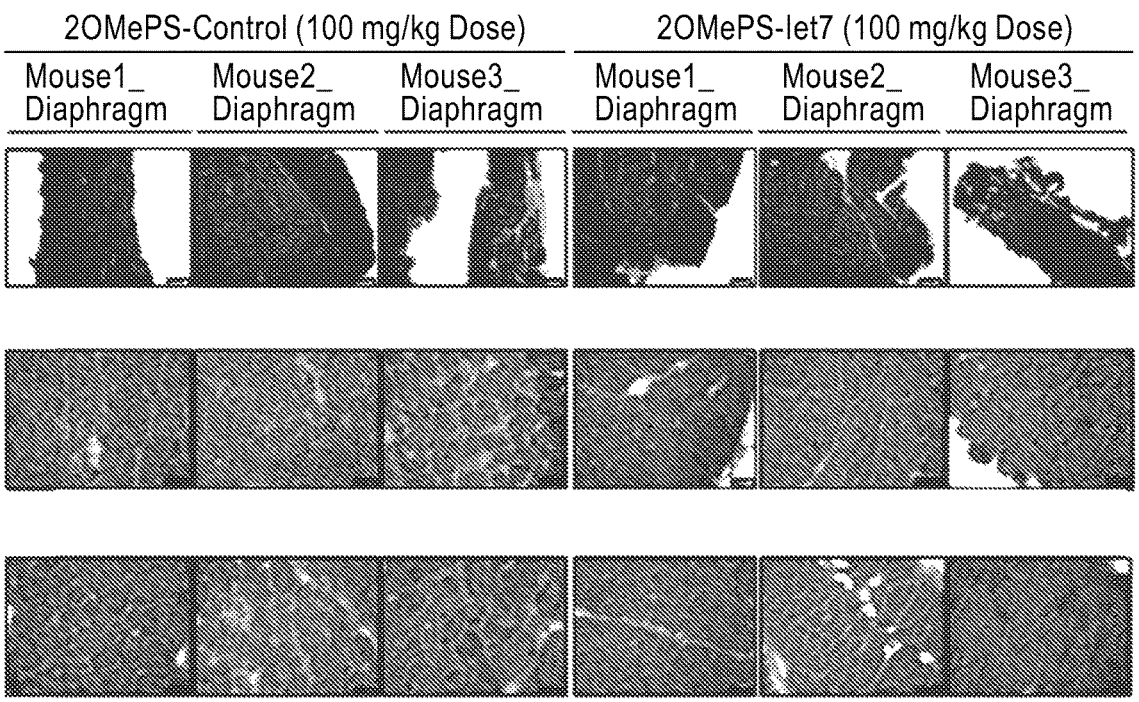
FIG. 19. Histopathological changes were decreased by let-7 treatment. H&E staining—100 mg/kg dose. Cryostat sections of Diaphragm muscle of Mdx mouse stained with hematoxylin and eosin after 1 month of treatment with 100 mg/kg 2OMePS-Control and 2OMePS-let7 oligonucleotides. (Note: images were stitched together side by side to give a single large 2D image frame at 10× magnification).
Figure 20:
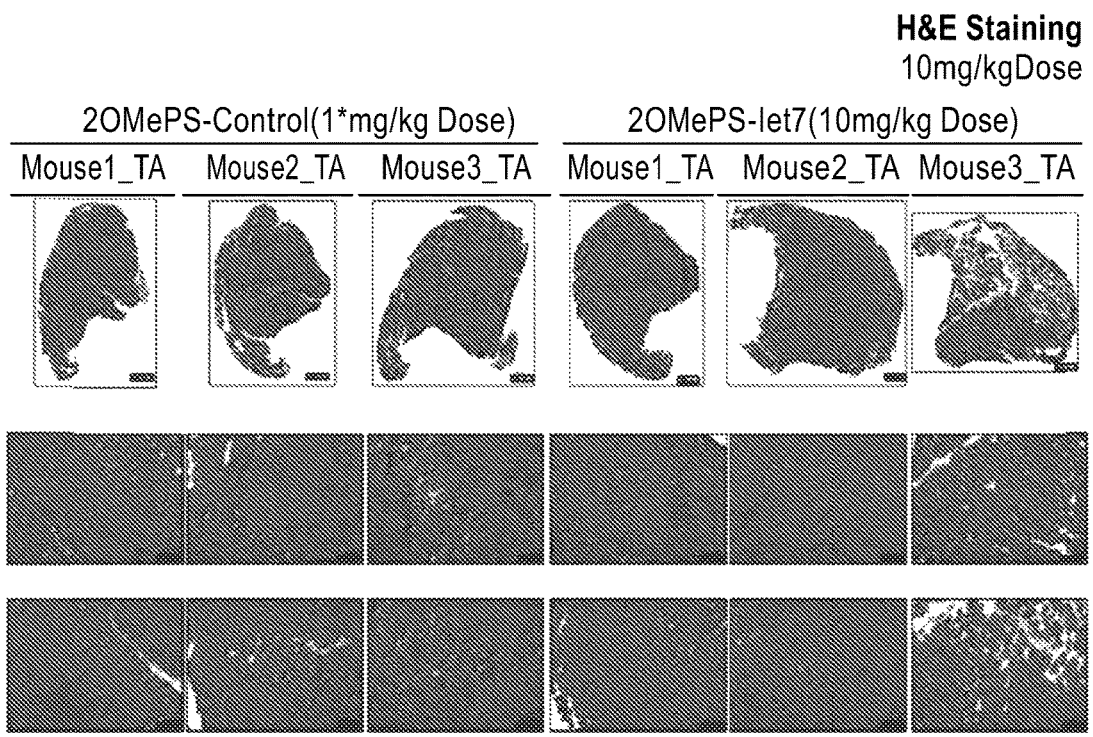
FIG. 20. Histopathological changes were decreased by let-7 treatment. H&E staining—10 mg/kg dose. Cryostat sections of TA muscle of Mdx mouse stained with hematoxylin and eosin after 1 month of treatment with 10 mg/kg 2OMePS-Control and 2OMePS-let7 oligonucleotides. (Note: images were stitched together side by side to give a single large 2D image frame at 10× magnification).
Figure 21:
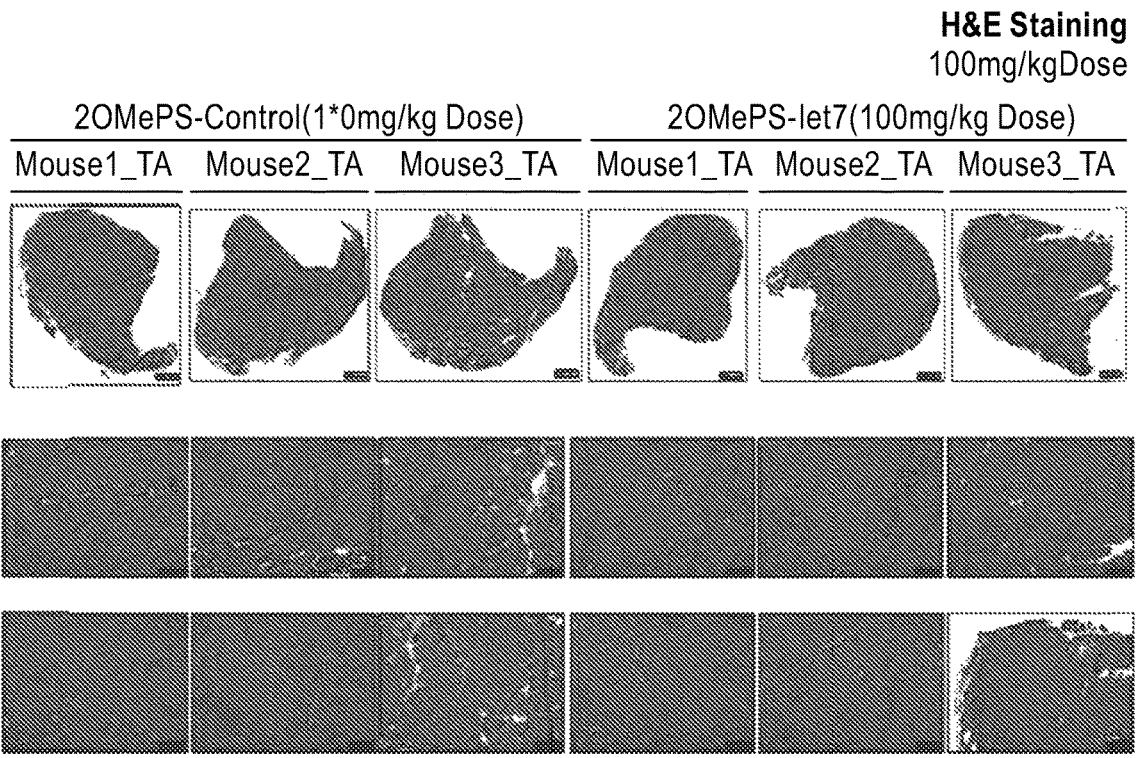
FIG. 21. Histopathological changes were decreased by let-7 treatment. H&E staining—100 mg/kg dose. Cryostat sections of TA muscle of Mdx mouse stained with hematoxylin and eosin after 1 month of treatment with 100 mg/kg 2OMePS-Control and 2OMePS-let7 oligonucleotides. (Note: images were stitched together side by side to give a single large 2D image frame at 10× magnification).
Figure 22:
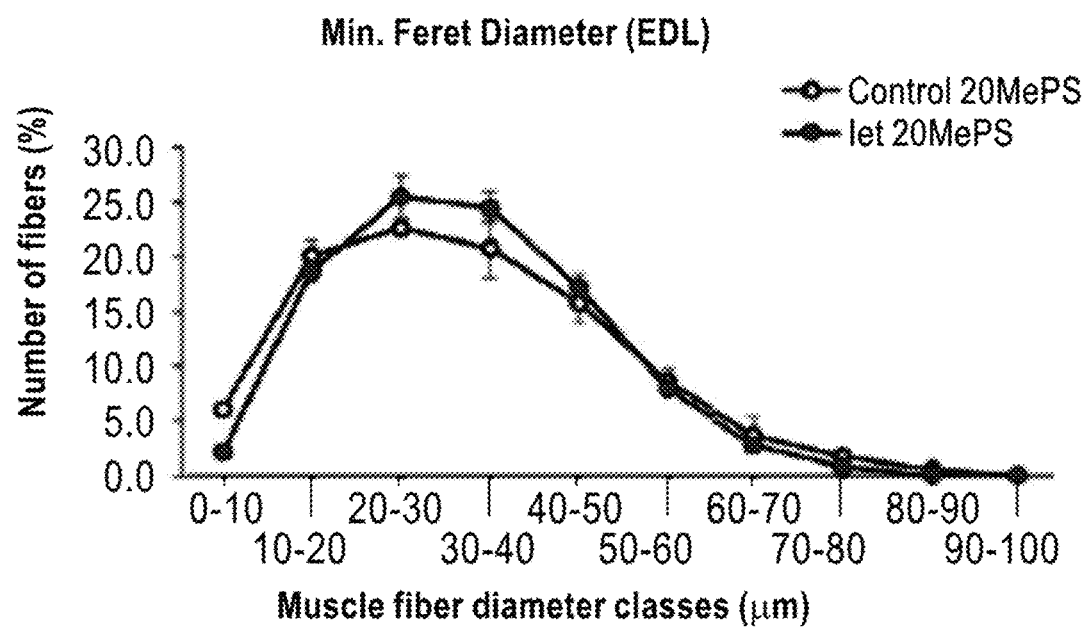
FIG. 22. Utrophin Let-7 SBO treatment decreased muscle fiber size variability.
Figure 22:
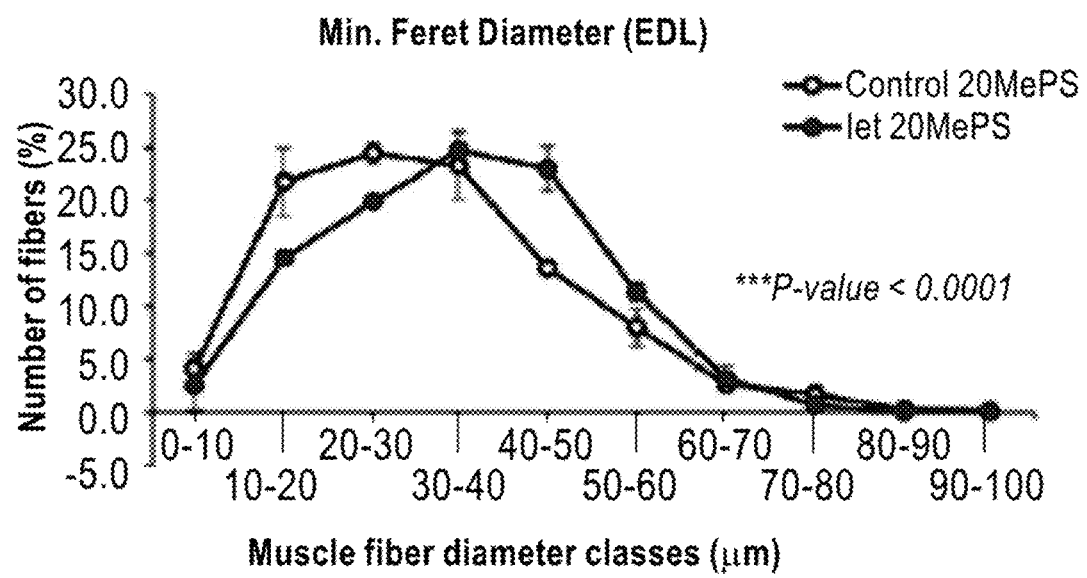
Figure 23:
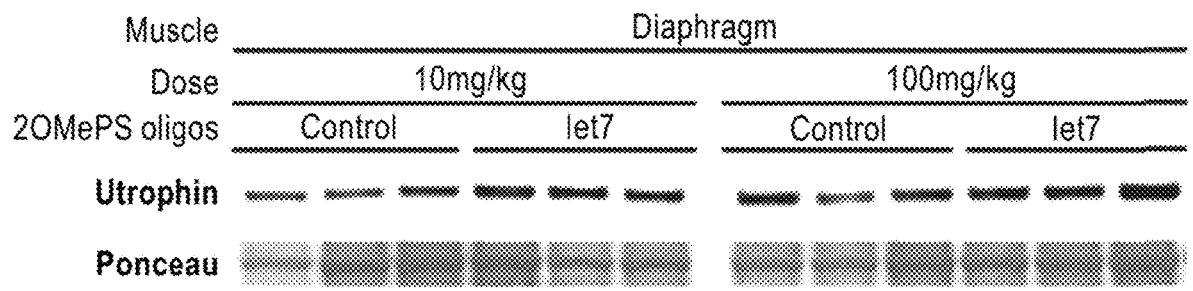
FIG. 23. Utrophin Let-7 SBO administration increased utrophin protein expression in the diaphragm.
Figure 23:
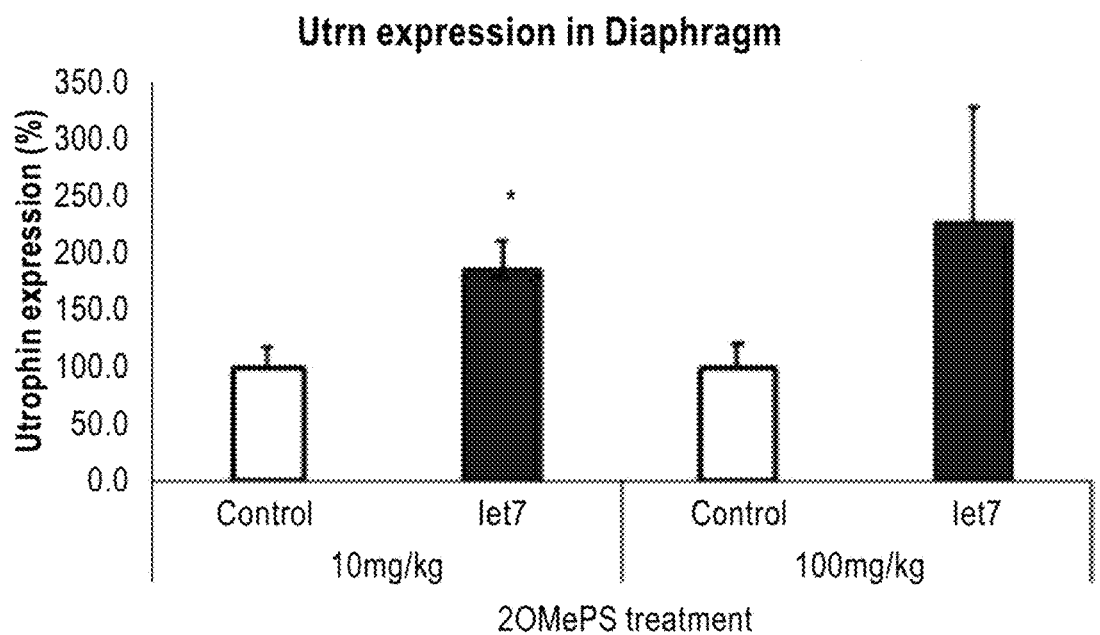
Figure 24:
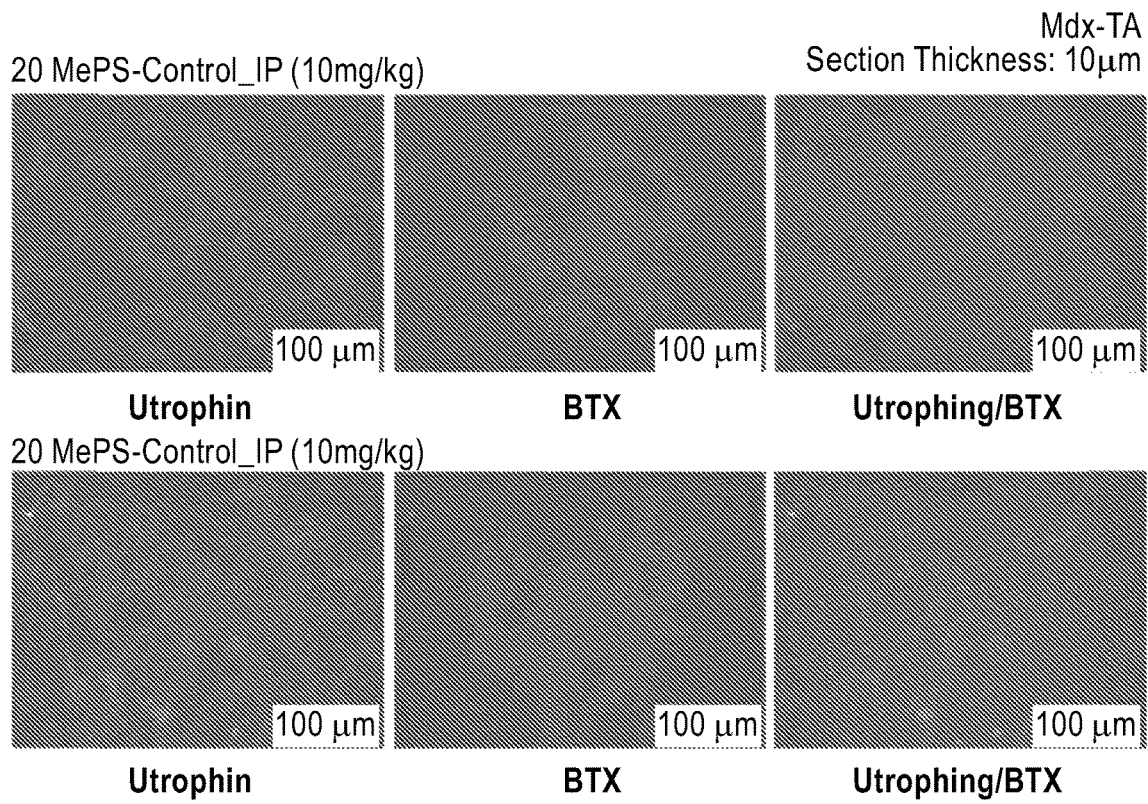
FIG. 24. Increased utrophin expression was seen in NMJ-poor areas after let-7 treatment.
Figure 25:
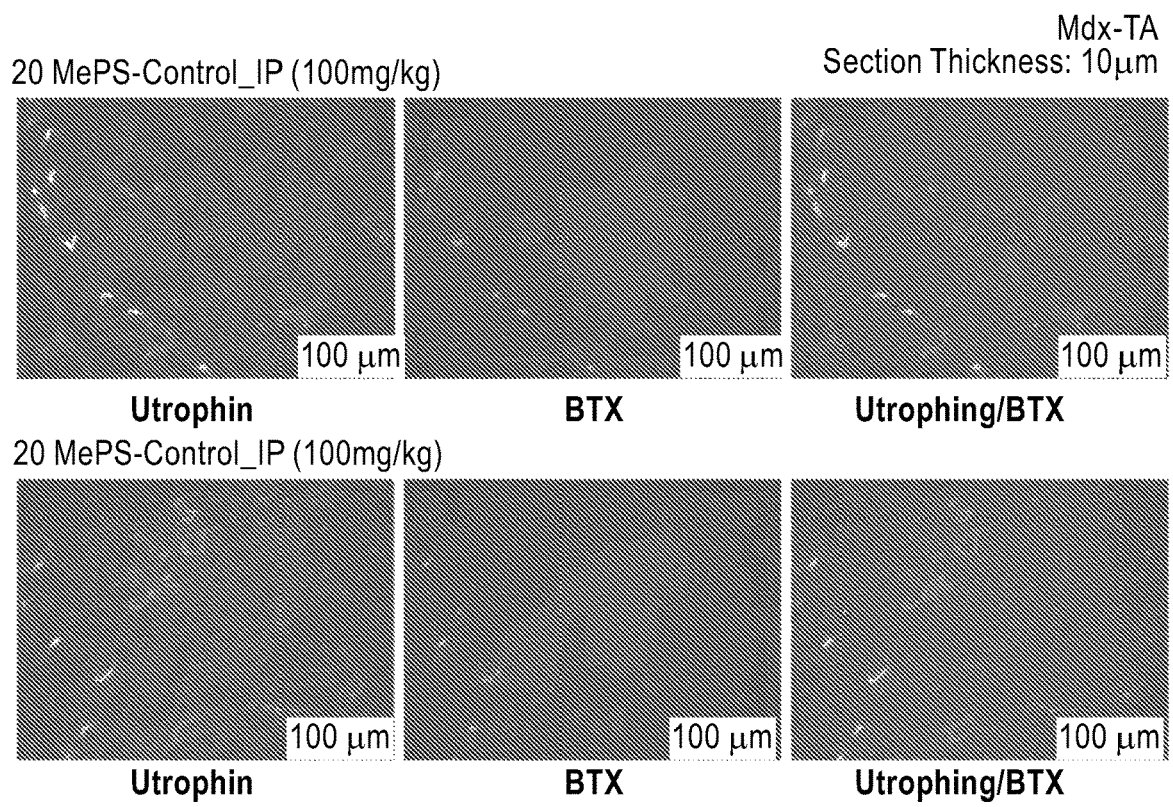
FIG. 25. Increased utrophin expression was seen in NMJ-rich areas after let-7 treatment.
Figure 26:
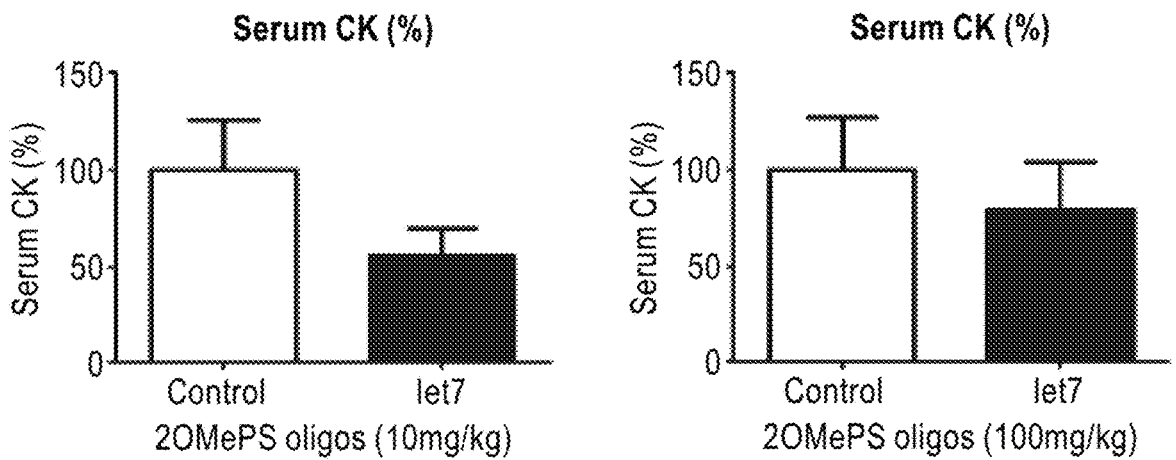
FIG. 26. Let-7 SBO treatment and serum CK reduction.
Figure 27:
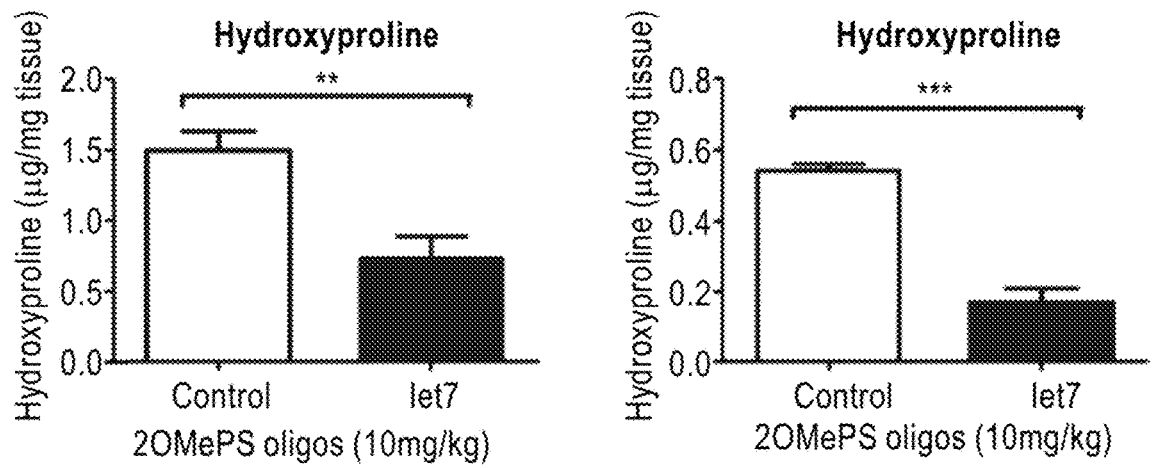
FIG. 27. Hydroxyproline content of fibularis muscles. Let-7 SBO treatment reduced fibrosis as evidenced by Hydroxyproline content.
Figure 28:
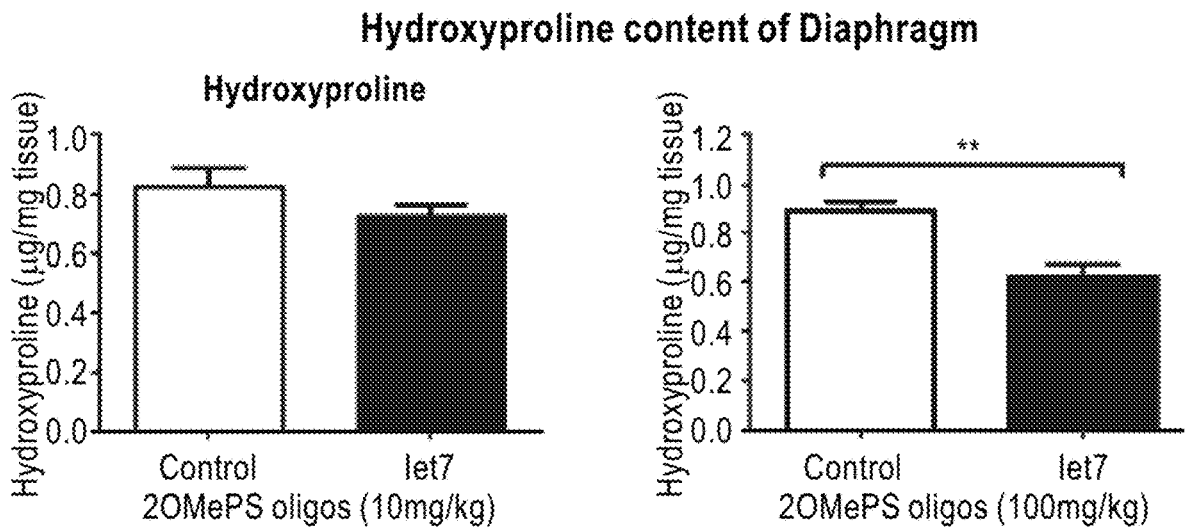
FIG. 28. Hydroxyproline content of Diaphragm. Utrophin let-7 SBO treatment reduced fibrosis as evidenced by Hydroxyproline content.
Figure 29:
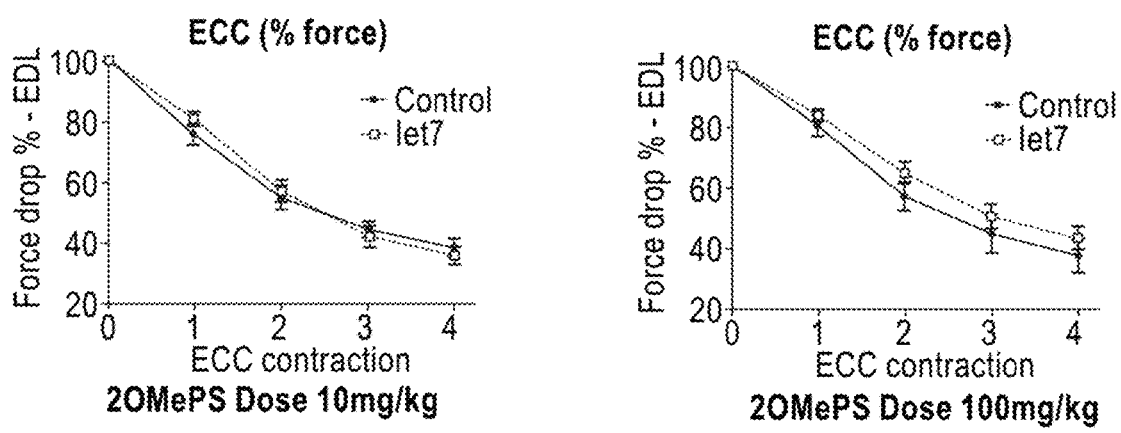
FIG. 29. Utrophin let-7 SBO treatment did not change post-eccentric contraction force drop.
Figure 30:
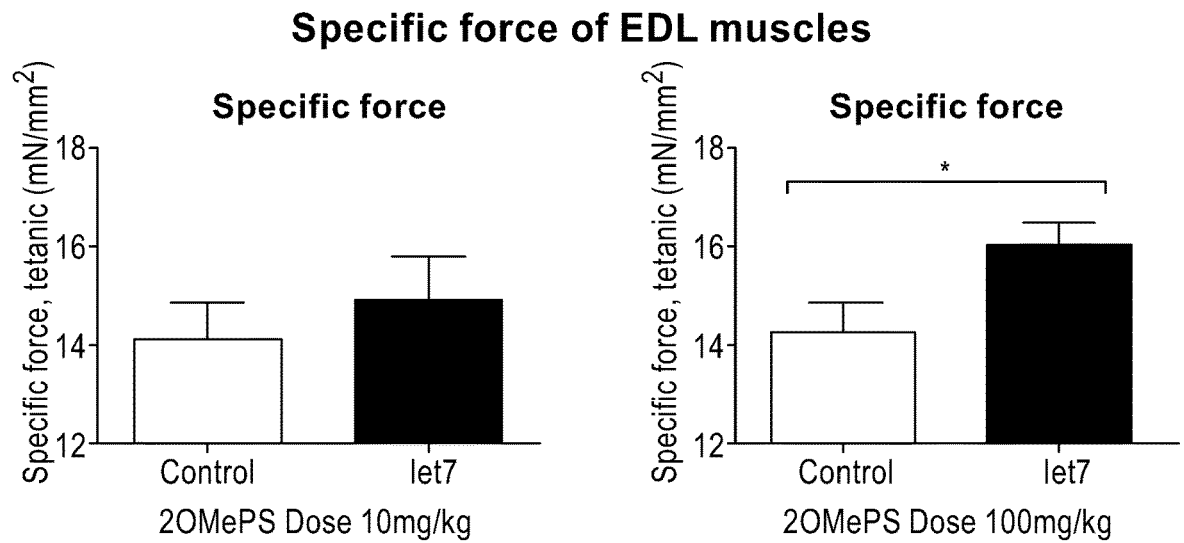
FIG. 30. Utrophin let-7 SBO treatment increased specific force of EDL muscles.

Specifically, utrophin let-7 SBO treatment reduced extensor digitorum longus (EDL) muscle weight (FIG. 16). Utrophin let-7 SBO treatment decreased centrally nucleated fibers (CNFs) in TA muscle (FIG. 17). Histopathological changes were decreased by let-7c treatment in diaphragm and TA muscles (FIGS. 18-21). Let-7 SBO treatment also reduced muscle fiber size variability (FIG. 22). Let-7 SBO treatment was observed to increase utrophin protein expression in the diaphragm (FIG. 23). Increased utrophin expression was seen in both NMJ-poor (FIG. 24) and NMJ-rich (FIG. 25) areas. Serum CK reduction upon let-7 SBO treatment was measure (FIG. 26). As evidenced by hydroxyproline content, let-7 SBO treatment decreased muscle fibrosis (FIG. 27-28). While let-7 SBO treatment did not change post-eccentric contraction force drop in EDL muscles (FIG. 29), treat did decrease specific force in EDL muscles (FIG. 30). In sum, these results establish let-7 SBOs as a therapeutic approach for DMD.

Example 5: 2'F-ANA-Let7 Antisense miRNA Upregulates Utrophin Expression

In Example 4, blocking binding of let-7 miRNA to the utrophin 3'-UTR, using 2'OMePS-let7 SBOs (site-blocking oligonucleotides), was shown to upregulate endogenous utrophin protein by over 2-fold in C2C12 cells and mdx mice. The next generation 2'-Deoxy-2'-Fluoro-β-D-Arabinose Nucleic Acid (2'F-ANA) can provide potent, stable, efficient and cost-effective solutions for basic biomedical research, clinical diagnostics and therapeutics. Recent studies show that 2'F-ANA oligonucleotides have higher resistance to the action of degradative nucleases present in serum, bind to mRNA through duplex formation, elicit or avert RNase H activity, and effectively alter intracellular specific gene expression in a highly persistent manner. Their ability to self-deliver (gymnotic delivery) without the need for additional carriers also make them attractive for use in pre-clinical studies and therapeutic development in DMD.

Figure 31:
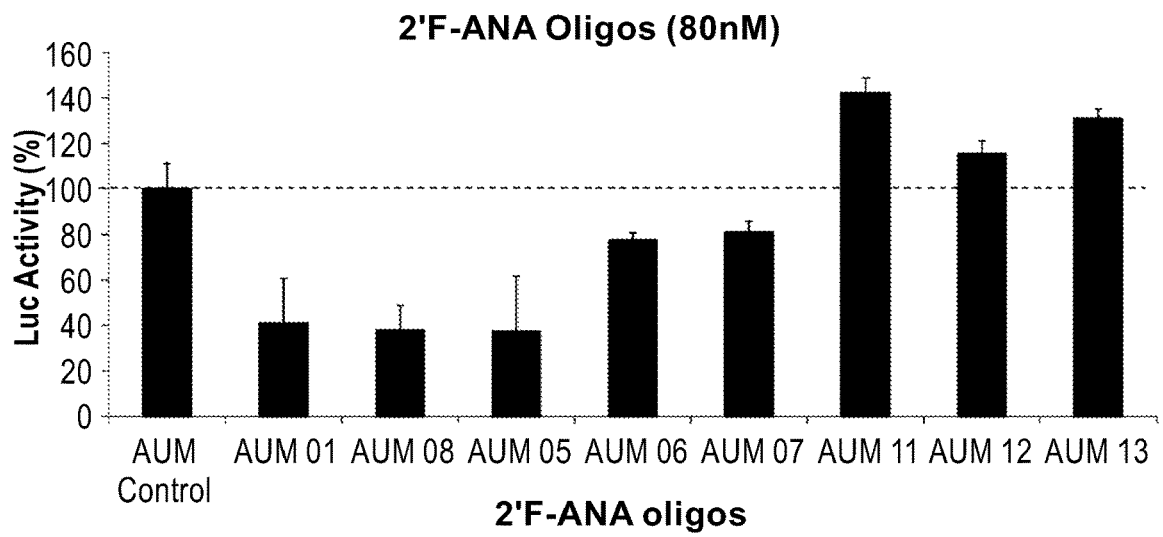
FIG. 31. Luciferase activity in C2C12-5'Luc3' utrophin reporter cells transfected with 2'F-ANA-let7 oligonucleotides 24 hours post transfection.
Figure 32A:
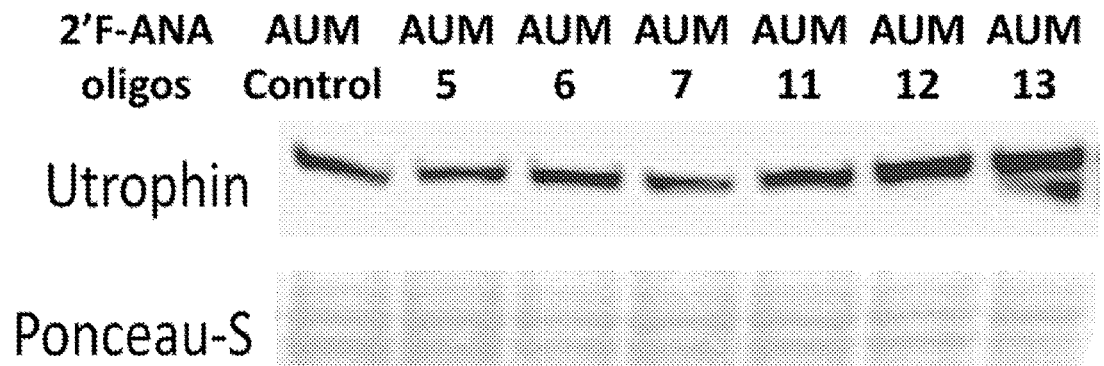
FIG. 32. Western blot assay showing utrophin upregulation in C2C12 cells transfected with 2'F-ANA-let7 oligonucleotides 24 hours post transfection.
Figure 32B:
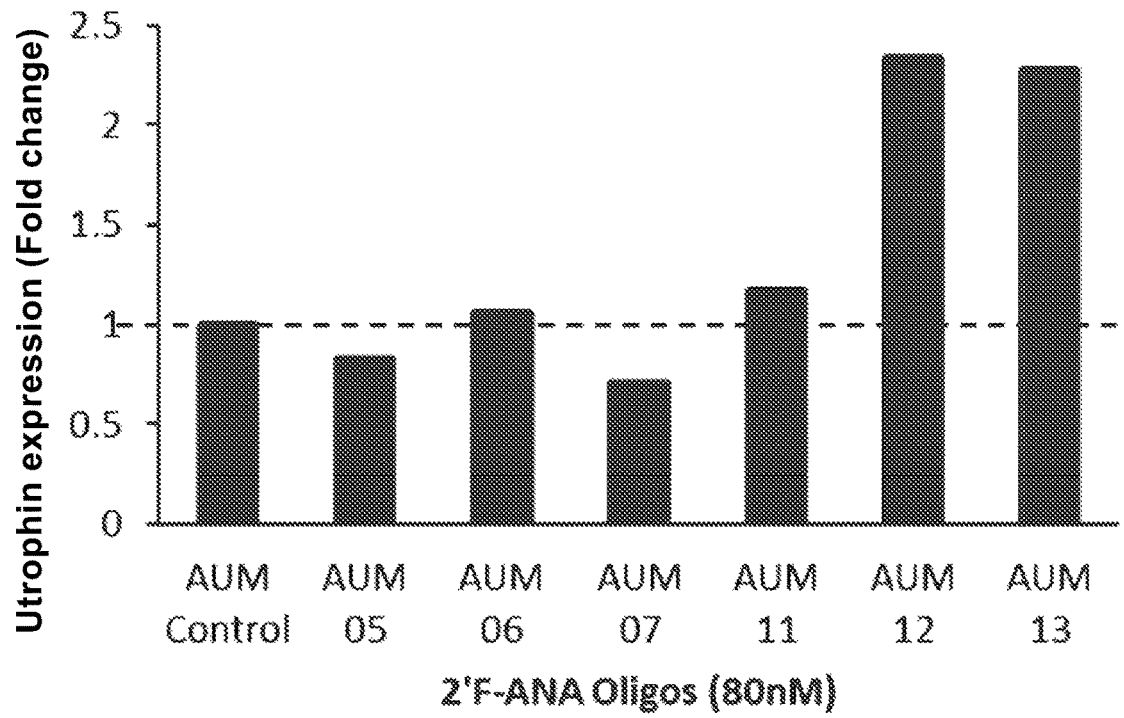
Figure 33:
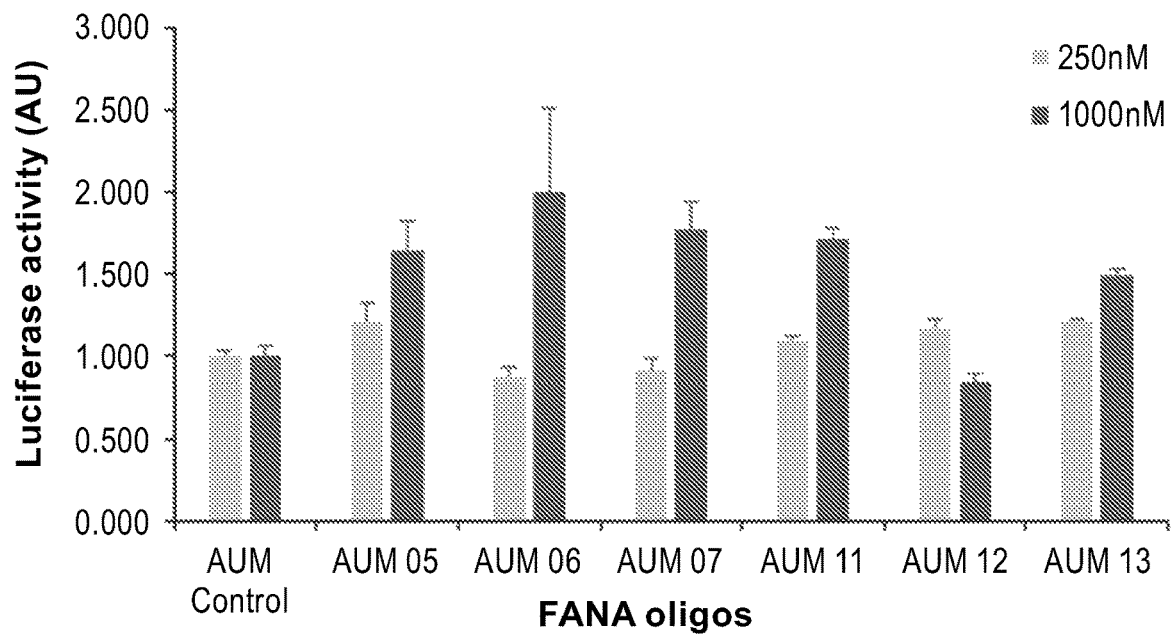
FIG. 33. Luciferase activity in C2C12-5'Luc3' utrophin reporter cells after 24 hours of gymnotic delivery of 2'F-ANA-let7 oligonucleotides.
Figure 34:
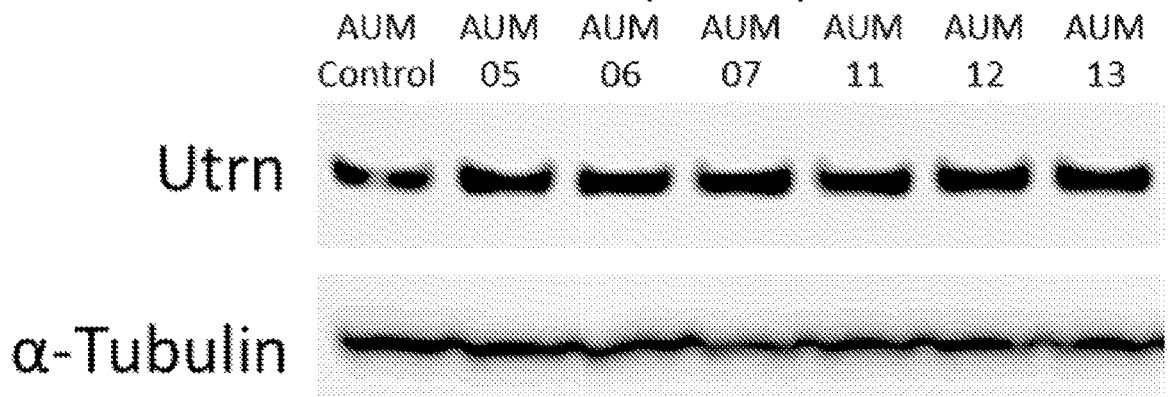
FIG. 34. Western blot assay showing utrophin upregulation in C2C12 cells after 24 hours of gymnotic delivery of 2'F-ANA-let7 oligonucleotides.
Figure 34:
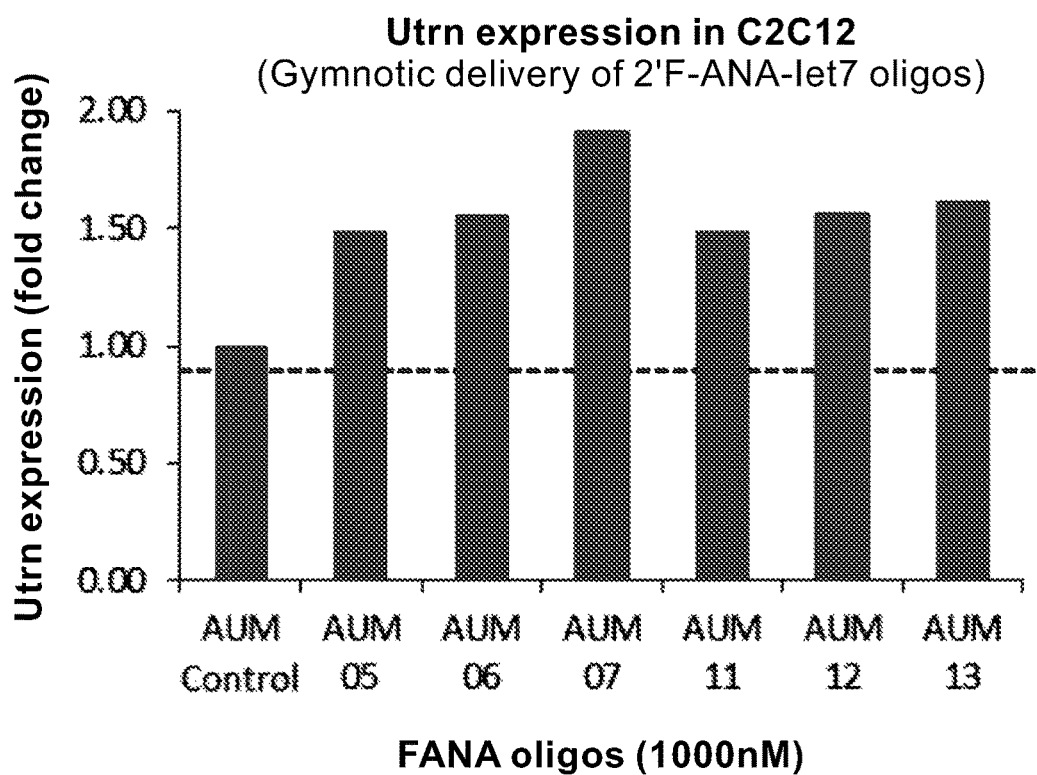

In this Example, 2'F-ANA-let7 oligonucleotides were used to alleviate miRNA-mediated utrophin-A repression by blocking the binding of miRNA let-7c to its target in utrophin 3'UTR (FIG. 1). Several let-7 miRNA site blocking 2'F-ANA oligonucleotides (see SEQ ID NOs: 64-in Table 1) were designed, and the oligonucleotide AUM Control (5'-GUGAGCACUTCTUUCCTTCUUTTUU-3'; SEQ ID NO: 76) was used as a control. In the 2'F-ANA-let7 SBOs, all of the internucleoside linkages were phosphorothioate linkages. Oligonucleotides AUM 11-AUM 13 have the sequences set forth SEQ ID NOs: 73-75 and a structure F-D-F-D- . . . -F-D-F-D-F (F is a 2'F-ANA nucleoside and D is a 2'-deoxynucleoside). Oligonucleotides AUM 05-AUM 07 have the sequences set forth SEQ ID NOs: 67-69 and a structure F-F-D-D- . . . -F-F-D-D-F-F (F is a 2'F-ANA nucleoside and D is a 2'-deoxynucleoside). In addition, the oligonucleotide AUM 01 has the sequence set forth SEQ ID NO: 64 and a structure F-F-F-D-D-D . . . F-F-F-D-D-D-F-F-F (F is a 2'F-ANA nucleoside and D is a 2'-deoxynucleoside). Finally, the oligonucleotide AUM 08 has the sequence set forth SEQ ID NO: 70 with a central segment consisting of twelve 2'-deoxynucleosides that is flanked by segments in the 5' direction and the 3' direction consisting of six 2'F-ANA nucleosides each. An increase in luciferase activity in C2C12-5'Luc3' utrophin reporter cells transfected with 2'F-ANA-let7 SBOs was observed 24 hours post-transfection (FIG. 31). Western assays of C2C12 cells transfected with 2'F-ANA-let7 SBOs also show an increase in endogenous utrophin protein expression 24 hours post-transfection (FIG. 32). Gymnotic delivery of 2'F-ANA-let7 SBOs also shows an increase in luciferase activity in C2C12-5'Luc3' utrophin reporter cells (FIG. 33) and utrophin protein expression in C2C12 cells (FIG. 34). Thus, 2'F-ANA-let7 SBOs were found to have therapeutic potential for pre-clinical trials and for the establishment of a successful therapy for DMD.

All references, including publications, patent applications, and patents, cited herein are hereby incorporated by reference in its entirety herein.

Having described preferred embodiments of the invention with reference to the accompanying drawings, it is to be understood that the invention is not limited to the precise embodiments, and that various changes and modifications may be affected therein by those skilled in the art without departing from the scope or spirit of the invention as defined in the appended claims.

The invention claimed is:

1. An oligonucleotide comprising one or more arabinonucleotides, wherein the oligonucleotide specifically hybridizes to a Let-7c microRNA binding sequence in a utrophin mRNA 3' untranslated region (UTR) and inhibits the binding of the Let-7c microRNA to the utrophin mRNA 3'-UTR, wherein said Let-7c microRNA binding sequence is SEQ ID NO:62, and the oligonucleotide comprises a nucleic acid sequence that is complementary to a contiguous sequence of at least 20 nucleotides of SEQ ID NO:62, wherein the oligonucleotide has a nucleic acid sequence set forth in SEQ ID NOs:64-75.

2. The oligonucleotide of claim 1 wherein the oligonucleotide comprises alternating segments or units of arabinonucleotides and 2'-deoxynucleotides, wherein the segments or units each independently comprise at least one arabinonucleotide or 2'deoxynucleotide.

3. The oligonucleotide of claim 1, wherein a heteroduplex formed by the oligonucleotide and the binding sequence is resistant to cleavage by RNase H.

4. The oligonucleotide of claim 1, wherein the arabinonucleotides are 2'-deoxy-2'-fluoro-P-D-arabinonucleoside.

5. The oligonucleotide of claim 1, wherein the oligonucleotide comprises one or more phosphorothioate internucleotide linkages.

6. A pharmaceutical composition comprising the oligonucleotide of claim 1 and at least one pharmaceutically acceptable excipient.

7. A method for enhancing utrophin production in a subject, the method comprising: administering to the subject an effective amount of the oligonucleotide according to claim 1.

8. A method of treating Duchenne Muscular Dystrophy (DMD) in a human subject, the method comprising: administering to the subject an effective amount of an oligonucleotide according to claim 1.

9. The method of claim 8, wherein the oligonucleotide comprises alternating segments or units of arabinonucleotides and 2'-deoxynucleotides, wherein the segments or units each independently comprise at least one arabinonucleotide or 2'-deoxynucleotide.

10. The method of claim 8, wherein a heteroduplex formed by the oligonucleotide and the binding sequence is resistant to cleavage by RNase H.

11. The method of claim 8, wherein the arabinonucleotides are 2'-deoxy-2'fluoro-P-D-arabinonucleoside.

12. The method of claim 8, wherein the oligonucleotide comprises one or more phosphorothioate internucleotide linkages.

13. The method of claim 8, wherein the oligonucleotide has a nucleic acid sequence set forth in SEQ ID NOs: 26-55 and 64-75.

14. The method of claim 8, wherein the oligonucleotide is between 20 and 32 nucleotides long.

15. The method of claim 8, wherein the oligonucleotide is administered systemically or wherein administration of the oligonucleotide is gymnotic.

* * * * *

SEQUENCE LISTING

<160> NUMBER OF SEQ ID NOS: 76

<210> SEQ ID NO 1
<211> LENGTH: 22
<212> TYPE: RNA
<213> ORGANISM: Homo sapiens

<400> SEQUENCE: 1
ugagguagua gguuguaugg uu                                              22

<210> SEQ ID NO 2
<211> LENGTH: 22
<212> TYPE: RNA
<213> ORGANISM: Homo sapiens

<400> SEQUENCE: 2
aaccauacaa ccuacuaccu ca                                              22

<210> SEQ ID NO 3
<211> LENGTH: 22
<212> TYPE: RNA
<213> ORGANISM: Homo sapiens

<400> SEQUENCE: 3
uuuggucccc uucaaccagc ua                                              22

<210> SEQ ID NO 4
<211> LENGTH: 21
<212> TYPE: RNA
<213> ORGANISM: Homo sapiens

<400> SEQUENCE: 4
uagcugguug aaggggacca a                                               21

<210> SEQ ID NO 5
<211> LENGTH: 22
<212> TYPE: RNA
<213> ORGANISM: Homo sapiens

<400> SEQUENCE: 5
ucucccaacc cuuguaccag ug                                              22

<210> SEQ ID NO 6
<211> LENGTH: 22
<212> TYPE: RNA
<213> ORGANISM: Homo sapiens

<400> SEQUENCE: 6
cacugguaca aggguuggga ga                                              22

<210> SEQ ID NO 7
<211> LENGTH: 22
<212> TYPE: RNA
<213> ORGANISM: Homo sapiens

<400> SEQUENCE: 7
uagguaguuu ccuguuguug gg                                              22

<210> SEQ ID NO 8
<211> LENGTH: 21
<212> TYPE: RNA
<213> ORGANISM: Homo sapiens

<400> SEQUENCE: 8
ccaacaacag gaaacuaccu a                                           21

<210> SEQ ID NO 9
<211> LENGTH: 22
<212> TYPE: RNA
<213> ORGANISM: Homo sapiens

<400> SEQUENCE: 9
uggaauguaa ggaagugugu gg                                          22

<210> SEQ ID NO 10
<211> LENGTH: 22
<212> TYPE: RNA
<213> ORGANISM: Homo sapiens

<400> SEQUENCE: 10
ccacacacuu ccuuacauuc ca                                          22

<210> SEQ ID NO 11
<211> LENGTH: 21
<212> TYPE: RNA
<213> ORGANISM: Homo sapiens

<400> SEQUENCE: 11 agggccccccc cucaauccug u                                          21

<210> SEQ ID NO 12
<211> LENGTH: 21
<212> TYPE: RNA
<213> ORGANISM: Homo sapiens

<400> SEQUENCE: 12
acaggauuga gggggggccc u                                           21

<210> SEQ ID NO 13
<211> LENGTH: 2391
<212> TYPE: DNA
<213> ORGANISM: Mus musculus

<400> SEQUENCE: 13
tgagcatcta tccagccagc caacatttcc cgaccttcag tattgccctc ttctgcaaat      60
gccaatccca agaccattc aaccccaaag ctccgtggct ccacgacaca agctgttgag      120
tgcttactgg gtgttctact gagggaacca aacactgact atccaaagag aaaaggatat     180
tttggttttc taataacgta tattattgtt ttcttctccc ctttctatgc aactgtaaat     240
taatgaacag agaagtattt ggaggtggta aagcatttgt cactgatttg tataatatat     300
acagccatgg gaaagtgggt gggggctttc taatatgaaa ctgtcttttt aataaccaag     360
agaaaaaatt gcataagaat tagaccactt tacattatta cattccttct gctgttcaca     420
ttaaccttgt acaataactt cacttattat ttgactgttt taccattatg ttttggttat     480
ttataaattt atcagccata caaacaaata gattctatgt atttgtttct ataatctggc     540
caaattccta agttcatata tttgaatcaa atatttaca tatgtggagt aggcaggcat      600
tctgaagata ctatttaact ttagttgacg tcacacacac catcctttag taaccactgg     660
atgactacac taaaaatcct gtggacttta acgcaagct gctggggtat ttttcctcct      720 gttttttattc cttttttgta agtagatctt gacgtcttta tttatttcat cttgcaatct     780

-continued

```
ctataataaa aagactgta ttgtaatagt ctcaaaaaat tattttacca agggttacca    840
tttaagcata ttttcatttt gattcagaaa ccaaagttgg tacaacctct cctagtacat    900
gcaaccttgg ttttcatgag aaaacacacg gcaggccttt gcccattgtg aggagagcac    960
acatcatgct cttcagtttc ctttgaatag acttttattg ttgttttttgt atttttcgag   1020
tcctgtgtaa gttttgaaag ctctggttgt ttcctttgtg aaagcaggca gatacttagt   1080
tggctgtctc atttgaagct ttggagcaga tagtcagatg tctcatgacc cctcacttgg   1140
ccagcagcac atccgagaag gatgtcactc acaagcctac accacggctt ctctagaatg   1200
aaatcagtgc tcggatgatt gtatccctgc ctctacttct gagtgtgttc aactaggtat   1260
tggcttcttt ttcttttcct ttctttttt ttttaattta acacttaatt gccgatttta   1320
gagaaaccaa aaataaaggt gaaggtaata tgttttgatt caaacatata tgcttttaaa   1380
catcagacat gctaactttg gttctcttta ctggaatctg gcccagagga ggtgaaattt   1440
agaaatgtta ttcttagat gggtgggtgg gttgggggc caagggtgtc tattttccag    1500
cattagatat ttttgagacg aagaaaattg ttttatataa ggggagagcc atgatcacct   1560
ttctacctca gaaccacctt cctccattgt gttggacata gctttatatg ccgcagtgtg   1620
caaaacctag ggctgtagtc aggcctttcc atacccagga agcacctgtg taaagaagat   1680
caacagaaac tcccggaact cagaaccca agttgtagat ttggtgtcgt ccttgttctt    1740
gctttgagga gtcatgtatt cttttatttc ctgcctgtat ttgtatgcaa aatgatctct   1800
atctgctatt acagaaaaag ctacacaaaa cactacattg taaccttctg agtaataaat   1860
aagaggaaat atattacagt aaccatgatg agaaataagt gtattgttct tttgaaatat   1920
gtggttaatc gcagactgtc atctaatctg ttacataccg tattttttcat cctgaataaa   1980
agtaattta acacaaaatg actttgatgt ttggctgtgt tcagctgatg aaatcagatc   2040
tctgaatgta tgtgatgaaa gctaactata agatgatcta tattctgata aatctaaata   2100
ttttctgaaa ctctctctta tacattaatc tagtctccat tcactcatta tctctctctc   2160
ctttcttgca tataaatatg attatatatt tttcaatttc ctgtacaaat cagagtctta   2220
ttactaggga aaatggatgt tataagtaca ttcctaaagc ccattgggcc ttcattttta   2280
taacttggag ctactgagat ttatcaggtt actctctcaa atccactttc atcactagac   2340
tcatagtttt ctatgtatct atattattat aactaaataa aaatatacat g           2391
```

<210> SEQ ID NO 14
<211> LENGTH: 23
<212> TYPE: DNA
<213> ORGANISM: Homo sapiens

<400> SEQUENCE: 14

```
atgggaaagt gggtgggggc ttt                                            23
```

<210> SEQ ID NO 15
<211> LENGTH: 22
<212> TYPE: DNA
<213> ORGANISM: Homo sapiens

<400> SEQUENCE: 15

```
ccactttaca ttattacatt cc                                             22
```

<210> SEQ ID NO 16
<211> LENGTH: 20
<212> TYPE: DNA
<213> ORGANISM: Homo sapiens

```
<400> SEQUENCE: 16
atgggtgggt ggggttggggg                                              20

<210> SEQ ID NO 17
<211> LENGTH: 17
<212> TYPE: DNA
<213> ORGANISM: Homo sapiens

<400> SEQUENCE: 17
gtgggttggg gggccaa                                                  17

<210> SEQ ID NO 18
<211> LENGTH: 24
<212> TYPE: DNA
<213> ORGANISM: Mus musculus

<400> SEQUENCE: 18
agccatgatc acctttctac ctca                                          24

<210> SEQ ID NO 19
<211> LENGTH: 19
<212> TYPE: DNA
<213> ORGANISM: Homo sapiens

<400> SEQUENCE: 19
ccatacccag gaagcacct                                                19

<210> SEQ ID NO 20
<211> LENGTH: 21
<212> TYPE: RNA
<213> ORGANISM: Homo sapiens

<400> SEQUENCE: 20
aaguggauau uguugccauc a                                             21

<210> SEQ ID NO 21
<211> LENGTH: 21
<212> TYPE: DNA
<213> ORGANISM: Homo sapiens

<400> SEQUENCE: 21
aguacugcuu acgauacggt t                                             21

<210> SEQ ID NO 22
<211> LENGTH: 21
<212> TYPE: DNA
<213> ORGANISM: Homo sapiens

<400> SEQUENCE: 22
ccguaucgua agcaguacut t                                             21

<210> SEQ ID NO 23
<211> LENGTH: 21
<212> TYPE: DNA
<213> ORGANISM: Homo sapiens

<400> SEQUENCE: 23
gggtgggtgg gttgggggc c                                              21

<210> SEQ ID NO 24
<211> LENGTH: 26
<212> TYPE: RNA
```

<213> ORGANISM: Mus musculus

<400> SEQUENCE: 24
cugagguaga aaggugauca uggcuc					26

<210> SEQ ID NO 25
<211> LENGTH: 26
<212> TYPE: RNA
<213> ORGANISM: Homo sapiens

<400> SEQUENCE: 25
cugagguaga aaggugguca uggcuu					26

<210> SEQ ID NO 26
<211> LENGTH: 27
<212> TYPE: RNA
<213> ORGANISM: Mus musculus

<400> SEQUENCE: 26
cugagguaga aaggugauca uggcucu					27

<210> SEQ ID NO 27
<211> LENGTH: 28
<212> TYPE: RNA
<213> ORGANISM: Mus musculus

<400> SEQUENCE: 27
cugagguaga aaggugauca uggcucuc					28

<210> SEQ ID NO 28
<211> LENGTH: 29
<212> TYPE: RNA
<213> ORGANISM: Mus musculus

<400> SEQUENCE: 28
cugagguaga aaggugauca uggcucucc					29

<210> SEQ ID NO 29
<211> LENGTH: 27
<212> TYPE: RNA
<213> ORGANISM: Mus musculus

<400> SEQUENCE: 29
ucugagguag aaaggugauc auggcuc					27

<210> SEQ ID NO 30
<211> LENGTH: 28
<212> TYPE: RNA
<213> ORGANISM: Mus musculus

<400> SEQUENCE: 30
uucugaggua gaaaggugau cauggcuc					28

<210> SEQ ID NO 31
<211> LENGTH: 29
<212> TYPE: RNA
<213> ORGANISM: Mus musculus

<400> SEQUENCE: 31
guucugaggu agaaagguga ucauggcuc					29

<210> SEQ ID NO 32
<211> LENGTH: 28

```
<212> TYPE: RNA
<213> ORGANISM: Mus musculus

<400> SEQUENCE: 32 ucgagguag aaaggugauc auggcucu                                              28

<210> SEQ ID NO 33
<211> LENGTH: 29
<212> TYPE: RNA
<213> ORGANISM: Mus musculus

<400> SEQUENCE: 33
uucugaggua gaaaggugau cauggcucu                                            29

<210> SEQ ID NO 34
<211> LENGTH: 30
<212> TYPE: RNA
<213> ORGANISM: Mus musculus

<400> SEQUENCE: 34
guucugaggu agaaagguga ucauggcucu                                           30

<210> SEQ ID NO 35
<211> LENGTH: 29
<212> TYPE: RNA
<213> ORGANISM: Mus musculus

<400> SEQUENCE: 35
ucugagguag aaaggugauc auggcucuc                                            29

<210> SEQ ID NO 36
<211> LENGTH: 30
<212> TYPE: RNA
<213> ORGANISM: Mus musculus

<400> SEQUENCE: 36
uucugaggua gaaaggugau cauggcucuc                                           30

<210> SEQ ID NO 37
<211> LENGTH: 31
<212> TYPE: RNA
<213> ORGANISM: Mus musculus

<400> SEQUENCE: 37
guucugaggu agaaagguga ucauggcucu c                                         31

<210> SEQ ID NO 38
<211> LENGTH: 30
<212> TYPE: RNA
<213> ORGANISM: Mus musculus

<400> SEQUENCE: 38
ucugagguag aaaggugauc auggcucucc                                           30

<210> SEQ ID NO 39
<211> LENGTH: 31
<212> TYPE: RNA
<213> ORGANISM: Mus musculus

<400> SEQUENCE: 39
uucugaggua gaaaggugau cauggcucuc c                                         31

<210> SEQ ID NO 40
```

```
<211> LENGTH: 32
<212> TYPE: RNA
<213> ORGANISM: Mus musculus

<400> SEQUENCE: 40
guucugaggu agaaagguga ucauggcucu cc                              32

<210> SEQ ID NO 41
<211> LENGTH: 27
<212> TYPE: RNA
<213> ORGANISM: Homo sapiens

<400> SEQUENCE: 41
cugagguaga aggugguca uggcuuu                                     27

<210> SEQ ID NO 42
<211> LENGTH: 28
<212> TYPE: RNA
<213> ORGANISM: Homo sapiens

<400> SEQUENCE: 42
cugagguaga aggugguca uggcuuuc                                    28

<210> SEQ ID NO 43
<211> LENGTH: 29
<212> TYPE: RNA
<213> ORGANISM: Homo sapiens

<400> SEQUENCE: 43
cugagguaga aggugguca uggcuuucc                                   29

<210> SEQ ID NO 44
<211> LENGTH: 27
<212> TYPE: RNA
<213> ORGANISM: Homo sapiens

<400> SEQUENCE: 44
ucugagguag aaaggugguc auggcuu                                    27

<210> SEQ ID NO 45
<211> LENGTH: 28
<212> TYPE: RNA
<213> ORGANISM: Homo sapiens

<400> SEQUENCE: 45
aucugaggua gaaaggugu cauggcuu                                    28

<210> SEQ ID NO 46
<211> LENGTH: 29
<212> TYPE: RNA
<213> ORGANISM: Homo sapiens

<400> SEQUENCE: 46
gaucugaggu agaaaggugg ucauggcuu                                  29

<210> SEQ ID NO 47
<211> LENGTH: 28
<212> TYPE: RNA
<213> ORGANISM: Homo sapiens

<400> SEQUENCE: 47
ucugagguag aaaggugguc auggcuuu                                   28
```

```
<210> SEQ ID NO 48
<211> LENGTH: 29
<212> TYPE: RNA
<213> ORGANISM: Homo sapiens

<400> SEQUENCE: 48
aucugaggua gaaagguggu cauggcuuu                                    29

<210> SEQ ID NO 49
<211> LENGTH: 30
<212> TYPE: RNA
<213> ORGANISM: Homo sapiens

<400> SEQUENCE: 49
gaucugaggu agaaaggugg ucauggcuuu                                   30

<210> SEQ ID NO 50
<211> LENGTH: 29
<212> TYPE: RNA
<213> ORGANISM: Homo sapiens

<400> SEQUENCE: 50
ucugagguag aaaggugguc auggcuuuc                                    29

<210> SEQ ID NO 51
<211> LENGTH: 30
<212> TYPE: RNA
<213> ORGANISM: Homo sapiens

<400> SEQUENCE: 51
aucugaggua gaaagguggu cauggcuuuc                                   30

<210> SEQ ID NO 52
<211> LENGTH: 31
<212> TYPE: RNA
<213> ORGANISM: Homo sapiens

<400> SEQUENCE: 52
gaucugaggu agaaaggugg ucauggcuuu c                                 31

<210> SEQ ID NO 53
<211> LENGTH: 30
<212> TYPE: RNA
<213> ORGANISM: Homo sapiens

<400> SEQUENCE: 53
ucugagguag aaaggugguc auggcuuucc                                   30

<210> SEQ ID NO 54
<211> LENGTH: 31
<212> TYPE: RNA
<213> ORGANISM: Homo sapiens

<400> SEQUENCE: 54
aucugaggua gaaagguggu cauggcuuuc c                                 31

<210> SEQ ID NO 55
<211> LENGTH: 32
<212> TYPE: RNA
<213> ORGANISM: Homo sapiens

<400> SEQUENCE: 55
gaucugaggu agaaaggugg ucauggcuuu cc                                32
```

<210> SEQ ID NO 56
<211> LENGTH: 2045
<212> TYPE: DNA
<213> ORGANISM: Homo sapiens

<400> SEQUENCE: 56

```
tgaagtattc atccggccaa ccaatgtttc ctgacgtaca gtgttgccct tttcagcaaa      60
tgccaattcc aagttccatt aaatcagaag ctccatggct ccttggccca cgatgttgag     120
tgctgactgt gtgttctact gaaagagtaa acactgact atccaaagag aaatggatat      180
tttgttttta taataaccat atattattgt tttcttcttc cctttctatg caagtgtaaa     240
ttaatgaaca gagaggtatt tggaaatggt aatacatttg tcacggattt gtataatgta     300
tacagcattg ggaaagtggg tgggggcttt ctaatatgat accgtctttt taataactat     360
gacaaagctt acataagaat tagaagacca ctttacattt ttacattcct tctgctgttc     420
atattaacct tgcacaatta cttcattttt tctttgactc ttttaccaca atgttttggt     480
tatttataat ttatcagcca tatgtttatc agccatataa ccaactagat cccaaataga     540
tccatgtatt tgtttccgtg atttggccac attaataaat tcataaattt caatcaaata     600
tcttatatat acacacatat ggtttaagct acagccctgt gtatgccgtt aactttatt     660
tgacgttgcc cacttacttc tttgctgacc acttggataa ccgtaataaa aatcctataa     720
gcctaaatgg catttctttt gggatatttt tcctgcattt tattccctt ttatataagt      780
aggaattaat tatttatttt atgtcttaat ctatttgata agaagacta cattataata      840
atctcaaaga tcatattacc aaaggttgcc cacttgagca tattttcatt ttgacacaga     900
aacaaaattt agtacaacct ttcctagttc ccatgtcttg attttcatca ttacatgcac     960
agcagacctt tacctattgt gataccagaa cacatcattg tctttggttc ccttcaagaa   1020
gaattttatt gttgttttgt attttcaagt ccttaatagt tcttgaaact cctagttgtt   1080
ttcttgttga aagcagacac acattagtg cacggcttat tttacccttc gggtgaaaga    1140
tcagatgttt ttatacccctt cacttgatca atatatttgg aaagaatgtt tatcaaaagt   1200
ctatgtcact gcttctacag aagaatgaaa ttaatgctta ggtgatggta cctccaccta   1260
catctttttg agtgcattca attatgtatt ttggtttagc ttctgattta acatttaatt   1320
gattcagttt aaacatgtta cttaattagc aaatgtagag gaaccaaaaa aaggtgaaaa   1380
taatatgttt tgattcaaac ctaaagacat aaaaacataa agacatttta actttgggtt   1440
ctctttagct gggatctggc cagaaggagg cttaaagtta gaaattgcta ttatttaga    1500
ataggttggg tgggttgggg ggcaagggtg tctatttgca gcagagatat tttgaaaaga    1560
agaaaattgt tttatataaa aaggaaagcc atgaccacct ttctacctca gatccatctt   1620
catccattgc attggaaact gctttatgct gctgcagtct gcaaagtcta gagctttat    1680
caggccatgt catacccaag aaagcaccta tttaaagaaa aaacaattcc ctgagctctc   1740
aactccaagt tgtagatttg gtgtcttcct tgttcttact ttaaaaagtc atgtgttaat   1800
tttttttctg cctgtatttg tatgcaaaat gtcctctatc tgctattaaa gaaaagctac   1860
gtaaaacact acattgtaac cttctaagta ataataaata aaagaaata tattgcagta    1920
acaatgggaa gtaagtatgt agttcttttg aaatatgtgg taagaactaa atcacagact   1980
atcatctaat ctggttacat attgtatttt tcatcctgaa taaagtaat tttaacacaa    2040
aaaaa                                                                2045
```

```
<210> SEQ ID NO 57
<211> LENGTH: 23
<212> TYPE: DNA
<213> ORGANISM: Homo sapiens

<400> SEQUENCE: 57
ttgggaaagt gggtgggggc ttt                                              23

<210> SEQ ID NO 58
<211> LENGTH: 26
<212> TYPE: DNA
<213> ORGANISM: Homo sapiens

<400> SEQUENCE: 58
ataggttggg tgggttgggg ggcaag                                           26

<210> SEQ ID NO 59
<211> LENGTH: 25
<212> TYPE: DNA
<213> ORGANISM: Homo sapiens

<400> SEQUENCE: 59
gaccacttta cattttttaca ttcct                                           25

<210> SEQ ID NO 60
<211> LENGTH: 22
<212> TYPE: DNA
<213> ORGANISM: Homo sapiens

<400> SEQUENCE: 60
ataggttggg tgggttgggg gg                                               22

<210> SEQ ID NO 61
<211> LENGTH: 24
<212> TYPE: DNA
<213> ORGANISM: Homo sapiens

<400> SEQUENCE: 61
aggttgggtg ggttgggggg caag                                             24

<210> SEQ ID NO 62
<211> LENGTH: 24
<212> TYPE: DNA
<213> ORGANISM: Homo sapiens

<400> SEQUENCE: 62
agccatgacc acctttctac ctca                                             24

<210> SEQ ID NO 63
<211> LENGTH: 24
<212> TYPE: DNA
<213> ORGANISM: Homo sapiens

<400> SEQUENCE: 63
atccattgca ttggaaactg cttt                                             24

<210> SEQ ID NO 64
<211> LENGTH: 26
<212> TYPE: DNA
<213> ORGANISM: Human

<400> SEQUENCE: 64
cugagguaga aaggugauca uggcuc                                           26
```

```
<210> SEQ ID NO 65
<211> LENGTH: 21
<212> TYPE: DNA
<213> ORGANISM: Human

<400> SEQUENCE: 65
cugagguaga aaggugatca u                                              21

<210> SEQ ID NO 66
<211> LENGTH: 21
<212> TYPE: DNA
<213> ORGANISM: Human

<400> SEQUENCE: 66
guagaaaggt gaucatggcu c                                              21

<210> SEQ ID NO 67
<211> LENGTH: 26
<212> TYPE: DNA
<213> ORGANISM: Homo Sapien

<400> SEQUENCE: 67
cugaggtaga aaggtgauca uggcuc                                         26

<210> SEQ ID NO 68
<211> LENGTH: 22
<212> TYPE: DNA
<213> ORGANISM: Human

<400> SEQUENCE: 68
cugaggtaga aaggtgauca ug                                             22

<210> SEQ ID NO 69
<211> LENGTH: 22
<212> TYPE: DNA
<213> ORGANISM: Homo Sapiens

<400> SEQUENCE: 69
ggtagaaagg tgaucauggc uc                                             22

<210> SEQ ID NO 70
<211> LENGTH: 26
<212> TYPE: DNA
<213> ORGANISM: Homo Sapiens

<400> SEQUENCE: 70
cugagguaga aaggtgatca uggcuc                                         26

<210> SEQ ID NO 71
<211> LENGTH: 21
<212> TYPE: DNA
<213> ORGANISM: Human

<400> SEQUENCE: 71
cugaggtaga aaggtgauca u                                              21

<210> SEQ ID NO 72
<211> LENGTH: 21
<212> TYPE: DNA
<213> ORGANISM: Human

<400> SEQUENCE: 72
guagaaaggt gatcatggcu c                                              21
```

```
<210> SEQ ID NO 73
<211> LENGTH: 26
<212> TYPE: DNA
<213> ORGANISM: Human

<400> SEQUENCE: 73
ctgagguaga aaggugatca uggcuc                                          26

<210> SEQ ID NO 74
<211> LENGTH: 21
<212> TYPE: DNA
<213> ORGANISM: Human

<400> SEQUENCE: 74
ctgagguaga aaggugatca u                                               21

<210> SEQ ID NO 75
<211> LENGTH: 21
<212> TYPE: DNA
<213> ORGANISM: Human

<400> SEQUENCE: 75
gtagaaaggt gaucatggct c                                               21

<210> SEQ ID NO 76
<211> LENGTH: 25
<212> TYPE: DNA
<213> ORGANISM: Human

<400> SEQUENCE: 76
gugagcacut cuuccttcu uttuu                                            25
```